(12) United States Patent
Tomikawa et al.

(10) Patent No.: US 6,370,479 B1
(45) Date of Patent: *Apr. 9, 2002

(54) METHOD AND APPARATUS FOR EXTRACTING AND EVALUATING MUTUALLY SIMILAR PORTIONS IN ONE-DIMENSIONAL SEQUENCES IN MOLECULES AND/OR THREE-DIMENSIONAL STRUCTURES OF MOLECULES

(75) Inventors: Mayumi Tomikawa; Seiichi Aikawa; Fumiko Matsuzawa, all of Kawasaki (JP)

(73) Assignee: Fujitsu Limited, Kawasaki (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/014,867

(22) Filed: Feb. 8, 1993

(30) Foreign Application Priority Data

Feb. 6, 1992 (JP) .............................................. 4-021012
Dec. 11, 1992 (JP) .............................................. 4-331703

(51) Int. Cl.[7] .......................... G06F 19/00; G01N 33/48; G01N 33/50
(52) U.S. Cl. .............................. 702/20; 436/63; 702/27
(58) Field of Search ................................ 364/496, 497, 364/578; 395/600; 702/20, 19, 27; 703/11; 436/63

(56) References Cited

U.S. PATENT DOCUMENTS

| | | | | |
|---|---|---|---|---|
| 4,823,306 A | * | 4/1989 | Barbic et al. ................ | 395/600 |
| 4,853,871 A | * | 8/1989 | Pantoliano et al. ......... | 3464/496 |
| 4,939,666 A | * | 7/1990 | Hardman ..................... | 364/496 |
| 5,157,736 A | * | 10/1992 | Boyer et al. ................. | 364/496 |
| 5,200,910 A | * | 4/1993 | Subbiah ....................... | 364/499 |
| 5,241,470 A | * | 8/1993 | Lee et al. .................... | 364/496 |
| 5,263,159 A | * | 11/1993 | Mitsui ......................... | 395/600 |
| 5,331,573 A | * | 7/1994 | Balaji et al. ................. | 364/578 |
| 5,410,493 A | * | 4/1995 | Konagaya .................... | 364/496 |
| 5,446,798 A | | 8/1995 | Morita et al. ................ | 382/154 |

OTHER PUBLICATIONS

Vriend and Sander, "Detection of Common Three–Dimensional Substructures in Proteins"Proteins: Structure, Function, and Genetics, No. 1, 1991, pp. 52–58.

(List continued on next page.)

*Primary Examiner*—Kyle J. Choi
(74) *Attorney, Agent, or Firm*—Staas & Halsey LLP

(57) ABSTRACT

In the analysis of one-dimensional sequences of molecules, the longest common subsequence, the number of elements constituting the subsequence, and appearance positions of the subsequence are determined by a novel and simple method, and processes, such as homology decision, homology search, motif search and alignment are performed based on the results. In the analysis of these-dimensional structures of molecules, limiting conditions, such as geometrical arrangements of elements, are introduced to realize the determination of correspondence of three-dimensional structures at high speeds, and whereby it is made possible to achieve such processing as superposed display of three-dimensional structure of molecules, retrieval of three-dimensional structure, and evaluation of functions. Moreover, the molecules are divided into secondary structure that are then related to each other based on spatial similarity among the secondary structures. Furthermore, similarity among the molecules is decided based on a relationship of spatial positions of the corresponding secondary structures.

7 Claims, 45 Drawing Sheets

OTHER PUBLICATIONS

Alexandrov, Takahashi, and Go, "Common Spatial Arrangements of Backbone Fragments in Homologous and Non-homologous Proteins" Journal of Molecular Biology, (1992) 225, pp. 5–9.

Shoichi Sato and Toru Yao, "Homology Analysis of Protein Conformational Data," The Tenth Chemistry Information Discussion Meeting, Nov. 6–Nov. 8, 1987, The Fifteenth Structure–Activity Relationship Program, Nov. 6–Nov. 8, 1987, pp. 88–92 (English Translation numbered as pp. 1–6).

Toru Kitanaka and Hideaki Umeyama, "Development of a Protein Modeling Method by Using Known Conformations", The Tenth Chemistry Information Discussion Meeting, Nov. 6–Nov 8, 1987, The Fifteenth Structure–Activity Relationship Program, Nov. 6–Nov. 8, 1987, pp. 354–357 (English Translation numbered as pp. 7–15).

Nobuo Tomioka and Akiko Itai, "A Variety of Computer Images Molecular Designing and Molecular Modeling", pp. 64, 65, et seq. (English Translation numbered as pp. 16–23).

Orengo, Brown, and Taylor, "Fast Structure Alignment for Protein Databank Searching" Proteins: Structure, Function, and Genetics 14:139–167 (1992).

* cited by examiner

Fig. 6

CHARACTER SEQUENCE II = "BDCABA"

Fig. 10 human : GDVEKGKKIFIMKCSQCHTVEGGKHKTGPNLHGLFGRK bacterium : EGDAAAGEKVSKKCLACHTFDQGGANKVGPNPNLFGVF LCS : GD{x3,3}G{x0,1}K{x0,2}K{x4,0}KC{x2,2}CHT{x3,3}GG{x2,2}K GD{x1,4}E{x0,2}K{x0,2}K{x0,4}KC{x2,2}CHT{x3,3}GG{x2,2}K homology : 47%

Fig. 11

Rat : MSLAILRVIRLVRVFRIFKLSRHSKGLQILGRTLKASMRELGLLIFFIGVV leucinzip. L{6}L{6}L{6}L{6}L

Fig. 12

```
human    : GDVEK G K KIFIMKCSQCHTVEKGG KHKTGPNLHGLFGRK...
bacterium: E GDAAAGEKVSK KCLACHTFDQGGANKV GPNPN LFGVF...
```

$B = \{b1, b2, \ldots bj, \ldots bn\}$ $A = \{a1, a2, \ldots ai, \ldots am\}$ $$\text{r.m.s.d} = \frac{\sqrt{\sum_{k=1}^{n} w_k (Ub_k - a_k)^2}}{n}$$

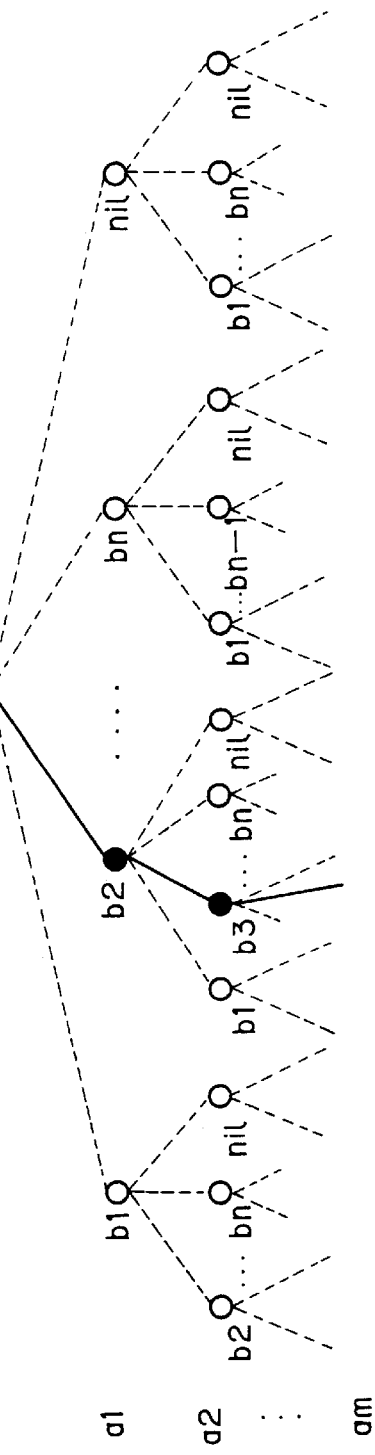
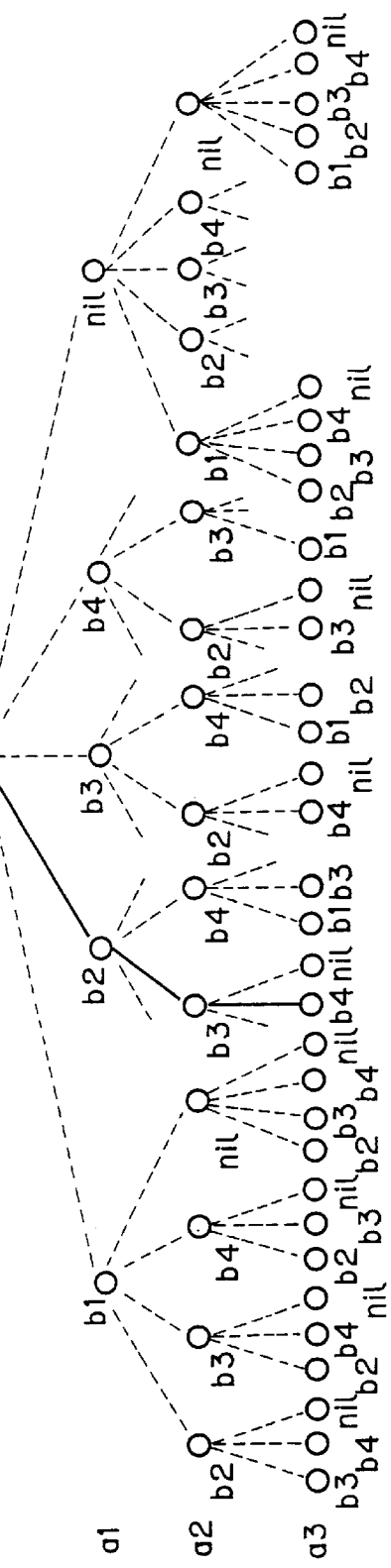
Fig. 14 A
Fig. 14 B

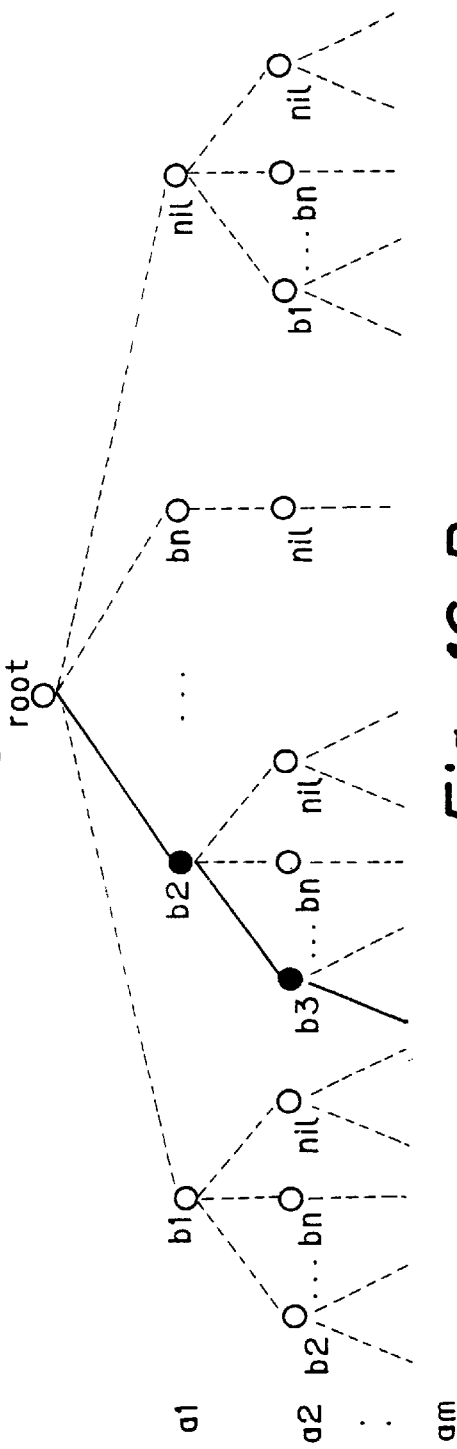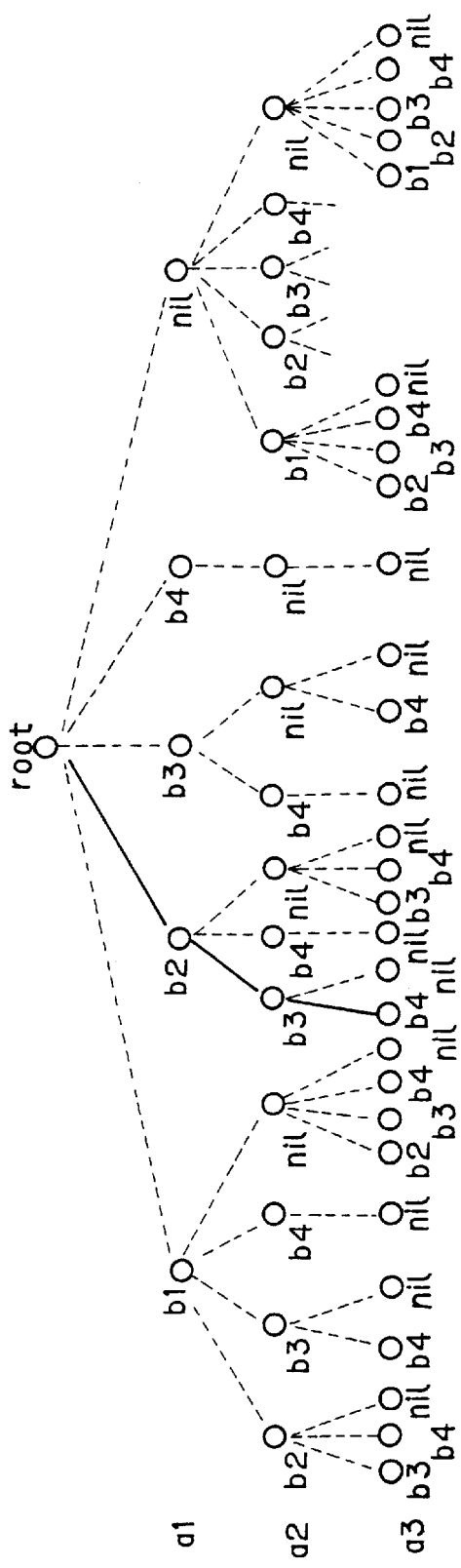

AMINO ACID SEQUENCE OF CALMODULIN
(EXCERPT FROM PDB)

AMINO ACID SEQUENCE OF TROPONIN C
(EXCERPT FROM PDB)

TROPONIN C

CALMODULIN

Fig. 25

Probe site = 81-108 in Calmodulin

| 96 | 97 | 98 | 99 | 100 | 101 | 102 | 103 | 104 | 105 | 106 | 107 | 108 | 109 | 110 |
|----|----|----|----|-----|-----|-----|-----|-----|-----|-----|-----|-----|-----|-----|
| L  | A  | D  | C  | F   | R   | I   | F   | D   | K   | N   | A   | D   | G   | F   | < target >
| I  | R  | E  | A  | F   | R   | V   | F   | D   | K   | D   | G   | N   | G   | Y   | < probe >

| 111 | 112 | 113 | 114 | 115 | 116 | 117 | 118 | 119 | 120 | 121 | 122 | 123 |
|-----|-----|-----|-----|-----|-----|-----|-----|-----|-----|-----|-----|-----|
| I   | D   | I   | E   | E   | L   | G   | E   | I   | L   | R   | A   | T   | < target >
| I   | S   | A   | A   | E   | L   | R   | H   | V   | M   | T   | N   | L   | < probe > rmsd = 0.567034

Fig. 26

Probe site = 81-108 and 117-143 in Calmodulin

| 96 | 97 | 98 | 99 | 100 | 101 | 102 | 103 | 104 | 105 | 106 | 107 | 108 | 109 | 110 | |
|---|---|---|---|---|---|---|---|---|---|---|---|---|---|---|---|
| L | A | D | C | F | R | I | F | D | K | N | A | D | G | F | < target > |
| I | R | E | A | F | R | V | F | D | K | D | G | N | G | Y | < probe > |

| 111 | 112 | 113 | 114 | 115 | 116 | 117 | 118 | 119 | 120 | 121 | 122 | 123 | |
|---|---|---|---|---|---|---|---|---|---|---|---|---|---|
| I | D | E | E | L | G | E | I | R | E | A | R | T | < target > |
| I | S | A | A | E | L | R | H | V | M | T | N | L | < probe > |

| 132 | 133 | 134 | 135 | 136 | 137 | 138 | 139 | 140 | 141 | 142 | 143 | 144 | 145 | |
|---|---|---|---|---|---|---|---|---|---|---|---|---|---|---|
| I | E | D | L | M | K | D | S | D | K | N | D | G | G | < target > |
| V | D | E | M | I | R | E | A | N | I | D | G | D | G | < probe > |

| 146 | 147 | 148 | 149 | 150 | 151 | 152 | 153 | 154 | 155 | 156 | 157 | 158 | |
|---|---|---|---|---|---|---|---|---|---|---|---|---|---|
| R | I | D | F | D | E | F | L | K | M | M | E | G | < target > |
| Q | V | N | Y | E | E | F | V | Q | M | M | T | A | < probe > | rmsd = 0.823665

Fig. 29

```
========== ATP/GTP binding site ==========================

Probe = (elongation factor)

7  8  9 10 11 12 13 14
     G  H  V  D  H  G  K  T    < probe >
-----
     8  9 10 11 12 13 14 15
     G  A  P  G  S  G  K  G    << target >>
     G  H  V  D  H  G  K  T    << probe  >>
     rmsd=0.648732  adenylate kinase unit - A
  ...
    10 11 12 13 14 15 16 17
     G  A  G  G  V  G  K  S    << target >>
     G  H  V  D  H  G  K  T    << probe  >>
     rmsd=0.421770  ras protein
```

Fig. 32 A
Fig. 32 B
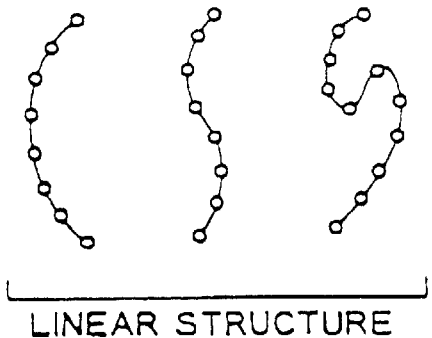
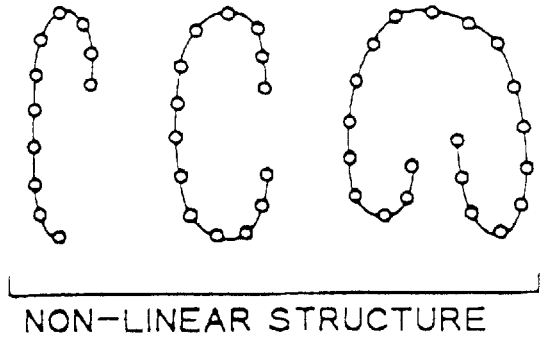
LINEAR STRUCTURE
NON-LINEAR STRUCTURE
Fig. 33
WHEN f(x)=2x
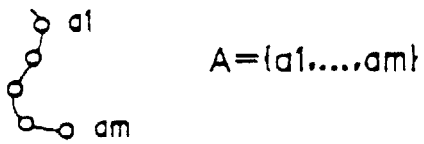
$A = \{a1,....,am\}$
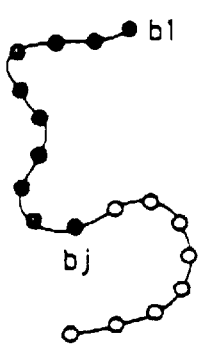 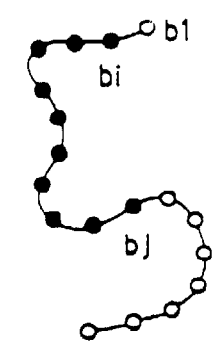 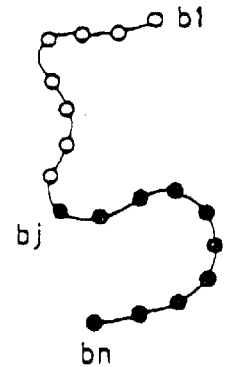
$B = \{b1,....,bi,....,bj,....,bn\}$ A={a1,a2,....am}

AMINO ACID SEQUENCE OF TRYPSIN (EXCERPT FROM PDB)

AMINO ACID SEQUENCE OF ELASTASE (EXCERPT FROM PDB)

Fig. 39 A

```
Key site number 36 - 41 in Trypsin 41 42 43 44 45 46
 M  T  A  A  H  C   < target >
 V  S  A  A  H  C   < probe  > d = 12.070038 [A]
r.m.s.d. = 0.061077 [A]
The number of atoms in a probe = 6
The number of atoms in PDB = 240
The number of combination = 1
Time = 1sec
```

RETRIEVED RESULTS OF HISTIDINE ACTIVE SITES

Fig. 39 B

```
Key site number 175 - 179 in Trypsin 186 187 188 189 190
 G   D   S   G   G   < target >
 G   D   S   G   G   < probe  > d = 8.922721 [A]
r.m.s.d. = 0.092879 [A]
The number of atoms in a probe = 5
The number of atoms in PDB = 240
The number of combination = 1
Time = 1sec
```

RETRIEVED RESULTS OF SERINE ACTIVE SITES

Fig. 44

| SUBSET | COORDINATES | TYPE |
|---|---|---|
| S1 | $\{X_1, X_2, X_3, X_4, \cdots\cdots X_a\}$ | $\alpha$ — HELIX |
| S2 | $\{X_{a+1}, X_{a+2}, \cdots\cdots\cdots X_b\}$ | $\alpha$ — HELIX |
| S3 | $\{X_{b+1}, X_{b+2}, \cdots\cdots\cdots X_c\}$ | $\beta$ — SHEET |
| S4 | $\{X_{c+1}, X_{c+2}, \cdots\cdots\cdots X_d\}$ | $\beta$ — SHEET |
| ⋮ | ⋮ | ⋮ |
| Sn | $\{X_{l+1}, X_{l+2}, \cdots\cdots\cdots X_m\}$ | 3 — TURN |

162

PROTEIN B HAVING A SIMILAR STRUCTURE

KEY PROTEIN A

METHOD AND APPARATUS FOR EXTRACTING AND EVALUATING MUTUALLY SIMILAR PORTIONS IN ONE-DIMENSIONAL SEQUENCES IN MOLECULES AND/OR THREE-DIMENSIONAL STRUCTURES OF MOLECULES

BACKGROUND OF THE INVENTION

1. Field of the Invention

This invention relates to method and apparatus for extracting and evaluating mutually coinciding or similar portions between sequences of atoms or atomic groups in molecules and/or between three-dimensional structures of molecules and, particularly to a method and apparatus for automatically extracting and evaluating mutually coinciding or similar portions between amino acid sequences in protein molecules and/or between three-dimensional structures of protein molecules.

2. Description of the Related Art

A gene is in substance DNA, and is expressed as a base sequence including four bases of A (adenine), T (thymine), C (cytosine), and G(guanine). There are about twenty types of amino acids constituting an organism, and it has been shown that arrangements of three bases correspond to the respective amino acids. Accordingly, it has been found out that the amino acids are synthesized according to the base sequences of the DNA in the organism and that a protein is formed by folding the synthesized amino acids. The arrangement of amino acids is expressed as an amino acid sequence in which the respective amino acids are expressed in letters similar to the base sequence.

A method for determining a sequence of bases and amino acids has been established together with the development of molecular biology, and therefore a huge amount of gene information including a base sequence data and an amino acid sequence data has been stored. Thus, in the field of gene information processing, a core subject has been how to extract biological information concerning the structure and function of the protein out of the huge amount of stored gene information.

A basic technique in extracting the biological information is to compare the sequences. This is because it is considered that a similarity is found in the biological function if the sequences are similar. Accordingly, by searching a data base of known sequences whose functions are known for a sequence similar to an unknown sequence a homology search for estimating a function of an unknown sequence, and an alignment such that a sequence is rearranged so as to maximize the degree of analogy between the compared sequences when researchers compare the sequences are presently studied.

Further, it is considered that a region of the sequence, in which a function important for the organism is coded, is perpetuated in the evolution process. For instance, a commonly existing sequence pattern (region) is known to be found when the amino acid sequences in proteins having the same function are compared between different types of organisms. This region is called a motif. Accordingly, if it is possible to extract the motif automatically, the property and function of the protein can be shown by finding which motif is included in the sequence. Further, the automatic motif extraction is applicable to a variety of protein engineering fields such as strengthening of the properties of the preexisting proteins, addition of functions to the preexisting proteins, and synthesis of new proteins. As described above, it can be considered as an effective means in extracting the biological information to extract the motif out of the amino acid sequence. However, the extracting method is not yet established, and the researchers currently decide manually which part is a motif sequence after the homology search and alignment.

A dynamic programming technique that is used in a voice recognition processing has been the only method used for automatically comparing two amino acid sequences.

However, according to the method of comparing the amino acid sequences using the dynamic programming technique, the amino acid sequences are compared two-dimensionally. Thus, this method requires a large memory capacity and a long processing time.

Meanwhile, in the fields of physics and chemistry, in order to examine the properties of a new (unknown) substance and to produce the new substance artificially, three-dimensional structures of substances are determined by a technique such as an X-ray crystal analysis or an NMR analysis, and information on the determined three-dimensional structures is stored in a data base. As a typical data base, a PDB (Protein Data Bank) in which three-dimensional structures of proteins or the like identified by the X-ray crystal analysis of protein are registered is widely known and universally used. Further, a CSD (Cambridge Structural Database) is known as a data base in which chemical substances are registered.

In the protein, a plurality of amino acids are linked to one another as a single chain and this chain is folded in an organism to thereby form a three-dimensional structure. In this way, the protein exhibits a variety of functions. The respective amino acids are expressed by numbering them from an N-terminal through a C-terminal. These numbers are called amino acid numbers, amino acid sequence numbers, or amino acid residue numbers. Each amino acid includes a plurality of atoms according to the type thereof. Therefore, there are registered names and administration numbers of protein, amino acid numbers constituting the protein, types and three-dimensional coordinates of atoms constituting the respective amino acids, and the like in the PDB.

It is known that the three-dimensional structure of the substance is closely related to the function thereof from the result of chemical studies conducted thus far, and a relationship between the three-dimensional structure and function is shown through a chemical experiment in order to change the substance and to produce a substance having a new function. Particularly, since a structurally similar portion (or a specific portion) between the substances having the same function is considered to influence the function of the substance, it is essential to discover a similar structure commonly existing in the three-dimensional structures.

However, since there is no method of extracting a characteristic portion directly from the three-dimensional coordinate, the researchers are at present compelled to express the respective three-dimensional structures in a three-dimensional graphic system and to search the characteristic portion manually. There is in general no method of determining an orientation of the substance, and thus the characteristic portion is searched while rotating one substance using the other substance as a reference, which requires a substantial amount of time.

When the researcher searches the similar three-dimensional structure, an r.m.s.d (root mean square distance) value is used as a scale of the similarity of the three-dimensional structures of the substances. The r.m.s.d value is a value expressing a square root of a mean square distance between the corresponding elements constituting the substances. Empirically, the substances are thought to be exceedingly similar to each other in the case where the r.m.s.d value between the substances is not greater than 1 Å.

For instance, it is assumed that there are substances expressed by a point set $A=\{a_1, a_2, \ldots, a_i, \ldots, a_m\}$ and a point set $B=\{b_1, b_2, \ldots, b_j, \ldots, b_n\}$, wherein $a_i$ (i=1, 2, ..., m) and $b_j$ (i=1, 2, ..., n) are vectors expressing positions of the respective elements in the three-dimensional space. The elements constituting these substances A and B are related to each other, and the substance B is rotated and moved so that the r.m.s.d value between the corresponding elements is minimized. For example, if $a_k$ is related to $b_k$ (k=1, 2, ..., n), the r.m.s.d value is obtained in the following equation (1) wherein U denotes a rotation matrix and $W_k$ denote respective weights:

$$\mathrm{r.m.s.d.} = \frac{\left(\sum_{k=1}^{n}(w_k(Ub_k - a_k)^2)\right)^{\frac{1}{2}}}{n} \quad (1)$$

A technique of obtaining the rotation and movement of the substances, which minimizes the r.m.s.d value between these corresponding points, is proposed by Kabsh et al. (for example, refer to "A Solution for the Best Rotation to Relate Two Sets of Vectors," by W. Kabsh, Acta Cryst. (1976), A32, 923), and is presently widely used. However, since the same number of points are compared according to this method, the researchers are presently studying, by trial and error, which combinations of elements are related to the other substances so as to obtain the minimum r.m.s.d value.

Further, it is necessary to study the preexisting substances in order to produce the new substance. For instance, in the case where the heat resistance of a certain substance is preferably strengthened, a structure commonly existing among the strong heat resisting substances is determined, and such a structure is added to a newly produced substance to thereby strengthen the function of the substance. To this end, such a function is required as to retrieve the necessary structure from the data base. However, the researchers are presently studying the necessary structure from the data base, by trial and error, using the computer graphic system for the aforementioned reasons.

As described above, the operators are compelled to graphically display the three-dimensional structure of the substance they want to analyze using the graphic system, and to analyze by visual comparison with other molecules on a screen, superposition, and like operations.

Meanwhile, basic structures such as an α helix and a β strand are commonly found in the three-dimensional structure of protein, and they are called a secondary structure. Methods of carrying out an automatic search by a similarity of the secondary structure without using the r.m.s.d. value have been considered. According to these methods, a partial structure is expressed by symbols of the secondary structures along the amino acid sequence and the comparison is made using these symbols. Therefore, the comparison could not be made according to a similarity of the spatial positional relationship of the partial structure.

As mentioned above, the case where the three-dimensional structure of the substance is analyzed using the CSD and PDB, a great amount of time and labor are required to manually search a huge amount of data for a structure and to compare the retrieved structure with the three-dimensional structure to be analyzed, thereby imposing a heavy burden on the operators. For that matter, the data included in the data base cannot be utilized effectively, thus presenting the problem that the structure of the substance cannot be analyzed sufficiently. Accordingly, there has been the need for a retrieval system that retrieves the structure based on the analogy of the three-dimensional structures of the three-dimensional structure data base.

SUMMARY OF THE INVENTION

An object of the invention is to provide method and apparatus capable of automatically extracting and evaluating mutually coinciding or similar portions between sequences of atoms or atomic groups in molecules such as protein molecules in accordance with a simple processing mechanism.

Another object of the invention is to provide method and apparatus capable of automatically extracting and evaluating mutually coinciding or similar portions between three-dimensional structures of the molecules such as protein molecules.

In accordance with the present invention there is provided a method of analyzing sequences of atomic groups including a first sequence having m atomic groups and a second sequence having n atomic groups where m and n are integers, comprising the steps of:

a) preparing an array S[i] having array elements S[0] to S[m];

b) initializing all array elements of the array S[i] to zero and initializing an integer j to 1;

c) adding 1 to each array element S[i] that is equal to an array element S[r] and that i≧r if the array element S[r] is equal to an array element S[r−1] where r is an occurrence position of j-th atomic group of the second sequence in the first sequence;

d) adding 1 to the integer j;

e) repeating the steps c) and d) until the integer j exceeds n; and f) obtaining a longest common atomic group number between the first and the second sequences from a value of the array element S[m].

It is preferable that the method further comprises the steps of:

g) preparing an array data[k] having array elements data[0], datat[1] . . . ;

h) storing paired data (r, j) in an array element data[k] if the array element S[i] is changed in the step c) where k=s[r];

i) linking the paired data (r, j) stored in the step h) to paired data (r', j') if r'<r and j'<j where the paired data (r', j') is one stored in an array element data[k−1]; and j) obtaining a longest common subsequence between the first and the second sequences and occurrence positions of the longest common subsequence in the first and the second sequence by tracing the link formed in the step i).

In accordance with the present invention there is also provided a method of analyzing three-dimensional structures including a first structure expressed by three-dimensional coordinates of elements belonging to a first point set and a second structure expressed by three-dimensional coordinates of elements belonging to a second point set, comprising the steps of:

a) generating a combination of correspondence satisfying a restriction condition between the elements belonging to the first point set and the elements belonging to the second point set from among all candidates for the combination of correspondence; and b) calculating a root mean square distance between the elements corresponding in the combination of correspondence generated in the step a).

In accordance with the present invention there is also provided a method of analyzing three-dimensional structures including a first structure expressed by three-dimensional coordinates of elements belonging to a first point set and a second structure expressed by three-dimensional coordinates of elements belonging to a second point set, comprising the steps of:

a) dividing the second point set into a plurality of subsets having a size that is determined by the size of the first point set;

b) generating a combination of correspondence satisfying a restriction condition between the elements belonging to the first point set and the elements belonging to each of the subsets of the second point set from among all candidates for the combination of correspondence; and c) calculating a root mean square distance between the elements corresponding in the combination of correspondence generated in the step b).

In accordance with the present invention there is also provided a method of analyzing three-dimensional structures including a first structure expressed by three-dimensional coordinates of elements belonging to a first point set and a second structure expressed by three-dimensional coordinates of elements belonging to a second point set, comprising the steps of:

a) dividing the first point set and the second point set into first subsets and second subsets, respectively, according to a secondary structure exhibited by the three-dimensional coordinates of the elements of the first and the second point sets;

b) generating a combination of correspondence satisfying a first restriction condition between the first subsets and the second subsets from among candidates for the combination of correspondence;

c) determining an optimum correspondence between the elements belonging to each pair of subsets corresponding in the combination of correspondence generated in the step b), and d) calculating a root mean square distance between all of the elements corresponding in the optimum correspondence in the step c).

In accordance with the present invention there is also provided an apparatus for analyzing sequences of atomic groups including a first sequence having m atomic groups and a second sequence having n atomic groups where m and n are integers, comprising:

means for preparing an array S[i] having array elements S[0] to S[m];

means for initializing all array elements of the array S[i] to zero and initializing an integer j to 1;

means for renewing the array S[i] by adding 1 to each array element S[i] that is equal to an array element S[r] and that i≧r if the array element S[r] is equal to an array element S[r−1] where r is an occurrence position of j-th atomic group of the second sequence in the first sequence;

means for incrementing the integer j by 1;

means for repeatedly activating the renewing means and the incrementing means until the integer j exceeds n; and means for obtaining a longest common atomic group number between the first and the second sequences from a value of the array element S[m].

It is preferable that the apparatus further comprises:

means for preparing an array data[k] having array elements data[0], data[1] . . . ;

means for storing paired data (r, j) in an array element data[k] if the array element S[i] is changed by the renewing means where k=S[r];

means for linking the paired data (r, j) stored by the storing means to paired data (r', j') if r'<r and j'<j where the paired data (r', j') is one stored in an array element data[k−1]; and means for obtaining a longest common subsequence between the first and the second sequences and occurrence positions of the longest common subsequence in the first and the second sequence by tracing the link formed by the linking means.

In accordance with the present invention there is provided an apparatus for analyzing three-dimensional structures including a first structure expressed by three-dimensional coordinates of elements belonging to a first point set and a second structure expressed by three-dimensional coordinates of elements belonging to a second point set, comprising:

means for generating a combination of correspondence satisfying a restriction condition between the elements belonging to the first point set and the elements belonging to the second point set from among all candidates for the combination of correspondence; and means for calculating a root mean square distance between the elements corresponding in the combination of correspondence generated by the generating means.

In accordance with the present invention there is provided an apparatus for analyzing three-dimensional structures including a first structure expressed by three-dimensional coordinates of elements belonging to a first point set and a second structure expressed by three-dimensional coordinates of elements belonging to a second point set, comprising the steps of:

means for dividing the second point set into a plurality of subsets having a size that is determined by the size of the first point set;

means for generating a combination of correspondence satisfying a restriction condition between the elements belonging to the first point set and the elements belonging to each of the subsets of the second point set from among all candidates for the combination of correspondence; and means for calculating a root mean square distance between the elements corresponding in the combination of correspondence generated by the generating means.

In accordance with the present invention there is also provided an apparatus for analyzing three-dimensional structures including a first structure expressed by three-dimensional coordinates of elements belonging to a first point set and a second structure expressed by three-dimensional coordinates of elements belonging to a second point set, comprising:

means for dividing the first point set and the second point set into first subsets and second subsets, respectively, according to a secondary structure exhibited by the three-dimensional coordinates of the elements of the first and the second point sets;

means for generating a combination of correspondence satisfying a first restriction condition between the first subsets and the second subsets from among candidates for the combination of correspondence;

means for determining an optimum correspondence between the elements belonging to each pair of subsets corresponding in the combination of correspondence generated in the generating means, and means for calculating a root mean square distance between all of the elements corresponding in the optimum correspondence.

BRIEF DESCRIPTION OF THE DRAWINGS

FIG. 6 is a diagram explaining an example of the operation of the LCS detection unit;

FIG. 10 is a diagram showing an example of output results of the gene information survey apparatus;

FIG. 11 is a diagram showing another example of output results of the apparatus;

FIG. 12 is a diagram showing another example of output results of the apparatus;

FIGS. 14A and 14B are diagrams showing tree structures expressing candidates for a combination of correspondence between elements of two nonordered point sets;

FIGS. 16A and 16B are diagrams showing tree structures expressing candidates for a combination of correspondence between elements of two ordered point sets;

FIGS. 23A and 23B are diagrams showing amino acid sequences of calmodulin and troponin C, respectively;

FIG. 25 is a diagram showing an example of output results of the device of FIG. 22;

FIG. 26 is a diagram showing another example of output results of the device of FIG. 22;

FIG. 29 is a diagram showing an example of output results of the device of FIG. 27;

FIGS. 32A and 32B are diagrams showing linear structures and non-linear structures, respectively;

FIG. 33 is a diagram explaining the division of a point set B into subsets according to the number of elements belonging to a point set A;

FIGS. 38A and 38B are diagrams showing amino acid sequences of trypsin and elastase, respectively;

FIGS. 39A and 39B are diagrams showing retrieval results of three-dimensional structures;

FIG. 44 is a diagram showing the results of the division of a point set into subsets according to secondary structures;

DESCRIPTION OF THE PREFERRED EMBODIMENTS

Analysis of one-dimensional sequences of molecules

Figure 1:
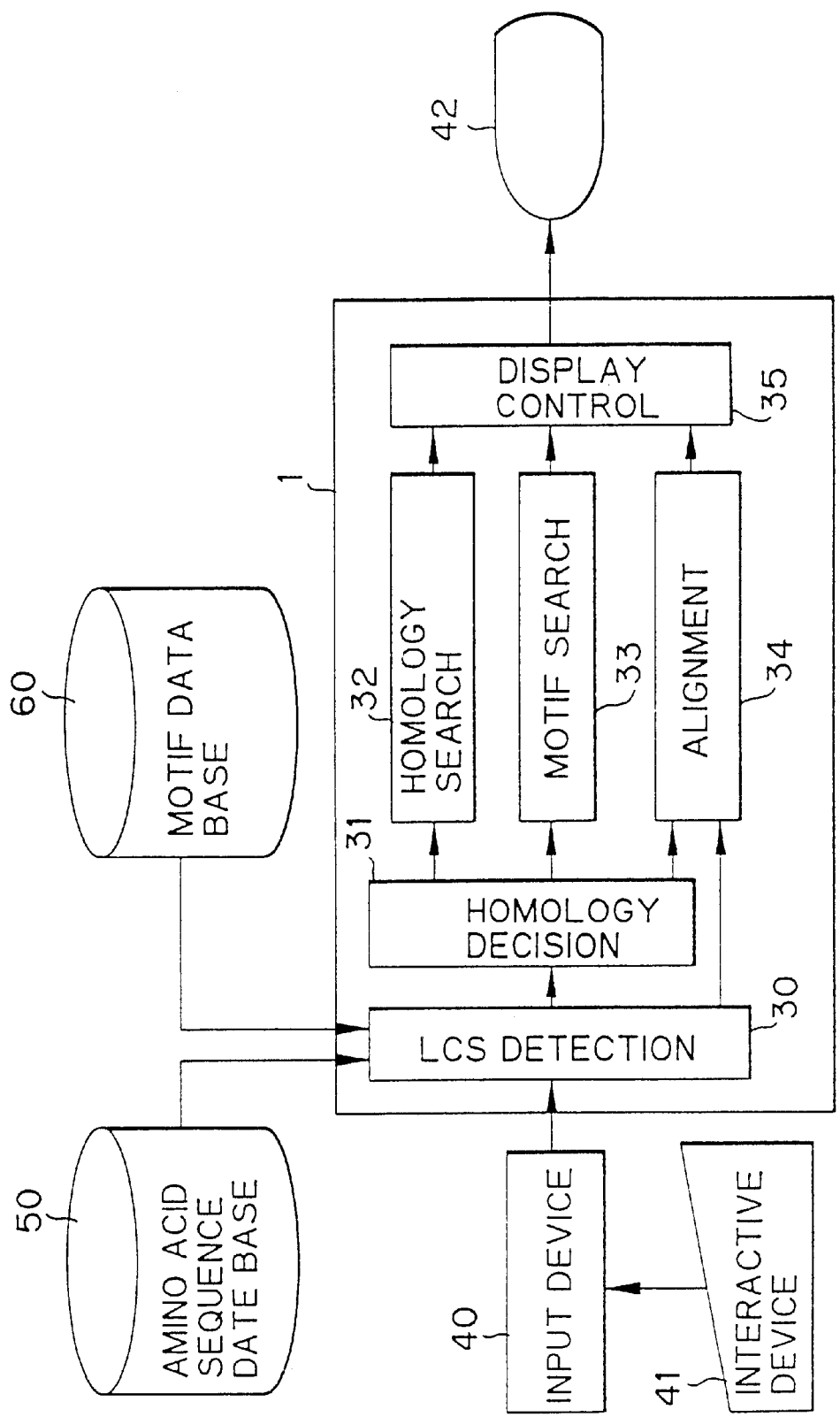
FIG. 1 is a block diagram showing a construction of a gene information survey apparatus according to an embodiment of the present invention.

FIG. 1 shows a gene information survey apparatus 1 according to an embodiment of the invention. In FIG. 1, the reference numeral 40 denotes input device connected to the gene information survey apparatus 1; the reference numeral 41 denotes an interactive device such as a keyboard and a mouse provided in the input device 40; the reference numeral 42 denotes a display device connected to the gene information survey apparatus 1; the reference numeral 50 denotes an amino acid sequence data base for storing amino acid sequence information expressed by character sequences; and the reference numeral 60 denotes a motif data base for storing motif sequence information expressed by a character sequence.

The gene information survey apparatus 1 of this embodiment includes an LCS detection unit 30, a homology decision unit 31, a homology search unit 32, a motif seach unit 33, an alignment unit 34, and a display control unit 35.

The LCS detection unit 30 determines an LCS (Longest Common Subsequence), the length of LCS, and an occurrence position of the LCS between a character sequence expressing an amino acid sequence input from the input device 40 and a character sequence expressing an amino acid sequence taken from the amino acid sequence data base 50 or motif data base 60. The LCS is the longest subsequence among those which commonly occur continuously or intermittently in both character sequences, and the length of LCS is the number of characters constituting the LCS.

The homology decision unit 31 determines the analogy between the two amino acid sequences surveyed by the LCS detection unit 30 based on the detection result of the LCS detection unit 30. A homology search unit 32 seaches the amino acid sequence data base 50 for an amino acid sequence similar to the amino acid sequence input from the input device 40 based on the decision result of the homology decision unit 31. The motif search unit 33 searches the motif data base 60 for a motif sequence similar to the amino acid sequence input from the input device 40 based on the detection result of the LCS detection unit 30. The alignment unit 34 aligns the character sequence of the amino acid sequence input from the input device 40 with the character sequence of the amino acid sequence given from the amino acid sequence data base 50 or motif data base 60 based on the detection result of the LCS detection unit 30. The display control unit 35 displays the processing results of the respective processing units in the display device 42.

Figure 2:
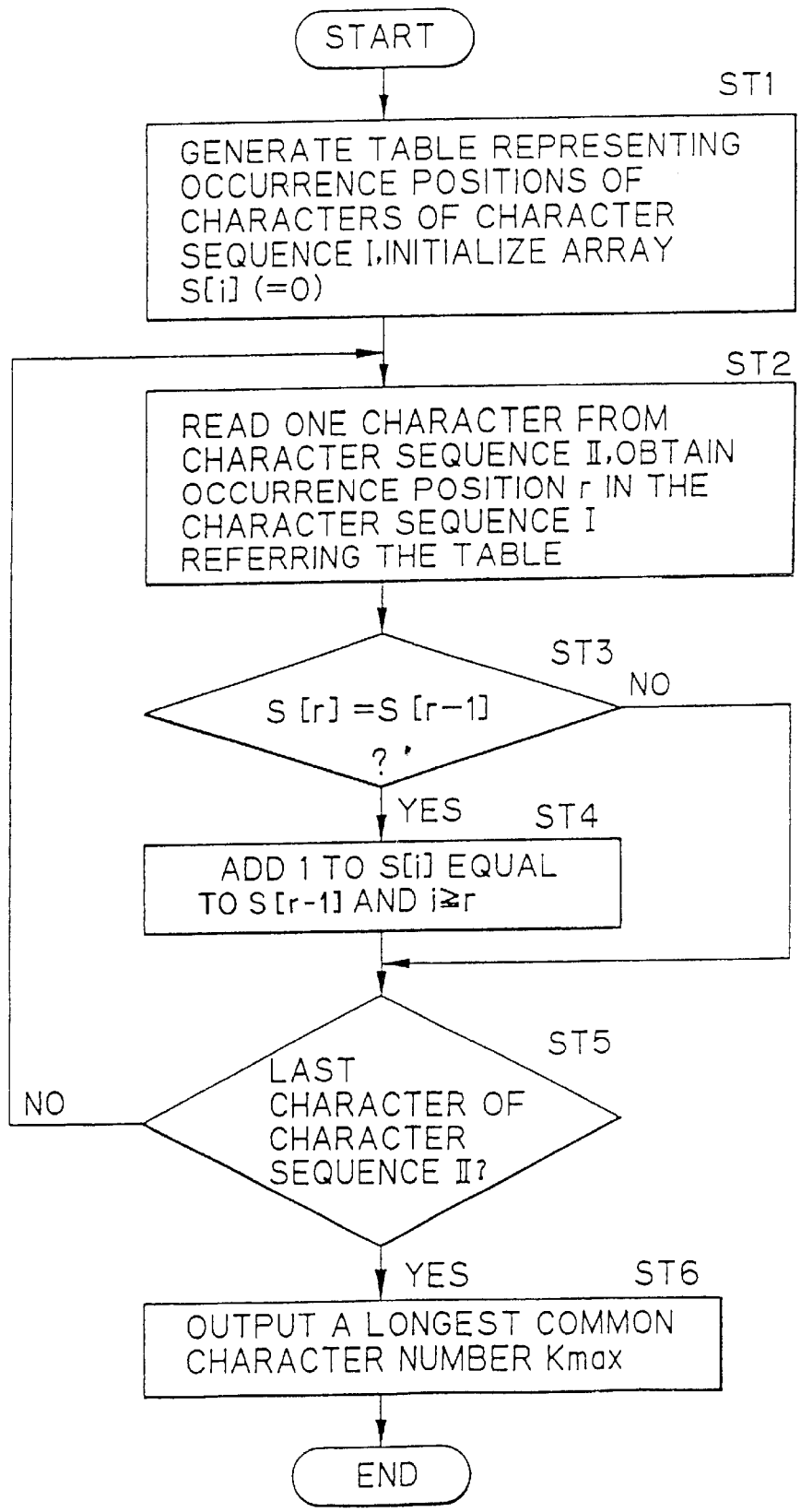
FIG. 2 is a flowchart showing a process for detecting a longest common character number in a LCS detection unit of FIG. 1.
Figure 3:
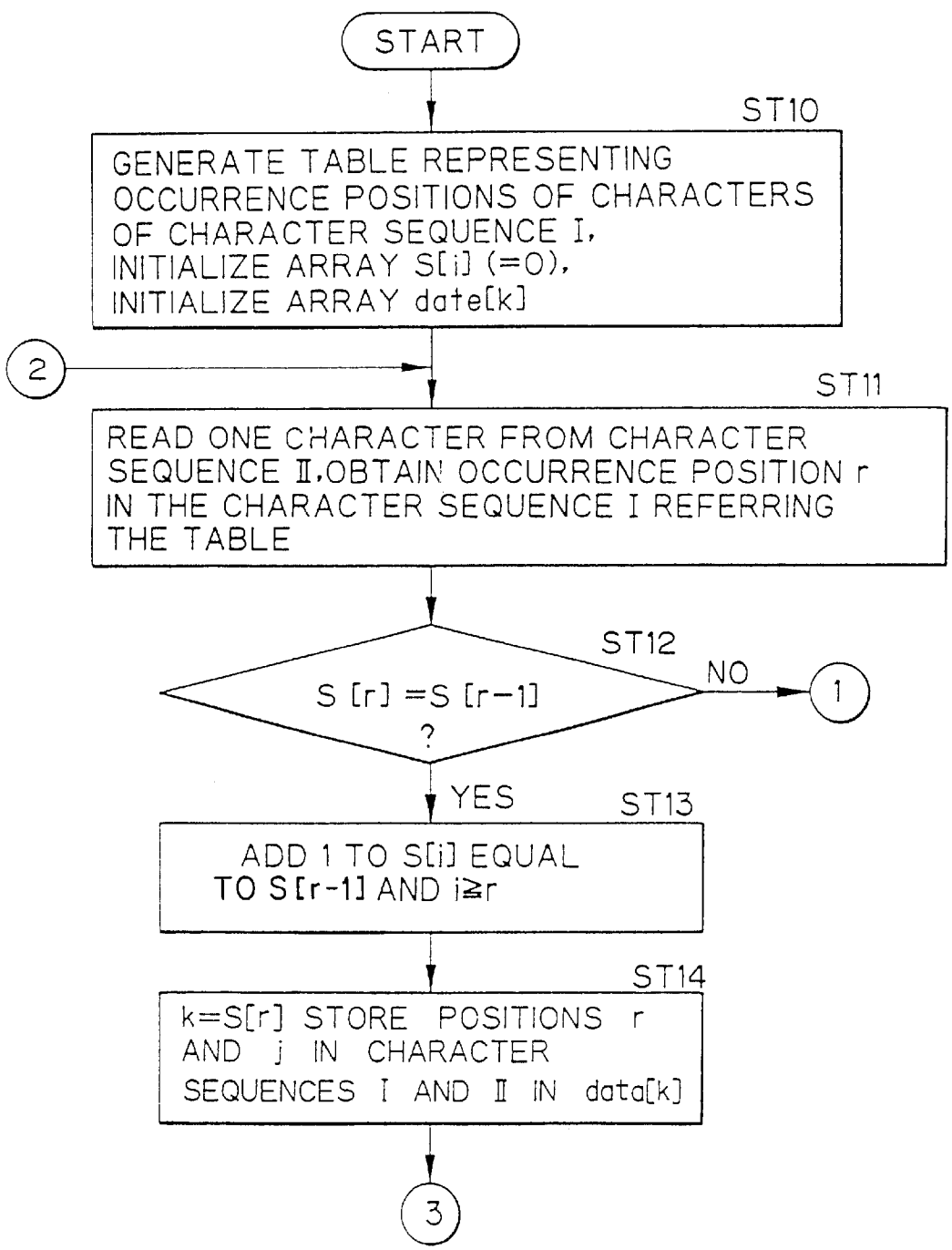
FIGS. 3 and 4 are flowcharts showing a process for detecting an LCS and occurrence positions thereof in the LCS detection unit.
Figure 4:
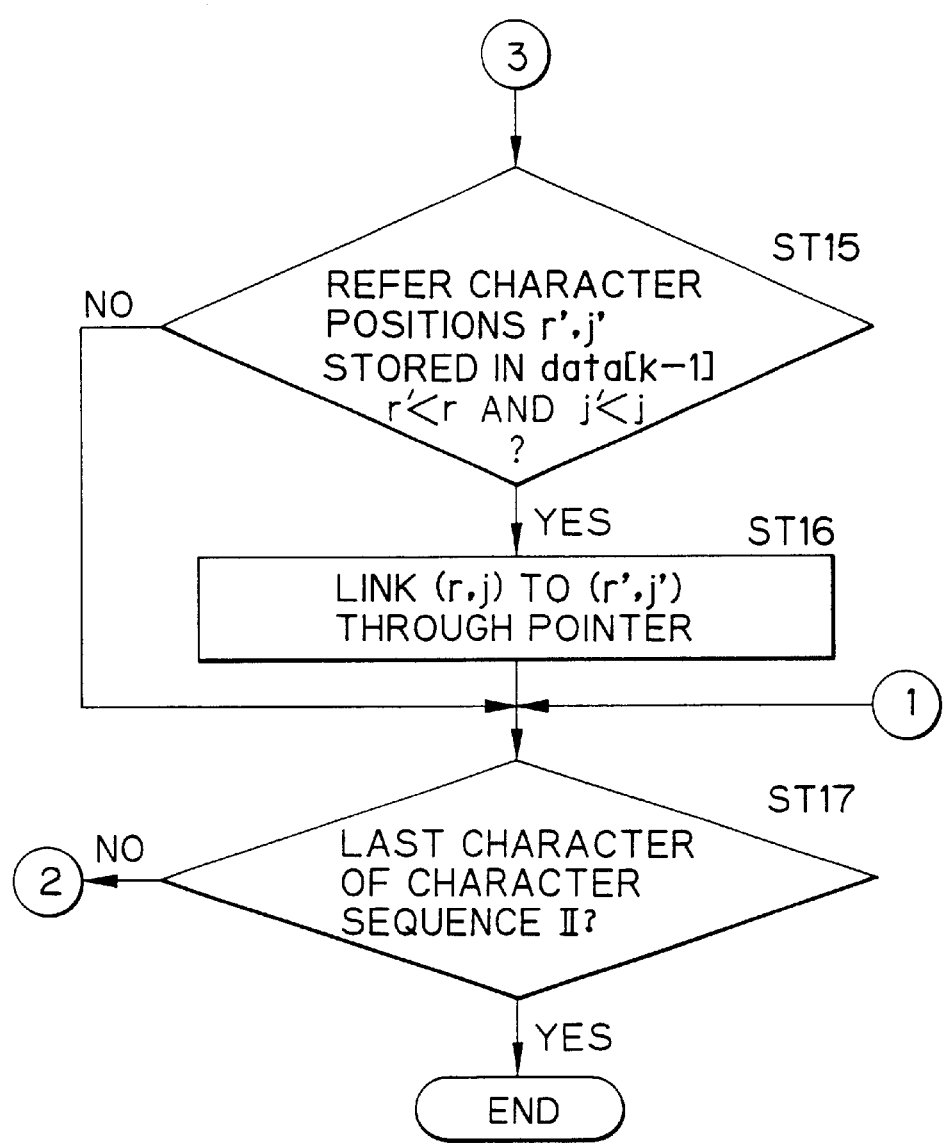

A processing carried out by the LCS detection unit 30 in accordance with processing flows shown in FIGS. 2 to 4 will be described in detail. The processing flow shown in FIG. 2 is carried out to detect the length of LCS between the two amino acid sequences to be surveyed. The processing flow shown in FIGS. 3 and 4 is carried out to detect the longest common subsequence (LCS) between the two amino acid sequences to be surveyed and the occurrence position thereof.

In detecting the length of LCS between the amino acid sequences expressed by a character sequence I and a character sequence II, the LCS detection unit 30 reads the characters individually from the character sequence I and generates an occurrence table indicative of the occurrence positions of the respective characters in the character sequence I in Step 1 as shown in the processing flow of FIG. 2.

Figure 5:
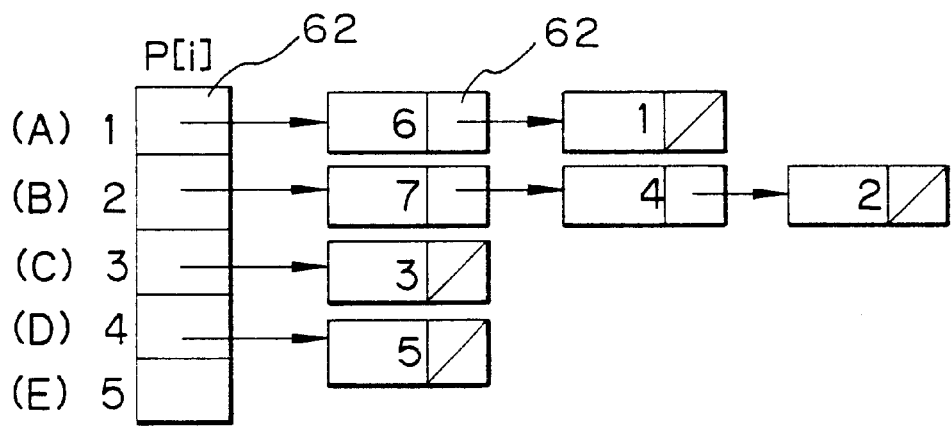
FIG. 5 is a diagram of an example of the table of occurrence positions generated in the LCS detection unit.

This occurrence table is generated, for example, by linking array elements P[1] to P[26] corresponding to alphabets A to Z with data of the occurrence positions of the respective characters by pointers 62, as shown in FIG. 5. For instance, in the case where the amino acid sequence of the character sequence I is expressed as "ABCBDAB," the occurrence table is generated such that "A" occurs in the sixth and first places; "B" occurs in the seventh, fourth, and second places; "C" occurs in the third place; and "D" occurs in the fifth place. In Step 1, an array S[i] having the same size as the character sequence I, which is used in the subsequent processing, is initialized and a zero value is set in each entry.

In Step 2, the characters are successively read from the character sequence II and the occurrence positions r of these characters in the character sequence I is specified with reference to the occurrence table generated in Step 1. Subsequently, in Step 3, it is determined whether an entry data of S[r], which is in the r-th place of the array S[i], is equal to an entry data of S[r−1], which is in the (r−1)th place thereof.

If it is determined that S[r]=S[r−1] in Step 3, Step 4 follows in which "1" is added to S[i] where i≧r and whose entry data is equal to that of S[r−1]. Subsequently in Step 5, it is determined whether the processing has been completed up to the last character of the character sequence II. If the determination result is in the negative in Step 5, this routine returns to Step 2. On the other hand, if it is determined that S[r]≠S[r−1] in Step 3, this routine proceeds to Step 5 immediately without executing the additional processing in Step 4.

In the case where the characters of the character sequence II read in Step 2 occur in the character sequence I a plurality of times, the processings of Steps 3 and 4 are repeated in decreasing order of the occurrence positions r.

If it is determined that the processing has been completed up to the last character of the character sequence II, this routine proceeds to Step 6 in which an entry data Kmax of a last element S[m] of the array S[i] is output as the length of LCS.

Figure 6:
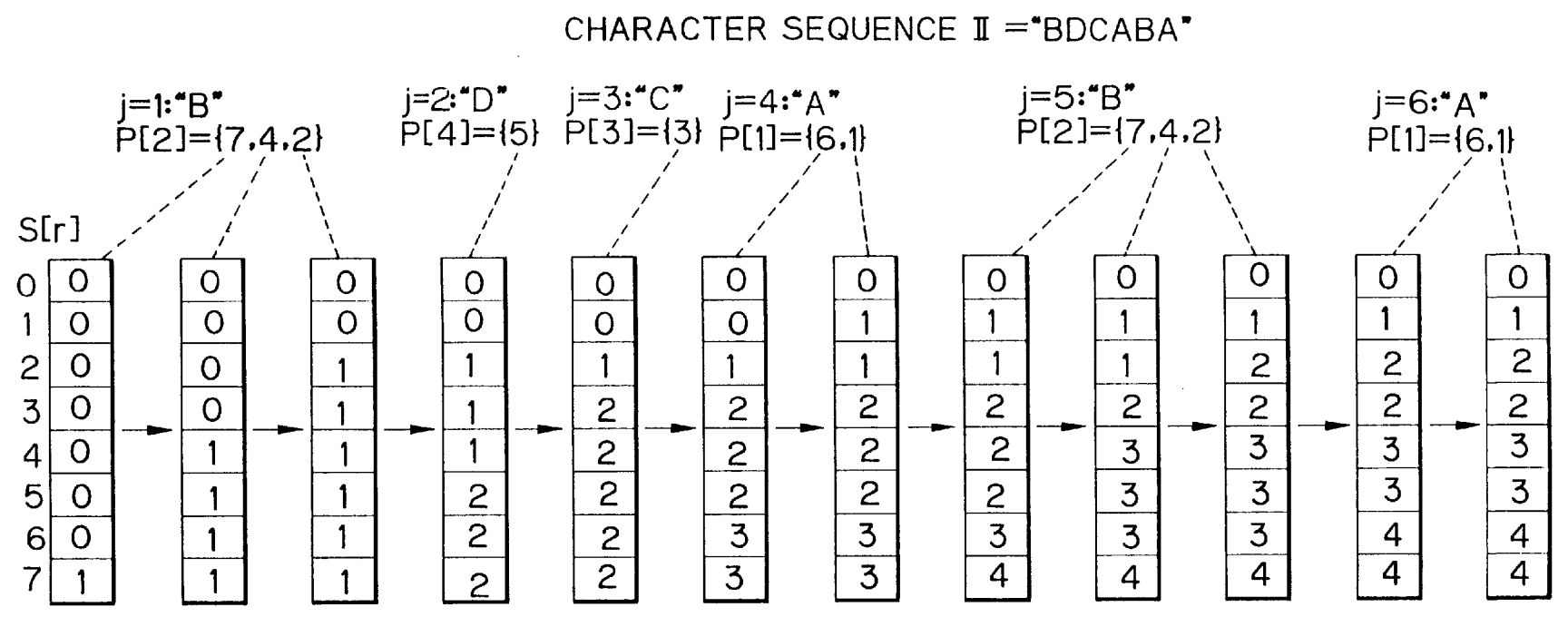

In executing the above processing flow, for example, in the case where the amino acid sequence of the character sequence I is expressed as "ABCBDAB" and that of the character sequence II is expressed as "BDCABA," "r=7, 4, 2" is specified from a list following the array element P[2] out of the occurrence table shown in FIG. 5 in accordance with the reading of the first character B (j=1) of the character sequence II, and the entry data of the array S[i] is renewed as shown sequentially from the left in FIG. 6. "r=5" is specified from the occurrence table shown in FIG. 5 in accordance with the reading of the second character D (j=2) of the character sequence II, and the entry data of the array S[i] is renewed as shown in FIG. 6. "r=3" is specified in accordance with the reading of the third character C (j=3) of the character sequence II, and the entry data of the sequence S[i] is renewed as shown in FIG. 6. "r=6, 1" is specified in accordance with the reading of the fourth character A (j=4) of the character sequence II, and the entry data of the sequence S[i] is renewed as shown in FIG. 6. It should be noted that the respective entry values of S[i] set in this manner give the length of LCS between a character subsequence consisting of the first to i-th characters of the character sequence I and the character subsequence consisting of the first to j-th characters of the character sequence II after the j-th character of the character sequence II is processed.

Thereafter, "r=7, 4, 2" is specified from the occurrence table shown in FIG. 5 in accordance with the reading of the fifth character B of the character sequence II, and the entry data of the array S[i] is renewed as shown in FIG. 6. "r=6, 1" is specified from the occurrence table shown in FIG. 5 in accordance with the reading of the sixth character A of the character sequence II, and the entry data of the sequence S[i] is renewed as shown in FIG. 6. Lastly, the length of LCS "4" is obtained in S[7]. It should be noted that the array S[i] shown in FIG. 6 additionally includes S[0] for the sake of convenience, and therefore has a size that is larger than the length of the character sequence I (=7) by one.

The processing to determine the longest common subsequence between the two amino acid sequences to be surveyed and the occurrence position thereof will be described with reference to FIGS. 3 and 4.

The LCS detection unit 30 successively reads the characters from the character sequence I and generates an occurrence table indicative of the occurrence positions of the respective characters in the character sequence I in Step 10 as shown in the processing flow of FIG. 3 in detecting the longest common subsequence between the amino acid sequences expressed by the character sequences I and II and the occurrence position thereof. In other words, the occurrence table described with reference to FIG. 5 is generated. In Step 10, an array S[i] having the same size as the character sequence I, which is used in the subsequent processing, is initialized and a zero value is set in each entry. Further, an array data[k] having the size corresponding to the length of LCS is initialized and the respective entries are set so as not to point to anything.

In Step 11, one character (j-th character) is read from the character sequence II, and the occurrence position r of this character in the character sequence I is specified with reference to the occurrence table generated in Step 10. Subsequently, in Step 12, it is determined whether an entry data of S[r], which is in the r-th place of the array S[i], is equal to an entry data of S[r-1], which is in the (r-1)th place of the sequence S[i]. If it is determined that S[r]=S[r-1] in Step 12, Step 13 follows in which "1" is added to S[i] where i≧r and whose entry data is equal to that of S[r-1]. On the other hand, if it is determined that S[r]≠S[r-1] in Step 12, this routine proceeds to Step 17 of the processing flow of FIG. 5 without executing the additional processing in Step 13. In the case where the characters of the character sequence II read in Step 11 occur in the character sequence I a plurality of times, the processings of Steps 12 and 13 are repeated in decreasing order of the occurrence positions r.

In this way, the LCS detection unit 30 also executes the processing so as to detect the length of LCS described in the processing flow of FIG. 2 in detecting the longest common subsequence.

After execution of the processing of Step 13, paired data (r, j) including the occurrence position r in the character sequence I and the occurrence position j in the character sequence II is stored in the array data[k] in Step 14 in accordance with the length of LCS k, which is obtained in entry data of S[r]. In fact, the paired data (r, j) is stored at the last of the list linked to the array data[k]. If the array S[i] is unchanged from the one in the preceding processing cycle, the above storing processing is not executed.

Subsequently, this routine proceeds to the processing flow of FIG. 4 and, in Step 15, it is determined whether relationships r'<r, j'<j are satisfied with respect to each of the character positions r', j' stored in the data[k-1]. Since the character positions cannot be reversed in the subsequences, the above relationship must be satisfied along a subsequence. Therefore, the data (r, j) is linked to the data (r', j')

in Step 16; only when the above relationship is satisfactory. In subsequent Step 17, it is determined whether the processing has been completed up to the last character of the character sequence II. If the determination result is in the negative in Step 17, this routine returns to Step 11 of the processing flow shown in FIG. 3. On the other hand, if it is determined that the above relational expressions are not satisfied in Step 15, this routine proceeds to Step 17 without executing the processing of Step 16.

If it is determined that the processing has been completed up to the last character of the character sequence II in Step 17, this processing flow ends. The longest common subsequence and the occurrence position thereof are determined by tracing back the link set in Step 16, as will be described in detail later.

An example of the processing shown in FIGS. 3 and 4 will be described with respect to a case where a first amino acid sequence is expressed by the character sequence I "ABCBDAB" and a second amino acid sequence is expressed by the character sequence II "BDCABA" similar to the aforementioned example.

Figure 7:
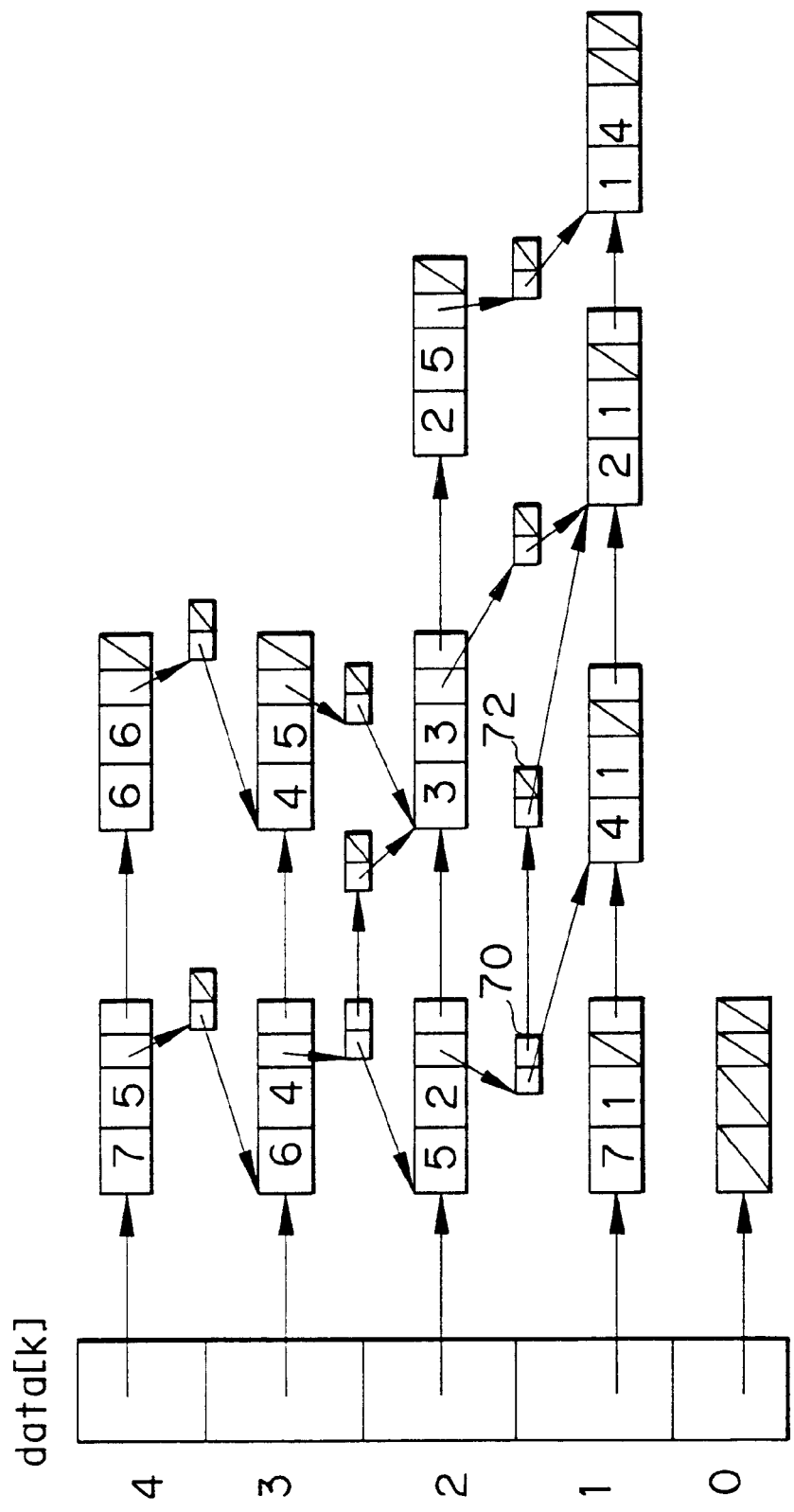
FIG. 7 is a diagram showing a linked data structure generated in the LCS detection unit.

As shown at a left end of FIG. 6, since r=7, j=1, and k=1 when S[r] is first renewed in Step 13 of FIG. 3, data (7, 1) is stored in a data[1] by being linked thereto in Step 14 of FIG. 3 as shown in FIG. 7. Thereafter, data (4, 1), (2, 1) are stored.

Since nothing is stored in a data[0] set, for the sake of convenience, the processing of Step 16 is not applied thereto. Since S[r] is renewed when r=5, j=2, and k=2, data (5,2) is stored in a data[2] as shown in FIG. 7. In Step 15, the relationships r'<r and j'<j are satisfied for the data (4, 1) and (2, 1) among the data (7, 1), (4, 1), and (2, 1) stored in the data[1]. Accordingly, the data (5, 2) is linked to the data (4, 1) and (2, 1) through pointers 70, 72 shown in FIG. 7 in Step 16. By repeating the aforementioned processing, a linked list shown in FIG. 7 is generated. As shown at the right side of FIG. 6, the data (1, 6) is not stored in the data[k] since S[r] is unchanged when r=1 and j=6.

The longest common subsequence and the occurrence position thereof are determined by tracing back the pointers of the character position information stored in the data[k]. If this is explained more specifically using the example of FIG. 7, the link "(7, 5) of the data[4]—>(6, 4) of the data[3]—>(5, 2) of the data[2]—>(4, 1) of the data [1]" is traced and arranged in reverse order, thereby determining the longest common subsequence BDAB and the occurrence positions in the character sequences I and II. Also, the longest common subsequence BDAB and the occurrence positions thereof in the character sequences I and II are determined from the link "(7, 5) of the data[4]—>(6, 4) of the data[3]—>(5, 2) of the data[2]—>(2, 1) of the data [1]". Further, the longest common subsequence BCAB and the occurrence positions thereof in the character sequences I and II are determined from the link "(7, 5) of the data[4]—>(6, 4) of the data[3]—>(3, 3) of the data[2]—>(2, 1) of the data [1 ]". Moreover, the longest common subsequence BCBA and the occurrence positions thereof in the character sequences I and II are determined from the link "(6, 6) of the data[4]—>(4, 5) of the data[3]—>(3, 3) of the data[2]—>(2, 1) of the data [1]".

Figure 8:
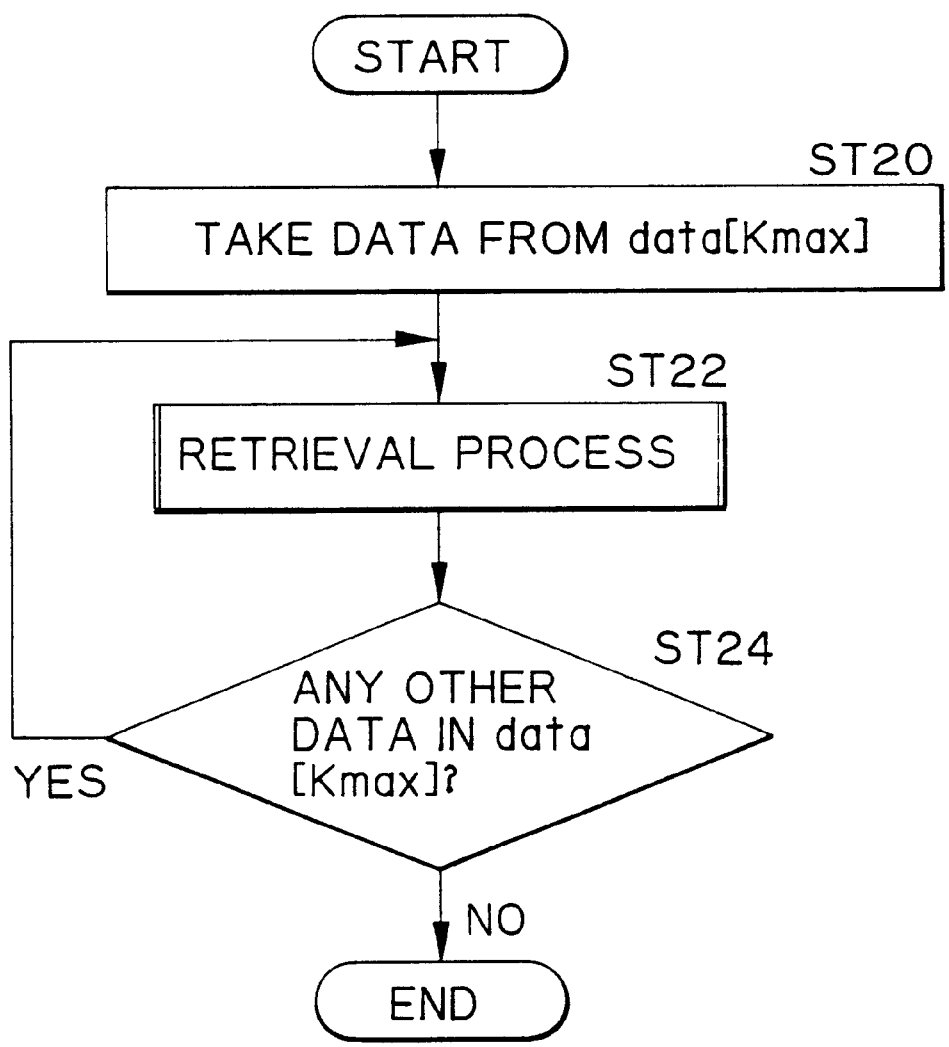
FIG. 8 is a flowchart showing the linked data structure tracing operation.
Figure 9:
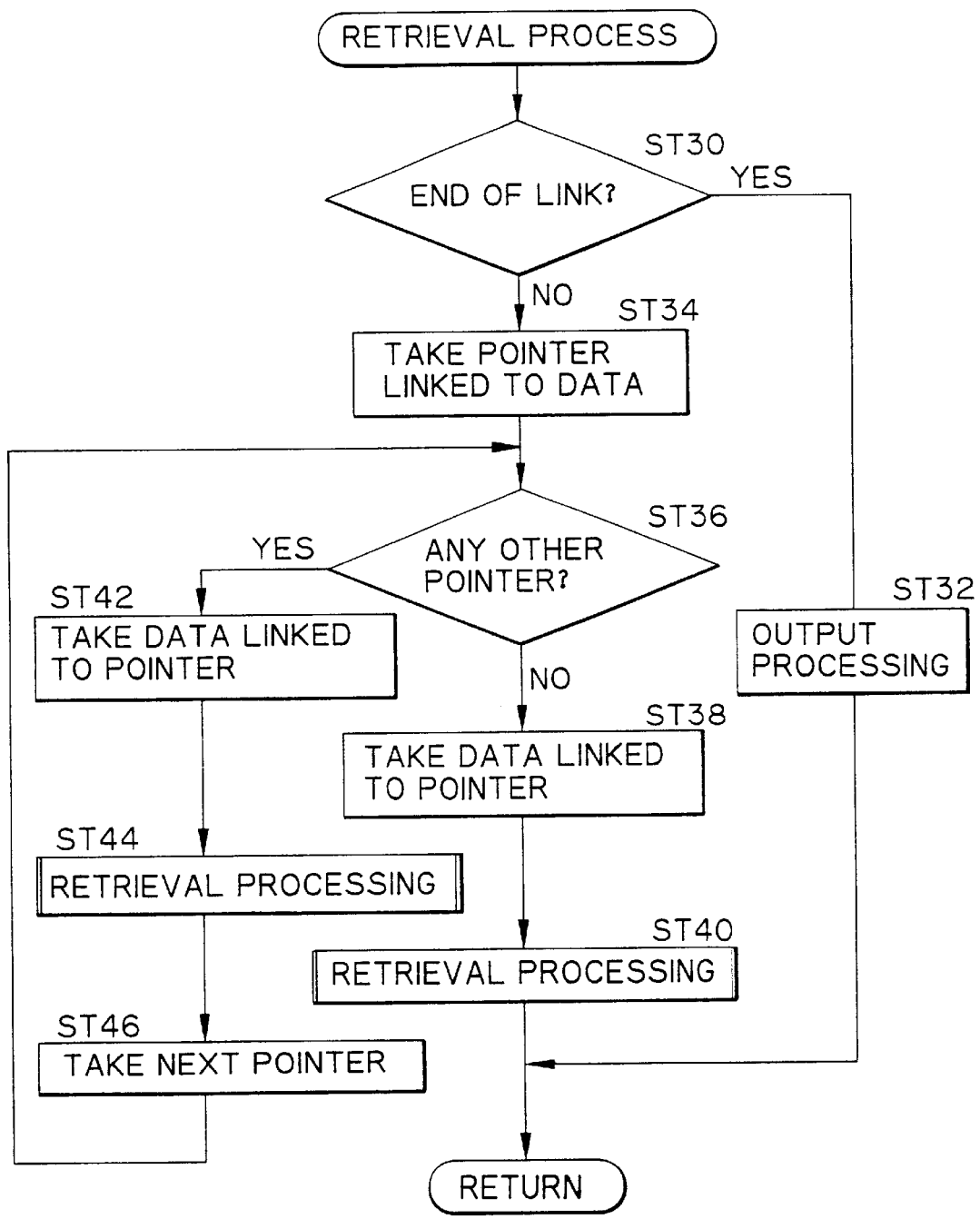
FIG. 9 is a flowchart showing an operation of a retrieval process called in the tracing operation.

FIGS. 8 and 9 shows a processing flow that is executed when the LCS detection unit 30 specifies the longest common subsequence by tracing this link.

In Step 20 of FIG. 8, leading data of the link of the LCS is taken from a data[Kmax]. In Step 22, a retrieval processing subroutine is called to trace and output all the data of the link following the leading data. In Step 24, it is decided whether other data still remains in the data[Kmax]. This routine ends if the processing is completed, while returning to Step 22 if any data remains. This routine is continued until the links of all the LCS are completed. The retrieval processing subroutine shown in FIG. 9 is a recursive routine. In Step 30, it is determined whether the taken data is an end terminal of the link of the LCS by checking the data taken when this subroutine is called. If the determination result is in the affirmative in Step 30, this subroutine returns to the main routine shown in FIG. 8 after executing an output processing in Step 32. If the determination result is in the negative in Step 30, the pointer linked to this data is taken out in Step 34. In Step 36, by checking the content of this pointer, it is determined whether there exists any pointer to be linked to other data. If no other pointer exists, the data linked to the above pointer is taken out in Step 38, and the next link is traced by calling this subroutine recursively in Step 40. If other data exist in Step 36, the data linked to the pointer is taken out in Step 42 and the next link is traced by calling the subroutine recursively. Upon completion of the processing of Step 44, the next pointer is taken out in Step 46 and this subroutine returns to Step 36, thereby executing processing for the next branch.

By executing the above processing, for example, the data (7, 5), (6, 4), (5, 2), and (4,1) are sequentially taken out in the example shown in FIG. 7, the LCS "BDAB" and the occurrence position thereof are output. Then, (2, 1) is taken out to obtain the data (7, 5), (6, 4), (5, 2) and (2, 1), and the LCS "BDAB" and the occurrence position thereof are output. Further, the data (7, 5), (6, 4), (3, 3), and (2, 1) are obtained and the LCS "BCAB" is output. Moreover, the data (6, 6), (4, 5), (3, 3), and (2, 1) are obtained and the LCS "BCBA" is output. In this way, all the LCS are output.

A processing, such that the respective processing units 31 to 35 of the gene information survey apparatus 1 shown in FIG. 1 execute upon receipt of the length of LCS, the longest common subsequences, and their occurrence positions detected by the LCS detection unit 30, will be described.

When the LCS detection unit 30 decides the length of LCS between the character sequence of the amino acid sequence input from the input device 40 (hereinafter referred to as an input amino acid sequence) and the character sequence of the amino acid sequence given from the amino acid sequence data base 50 or the motif data base 60, the homology decision unit 31 determines the ratio of the length of LCS to the length of the character sequence of the input amino acid sequence. In the case where this ratio is greater than a predetermined reference value, the input amino acid sequence is determined to be homologous with the amino acid sequence given from the amino acid sequence data base 50 or the motif data base 60. In the case where this ratio is smaller than the predetermined reference value, the input amino acid sequence is determined not to be homologous with the amino acid sequence given from the data base 50 or 60.

Based on the decision result of the homology decision unit 31, the homology search unit 32 seaches the amino acid sequence data base 50 for an amino acid sequence being homologous with the input amino acid sequence. In the case where the two amino acid sequences are homologous, the ratio calculated by the homology decision unit 31 and the longest common subsequence determined by the LCS detection unit 30 are displayed in the display device 42 through the display control unit 35.

FIG. 10 shows an example of this display. The display example displays a processing result of two amino acid sequences: human cytochrome c and bacteria cytochrome c. The longest common subsequences are displayed in accordance with a display mode indicative of the interval at which they are arranged in the two amino acid sequences. More specifically, by adopting a mode of displaying "GD {x 3, 3} G {x 0, 1} K {x 0, 2} . . . ", the longest common subsequences are displayed as follows. In the human cytochrome c, "GD" is followed by three characters that do not coincide, followed by "G", which is immediately followed by "K". On the other hand, in the bacteria cytochrome c, "GD" is followed by three characters that do not coincide, followed by "G", which is followed by one character that does not coincide. "K" follows immediately thereafter.

The motif search unit 33 first searches the motif data base 60 for the motif sequence being homologous with the input amino acid sequence based on the decision result of the homology decision unit 31, and then decides whether the homologous motif sequence is a true motif sequence included in the input amino acid sequence in accordance with the longest common subsequences determined by the LCS detection unit 30 and the length of the character sequence between the longest common subsequences. For instance, it is determined whether the input amino acid sequence includes a motif sequence called leucine zipper in which "L" is followed by unspecified six characters, which is followed again by "L" and a total of 5 "L" are included together with the six unspecified characters. In the case where the input amino acid sequence includes the motif sequence, the motif search unit 33 displays the input amino acid sequence and the motif sequence in the display device 42 through the display control unit 35. FIG. 11 shows a display example of a rat egg cell potassium channel including a motif called the leucine zipper.

Upon receipt of the longest common subsequences and their occurrence positions that the LCS detection unit 30 detects, the alignment unit 34 aligns the input amino acid sequence and the amino acid sequence given from the amino acid sequence data base 50 and the motif data base 60 so as to relate the longest common subsequence in one amino acid sequence to that in the other, and displays the aligned amino acid sequences in the display device 42 through the display control unit 35. FIG. 12 shows an example of this display, which displays a processing result of two amino acid sequences: human cytochrome c and bacteria cytochrome c. The alignment processing is carried out by inserting a blank corresponding to the length of the character sequence between the positions of the subsequences.

Analysis of Three-Dimensional Structures of Molecules I

A method of partially relating elements including an atom or an atomic group in three-dimensional structures of molecules, particularly protein molecules, and comparing with each other, will be described.

Figure 13:
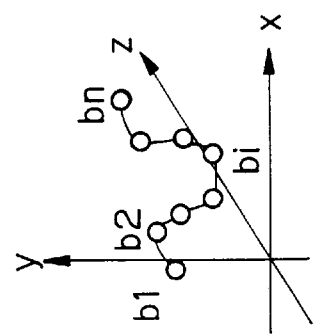
FIGS. 13A to 13D are diagrams showing the determination of correspondence of partial three-dimensional structures.
Figure 13:
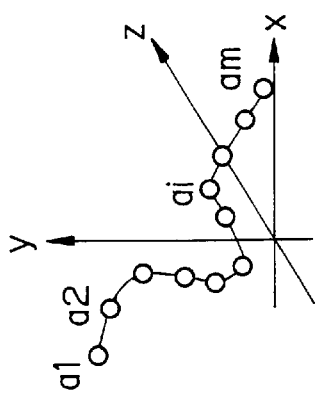
Figure 13:
Figure 13C:
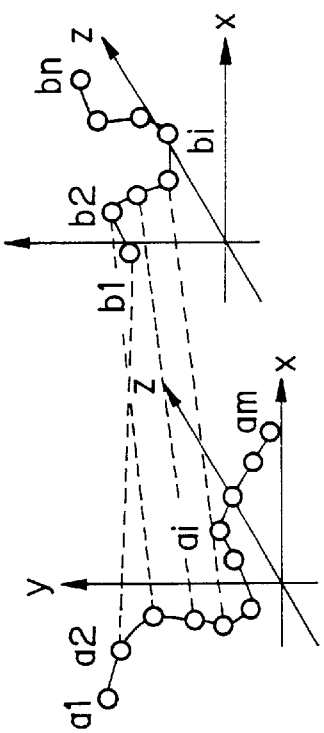

For instance, it is assumed that there are substances expressed by a point set $A=\{a_1, a_2, \ldots, a_i, \ldots, a_m\}$ as shown in FIG. 13A and a point set $B=\{b_1, b_2, \ldots, b_j, \ldots, b_n\}$ as shown in FIG. 13B. The elements constituting these substances A and B are related to each other as shown in FIG. 13C, and the substance B is rotated and moved so that the r.m.s.d value between the corresponding elements is minimized, as shown in FIG. 13D. The r.m.s.d value is obtained in the following equation wherein U denotes a rotation matrix and $w_k$ denote respective weights:

$$\text{r.m.s.d.} = \frac{\left(\sum_{k=1}^{n} (w_k(Ub_k - a_k)^2)\right)^{\frac{1}{2}}}{n}$$

A technique of obtaining the rotation and movement of the substances which minimizes the r.m.s.d value between these corresponding points is proposed by Kabsh et al. as described above, and is presently widely used.

1. Various Methods of Determining Correspondence (1) Generation of Correspondence of Point Sets that are Not Ordered The substances A and B are expressed, respectively, by the point sets A=$\{a_1, a_2, \ldots, a_i, \ldots, a_m\}$, $1 \leq i \leq m$, and the point set B=$\{b_1, b_2, \ldots, b_j, \ldots, b_n\}$, $1 \leq j \leq n$. The respective points $a_i=(x_i, y_i, z_i)$ and $b_j=(x_j, y_j, z_j)$ are expressed as a three-dimensional coordinate. In this case, the correspondence of elements between these point sets is in principle obtained by relating sequentially the points in the respective sets, and it can be accomplished to generate all combinations by creating a tree construction as shown in FIG. 14A.

FIG. 14B shows an example of correspondence in the case where a point set A includes three elements and a point set B includes four elements, i.e., the correspondence between the point set A=$\{a_1, a_2, a_3\}$ and the point set B=$\{b_1, b_2, b_3, b_4\}$. A dotted line represents generated candidates, and a solid line represents an optimum correspondence ($a_1$ and $b_2$, $a_2$ and $b_3$, $a_3$ and $b_4$) among all the generated candidates.

In this figure, nil corresponds to a case where no corresponding point exists. By using the nil, an optimum correspondence can be generated even in the case where the number of elements of one set differs from that of the other. An optimum correspondence can be generated by applying Kabsh's method to thus generated combinations, and selecting a combination whose root mean square distance value (r.m.s.d. value) is smallest.

However, using this technique it is generally impossible to effect a calculation since, for example, $n^m$ combinations are generated. Specifically, In the case of the point set A (m points) and the point set B (n points), which are not ordered, if (i) is assume to be the number of nil the number of generated combinations is expressed as follows:

$$\sum_{i=0}^{m} ({}_nP_{m-i} \times {}_mC_i) = \sum_{i=0}^{m} \frac{n!}{n-m+i} \times \frac{m!}{i!(m-i)}$$

Here, if it is assumed that n=4, m=3, the above equation is expressed as follows.

$$\sum_{i=0}^{3} ({}_4P_{3-i} \times {}_3C_i) = \sum_{i=0}^{3} \frac{4!}{(4-3+i)!} \times \frac{3!}{i!(3-i)!}$$

$$= \frac{4!}{1!} \times \frac{3!}{3!} + \frac{4!}{2!} \times \frac{3!}{1!2!} + \frac{4!}{3!} \times \frac{3!}{2!1!} + \frac{4!}{4!} \times \frac{3!}{3!}$$

$$= 24 + 36 + 12 + 1$$

$$= 73$$

In other words, 73 combinations are generated, as in the case of the point set A (3 points) and the point set B (4 points) shown in 14B. In reality, a huge number of combinations are generated since the number of points (elements) are usually far greater than these.

Accordingly, in generating correspondence between these sets, it is designed to generate an optimum combination in view of the geometric relationship within the respective sets, the threshold value condition, and the attribute of points described in detail in (4), (5), (6) below.

Figure 15:
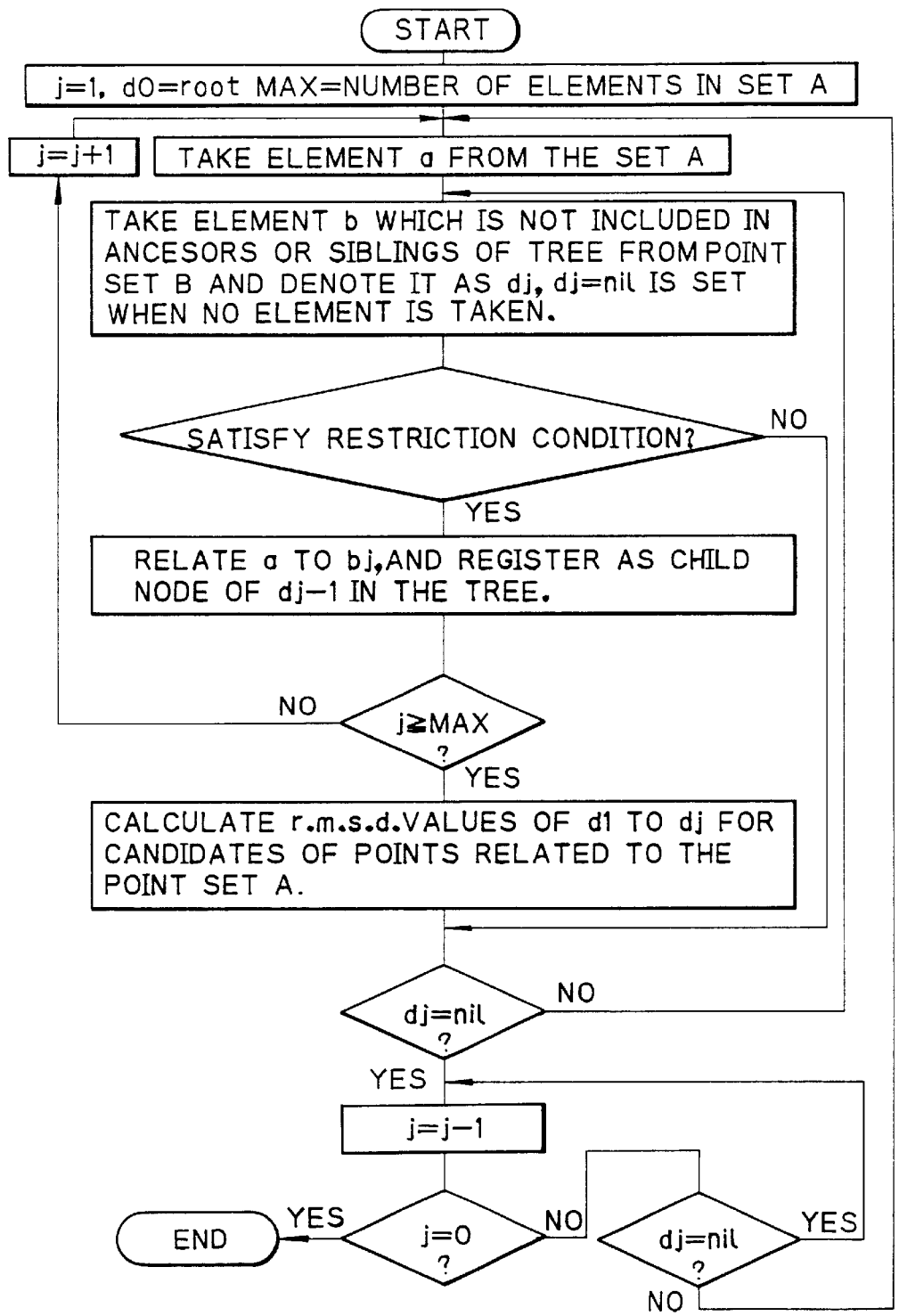
FIG. 15 is a flowchart showing an algorithm for generating a combination of correspondence between two nonordered point sets.

FIG. 15 shows an example of algorithm of generating correspondence between the point sets A and B including elements, namely points, that are not ordered.

The elements a are taken individually from the point set A, and combined with elements $b_j$, which are not included in ancestors or siblings in the tree structure yet. Then, it is determined whether this combination satisfies a restriction condition to be described later. If the combination satisfies the restriction condition, it is registered in the tree structure and the next element is related.

(2) Generation of Ordered Point Sets

The substances A and B are expressed, respectively, by the point sets A=$\{a_1, a_2, \ldots, a_i, \ldots, a_m\}$, $1 \leq i \leq m$, and the point set B=$\{b_1, b_2, \ldots, b_j, \ldots, b_n\}$, $1 \leq j \leq n$. The respective points $a_i=(x_i, y_i, z_i)$ and $b_j=(x_j, y_j, z_j)$ are expressed as a three-dimensional coordinate. In the point set A, an order relationship is established: $a_1 < a_2 < \ldots < a_i < \ldots < a_m$ (or $a_1 > a_2 > \ldots > a_i > \ldots > a_m$). Likewise, in the point set B an order relationship is established: $b_1 < b_2 < \ldots < b_j < \ldots < b_n$ (or $b_1 > b_2 > \ldots > b_j > \ldots > b_n$).

In this case, elements of these point sets are in principle related to each other in accordance with the order relationship, and all combinations can be generated by creating a tree structure shown in FIG. 16A. FIG. 16B shows an example case where the point set A includes three elements and the point set B includes four elements. In other words, FIG. 16B shows the correspondence between the ordered point set A=$\{a_1, a_2, a_3\}$ (order relationship thereof is: $a_1 < a_2 < a_3$) and the ordered point set B=$\{b_1, b_2, b_3, b_4\}$ (order relationship thereof: $b_1 < b_2 < b_3 < b_4$).

A dotted line represents generated candidates for correspondence, and a solid line represents an optimum correspondence ($a_1$ and $b_2$, $a_2$ and $b_3$, $a_3$ and $b_4$) among the generated candidates. In this figure, nil corresponds to a case where no corresponding point exists. By using the nil, an optimum correspondence can be generated even in the case where the number of elements of one set to be related differs from that of the other to be related. An optimum correspondence can be generated by applying Kabsh's method to thus generated combinations, and selecting a combination whose root mean square distance value (r.m.s.d. value) is smallest.

The number of generated combinations is expressed as follows in the case of the ordered point sets:

$$\sum_{i=0}^{m} ({}_nC_{m-i} \times {}_mC_i) = \sum_{i=0}^{m} \frac{n!}{(m-i)!(n-m+i)!} \times \frac{m!}{i!(m-i)!}$$

it is assumed that n=4, m=3, the number of combinations is as follows.

$$\sum_{i=0}^{3} ({}_4C_{3-i} \times {}_3C_i) = \sum_{i=0}^{3} \frac{4!}{(3-i)!(4-3+i)!} \times \frac{3!}{i!(3-i)!}$$

$$= \frac{4!}{3!1!} \times \frac{3!}{3!} + \frac{4!}{2!2!} \times \frac{3!}{1!2!} + \frac{4!}{1!3!} \times$$

$$\frac{3!}{2!1!} + \frac{4!}{4!} \times \frac{3!}{3!}$$

$$= 4 + 18 + 12 + 1$$

$$= 35$$

Figure 35:
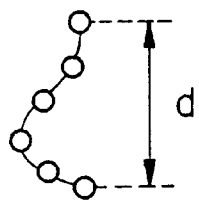
FIGS. 35A and 35B are diagrams explaining the division of a point set B into subsets according to a spatial size of a point set A.
Figure 35:
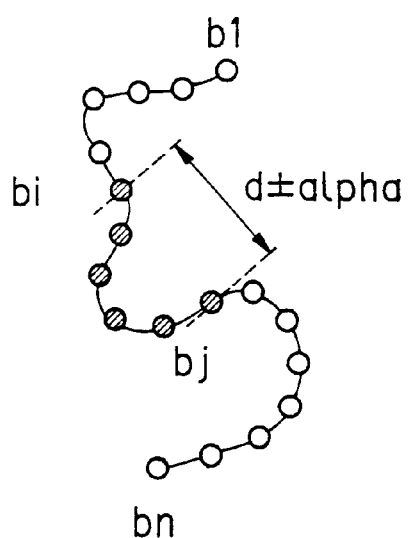

In the case of the point set A (3 points) and the point set B (4 points) as shown in FIG. 16B, 35 combinations are generated.

If the order relationship is applied to the respective elements with in the point sets in this way, the number of generated combination can be reduced greatly compared to (1). Further, in relating these sets, an optimum combination can be generated in view of the geometric relationship within the respective sets, the threshold value condition, and the attribute of points described in detail in (4), (5), (6) below.

Figure 17:
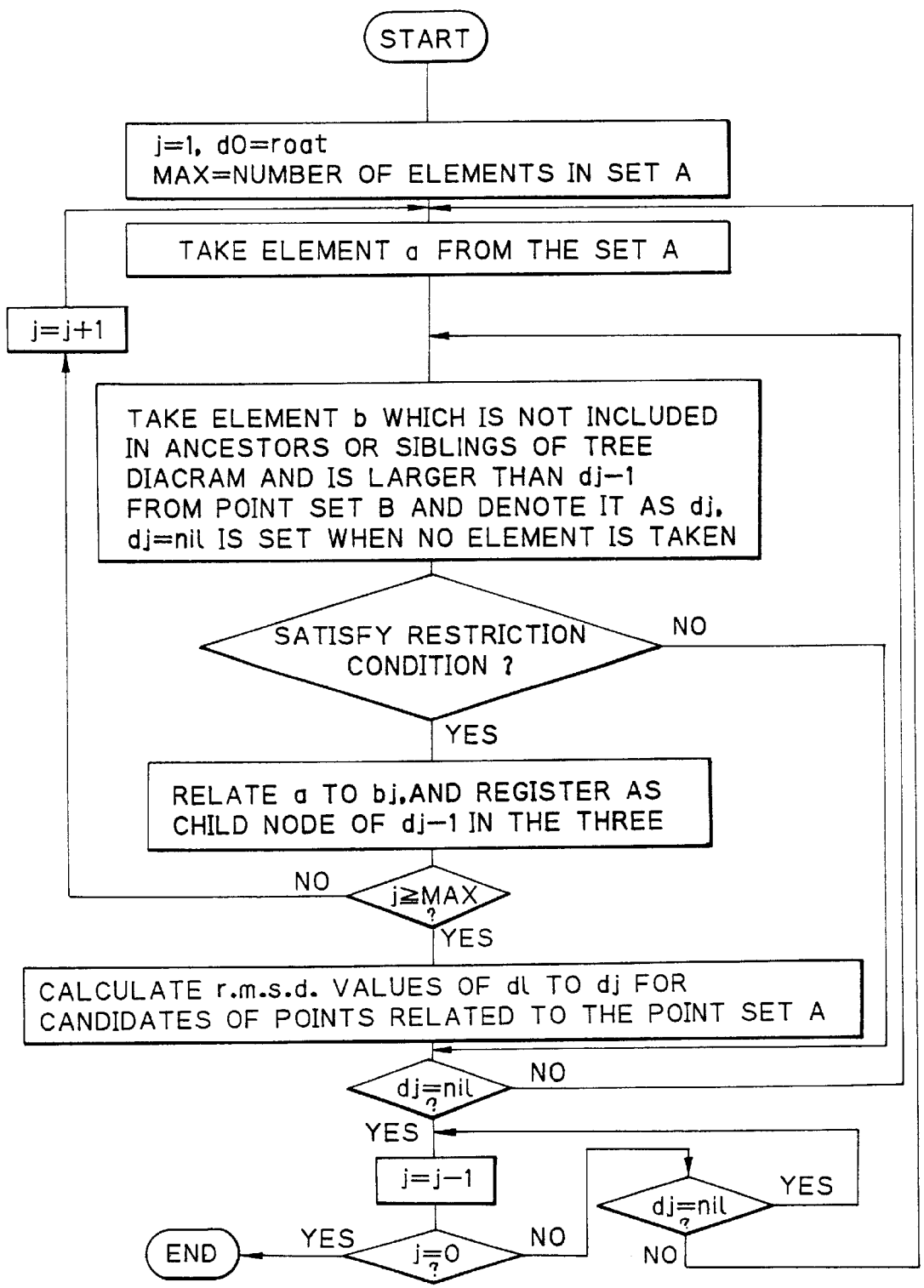
FIG. 17 is a flowchart showing an algorithm for generating a combination of correspondence between two ordered point sets.

FIG. 17 shows an example of an algorithm for relating elements of the ordered point sets A and B.

The elements a are taken individually from the point set A, and combined with elements $b_j$ which are not yet included in ancestors or siblings in the tree structure and are larger than elements of a parent node. Then, it is determined whether this combination satisfies the restriction condition. If the combination satisfies the restriction condition, it is registered in the tree structure and the next element is related.

Figure 18:
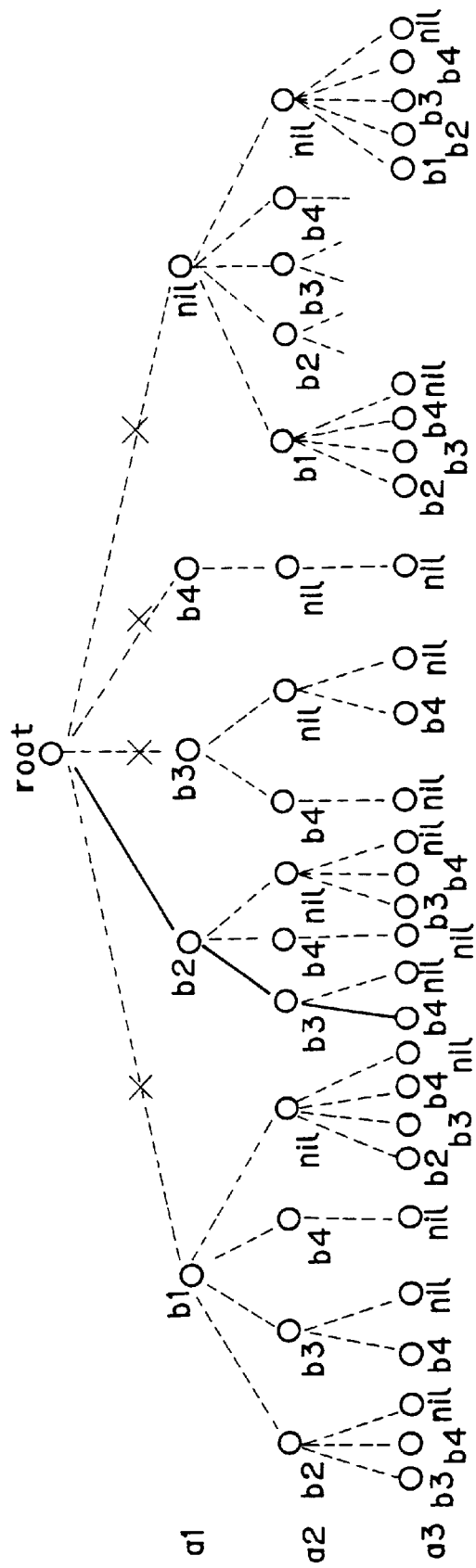
FIG. 18 is a diagram showing a tree structure expressing candidates for a combination of correspondence between elements of two ordered point sets that are partially related to each other.

(3) Generation of Correspondence of Ordered or Nonordered Point Sets that are Partially Related to Each Other In the case of (1) or (2), there are cases where pairs of points that are partially related are determined in advance. In this case, while referring to information on the elements related in advance, the remaining elements of the respective point sets are sequentially related similar to the technique (1) or (2), thereby creating a tree structure as shown in FIG. 18. In this way, all combinations can be generated.

In FIG. 18, indicated at x is a portion to be pruned based on the partial correspondence. This figure shows a correspondence in the case where the element $a_1$ of the point set A and the element $b_2$ of the point set B are related to each other in advance. Similar to (1), (2), in relating these sets, an optimum combination can be generated in view of the geometric relationship within the respective sets, the threshold value condition, and the attribute of points described in detail in (4), (5), (6) below.

(4) Refining of Candidates Based on a Geometric Relationship

Since the generation of unnecessary combinations can be prevented by generating correspondence between elements of point sets considering a geometric relationship, the points sets can be related efficiently.

(a) Refining of Candidates Based on a Distance Relationship

In relating the points set, there is a distance relationship established between s ($1 \leq s \leq m-1$, n−1) points close to an element $a_i$ within the point set A: $|a_i-a_{i-s}|$, and another distance relationship established between s points close to an element $b_j$ within the point set B: $|b_j-b_{j-s}|$. The number of candidates to be related can be reduced by selecting and relating points that will satisfy a relationship: $||a_i-a_{i-s}|-|b_j-b_{j-s}|| \leq \Delta d$ wherein $\Delta d$ denotes a permissible error range.

Figure 19:
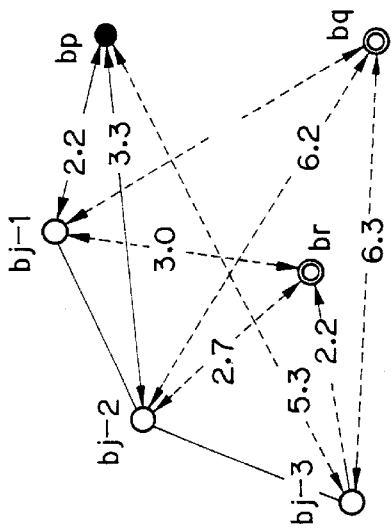
FIG. 19A and 19B are diagrams explaining the refining of candidates using a distance relationship.
Figure 19:
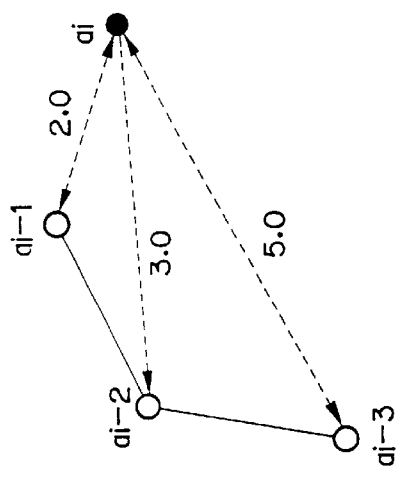

FIGS. 19A and 19B show an example using the geometric relationship in the case where the point $b_j$ of the point set B corresponding to the element $a_i$ of the point set A is selected. Each numerical value in these figures shows a distance.

As shown in FIG. 19A, there is assumed to be a distance relationship established between two (s=2) points $a_{i-1}$, $a_{i-2}$ close to the element $a_i$ of the point set A: $|a_i-a_{i-1}|=2.0$, $|a_i-a_{i-2}|=3.0$. As shown in FIG. 19B, among the elements $b_p$, $b_q$, $b_r$ of the point set B is selected such a point that a distance relationship between two elements close to this point lies within the permissible error range $\Delta d=0.5$, and this point is related. In this example, the point $b_p$ ($|b_p-b_{j-1}|=2.2$, $|b_p-b_{j-2}|=3.3$) is found to satisfy the distance relationship as a result of comparing the distance between the points as a geometric relationship, the point $b_p$ is selected as a candidate for $b_j$.

(b) Refining of Candidates Based on an Angle Relationship

In the case where the three-dimensional structures are similar to each other, it can be considered that angles defined by the respective points constituting the three-dimensional structures are also similar. In a three-dimensional structure, there exist an angle θ defined by three points and an angle φ defined between planes formed by three among four points. Hereafter, a method of reducing the number of points to be related will be described, taking the angle θ defined by the three points as an example.

In relating the sets, the number of candidates for a point to be related is reduced by selecting and relating such points from the point sets A and B such that an angle defined between s ($2 \leq s \leq m-1$, n−1) elements close to element $b_j$ of the point set B relative to an angle defined between s points close to the element $a_i$ of the point set A lies within a permissible error range $\Delta \theta$.

Figure 20:
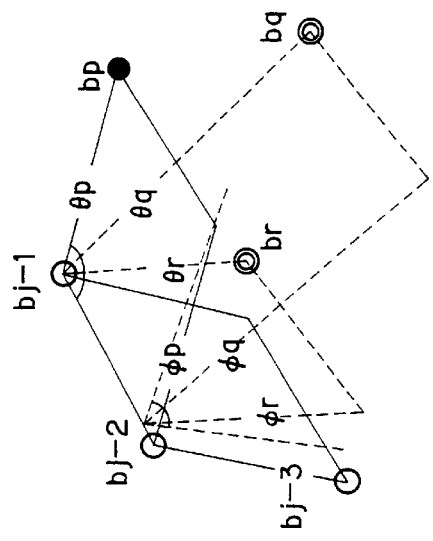
FIGS. 20A and 20B are diagrams explaining refining of candidates using an angle relationship.
Figure 20:
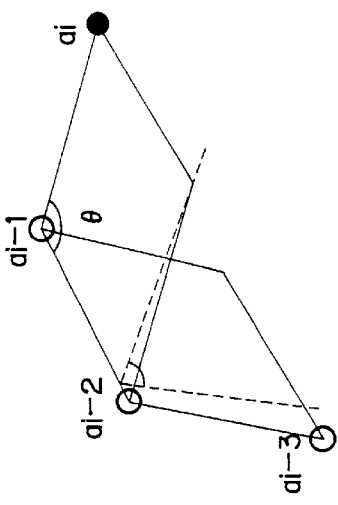

FIG. 20B shows a case where, considering angles defined by respective elements as a geometric relationship established between the elements of the point set A, the points of the point set B are related based on this consideration.

In the case where an angle defined by the element $a_i$ of the point set A and two (s=2) points $a_{i-1}$, $a_{i-2}$ close to the element $a_i$ is $\theta_a$, and angles defined by the elements $b_p$, $b_q$, $b_r$ and two elements $b_{j-1}$, $b_{j-2}$ close to these elements $b_p$, $b_q$, $b_r$ are $\theta_p$, $\theta_q$, $\theta_r$, points such that an angle difference lies within the permissible error range $\Delta \theta$ are selected and related. In this figure, since only the point $b_p$ satisfies the relationship: $|\theta_a-\theta_p| \leq \Delta \theta$, the point $b_p$ is selected as a candidate for $b_j$.

(c) Refining of Candidates Based on Distances and Angles from a Center of Gravity If the three-dimensional structures are similar to each other, it can be considered that distances and angles from a center of gravity are similar. Accordingly, the number of candidates for a point to be related can be reduced by calculating the center of gravity from the selected points, and comparing the distances and angles using a technique similar to (a) and (b).

(5) Refining of Candidates Based on a Threshold Value Condition

The point sets can be more efficiently related by setting a specified threshold value in the aforementioned methods (1) to (4), and pruning a retrieval path if an attribute value of a candidate is greater than this threshold value. As this threshold value, for example, restriction in a nil number (the number of nil) and restriction in a r.m.s.d. value can be used.

(a) Restriction in a Nil Number

When a total number of nil becomes too large among the generated combinations, meaningless candidates for combinations are generated as a result. Accordingly, in relating the elements of the point sets A and B, if the total number of nil becomes in excess of a given threshold value, the generation of the unnecessary candidates can be prevented by excluding these from the candidates, thereby relating the elements more efficiently.

Figure 21:
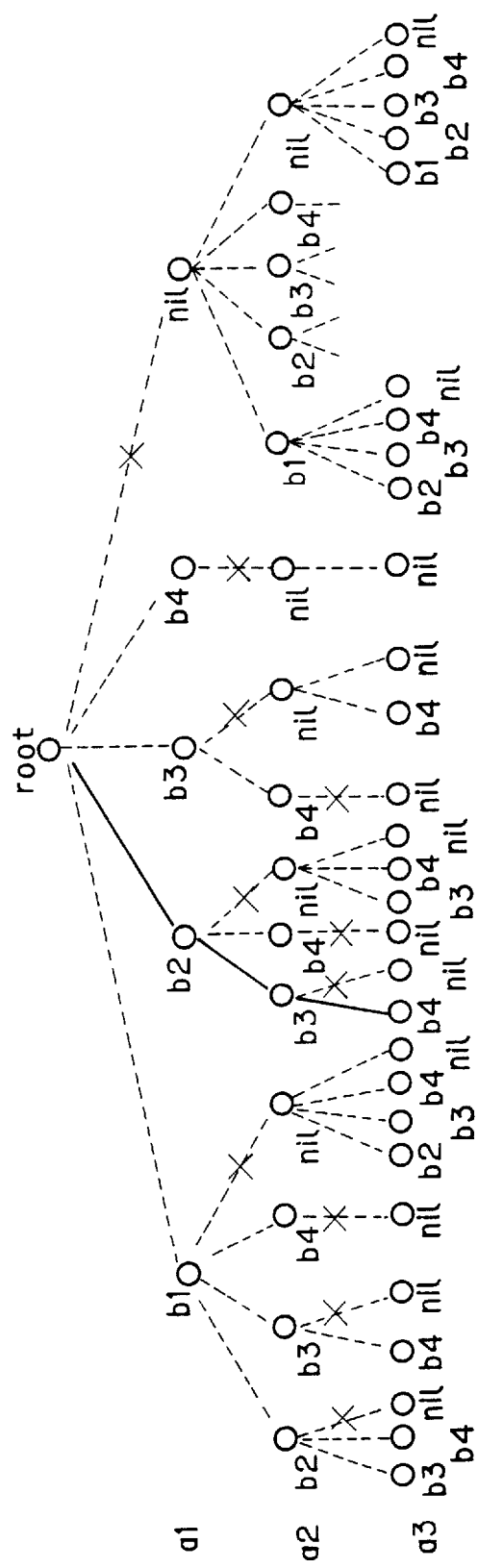
FIG. 21 is a diagram showing a tree structure explaining the refining of candidates using a restriction condition of the number of nil elements.

FIG. 21 shows an example of pruning in a case where a total number of nil is restricted to 0 in relating a point set A={$a_1, a_2, a_3$} to a point set B={$b_1, b_2, b_3, b_4$}. In this figure, a portion designated at x in a tree structure is a portion to be pruned.

(b) Restriction in an r.m.s.d. Value

In the case where an r.m.s.d. value of all the points related thus far becomes exceedingly bad by relating an element $a_i$ of a point set A to an element $b_j$ of a point set B, it is preferable to exclude this point from consideration of the candidates. In view of this, the r.m.s.d. value of all the points when the element $a_i$ is related to the element $b_j$ is calculated, and this point is selected as a candidate if the calculated r.m.s.d value is not greater than a given threshold value. On the contrary, this point is excluded from the candidates if the r.m.s.d value is in excess of the given threshold value. In this way, the candidates for a point to be related can be generated more efficiently.

(6) Refining of Candidates Based on an Attribute of a Point

The number of candidates for a point to be related can be reduced by using an attribute of the point in relating an element $a_i$ of a point set A to an element $b_j$ of a point set B. The attributes of the point, for example, include the type of an atom, an atomic group, and a molecule, the hydrophilic property, the hydrophobic property, and the positive or negative charge. It is determined whether the point is selected as a candidate by checking whether these attributes coincide.

For example, in the case of relating elements constituting proteins, the number of candidates for a point to be related can be reduced by using the type of an amino acid residue (corresponding to an atomic group) as an attribute of the point. Regarding the types of amino acid residues or the like, please refer to references such as "Fundamental to Biochemistry," pp. 21–26, Tokyo Kagaku Dohjin Shuppan.

Further, the candidates for the point to be related can be reduced by adding a restriction to a specific element. For example, the candidates to be retrieved can be reduced by providing the restriction that the nil is not inserted to a certain point or by designating an attribute of point to a certain point.

2. Adaptation Examples

Described below are adaptation examples where the theme consists of a protein as a three-dimensional structure of a substance. Here, however, there is no particular limitation except that the subject basically has three-dimensional structure, and the invention can be adapted to even those having general molecular structures relying upon the same method.

(1) Device for Displaying the Superposition of Molecular Structures

In examining properties of a substance, the molecules are superposed one upon another, and a common portion or specific portion is discriminated so as to analyze or predict properties of the substances. Since such operations have been effected manually, a device that automatically displays the molecular structures in an overlapped manner is preferred.

Figure 22:
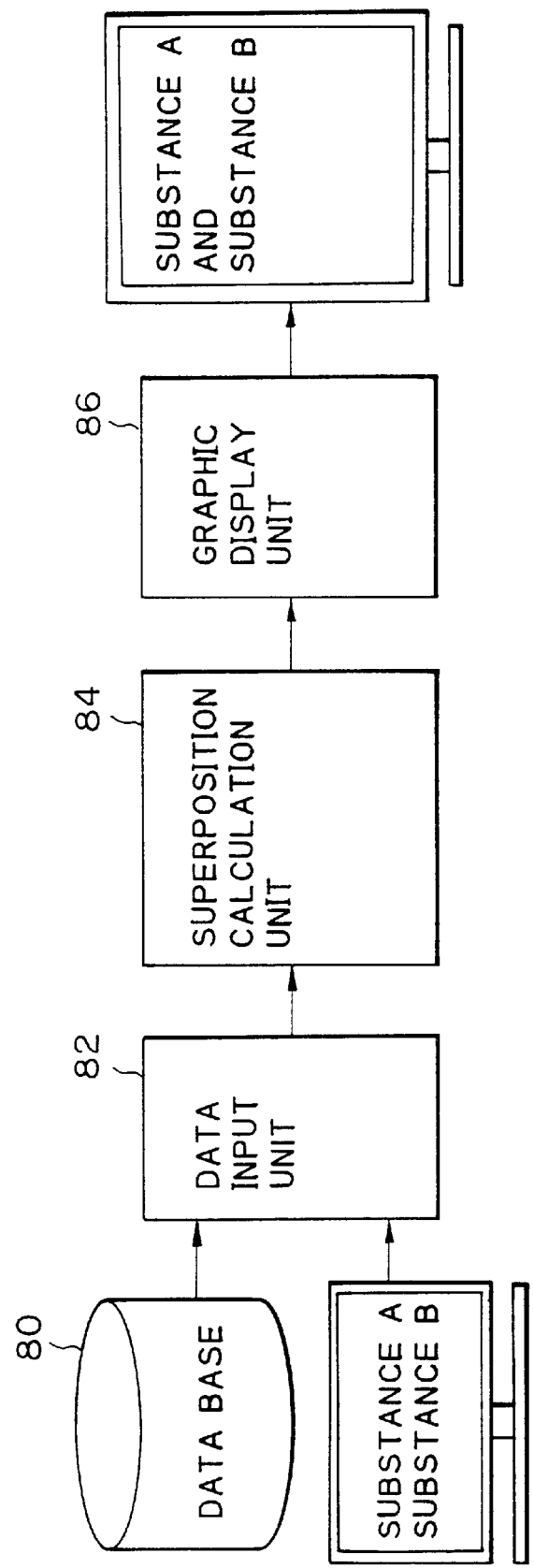
FIG. 22 is a block diagram showing a construction of a molecular structure display device according to another embodiment of the present invention.

FIG. 22 is a diagram of system constitution of a device that displays the molecular structures in an overlapped manner according to the present invention. This device is constituted by a data base 80 in which are registered data related to the three-dimensional structures of substances, a data input unit 82 that reads the registered data and an input command from a user, a superposition calculation unit 84 that superposes the three-dimensional structures (three-dimensional coordinates) of the substance read from the data base 80 on the method of superposition discussed above in subsection 1 entitled "Various Methods of Determining Correspondence" such that r.m.s.d. values will become the smallest, and a graphic display unit 86 that displays the three-dimensional structures in an overlapped manner based on the calculated results.

(a) Data Base 80

The data base 80 stores the data related to three-dimensional structures of substances, i.e., stores the names of substances, three-dimensional coordinates of atoms constituting the substances, etc.

(d) Data Input Unit 82

The data input unit 82 reads from the data base the data (three-dimensional coordinates) of substances that are to be superposed based on an input command of a user, and sends the data to the superposition calculation unit 84.

(c) Superposition Calculation Unit 84

The superposition calculation unit 84 determines correspondence among the elements that constitute the substances in order to superpose three-dimensional structures (three-dimensional coordinates) of substances according to the method of superposition discussed in Section 1, entitled "Various Methods of Determining Correspondence ", in a manner such that optimum r.m.s.d. values are obtained, and sends the results to the graphic display unit 86. In determining the correspondence, there is provided a function that finds correspondence between spatially similar portions based on the order of amino acid sequence that constitutes a protein, and a function that finds correspondence between spatially similar portions irrespective of the order of amino acid sequence. In retrieving the spatially similar portions based on the order of amino acid sequence, amino acids constituting the protein can be grasped as an ordered set whose elements are ordered according to the numbers of amino acid sequence, and therefore similar portions can be calculated based on the methods discussed in Section 1, subsections (2), (3), (4), (5), and (6). By grasping the amino acids simply as a nonordered set, furthermore, it is possible to calculate spatially similar portions irrespective of the order of amino acid sequence relying upon the systems mentioned in the section 1, subsections (1), (3), (4), (5) and (6).

(d) Graphic Display Unit 86

The graphic display unit 86 displays the three-dimensional structures of substances in a superposed manner based on the results calculated by the superposition calculation unit 84. Upon looking at the displayed result while manually rotating it, it is understood what portions are superposed and haw they are superposed in a 3D graphic.

Figures 23A, 23B:
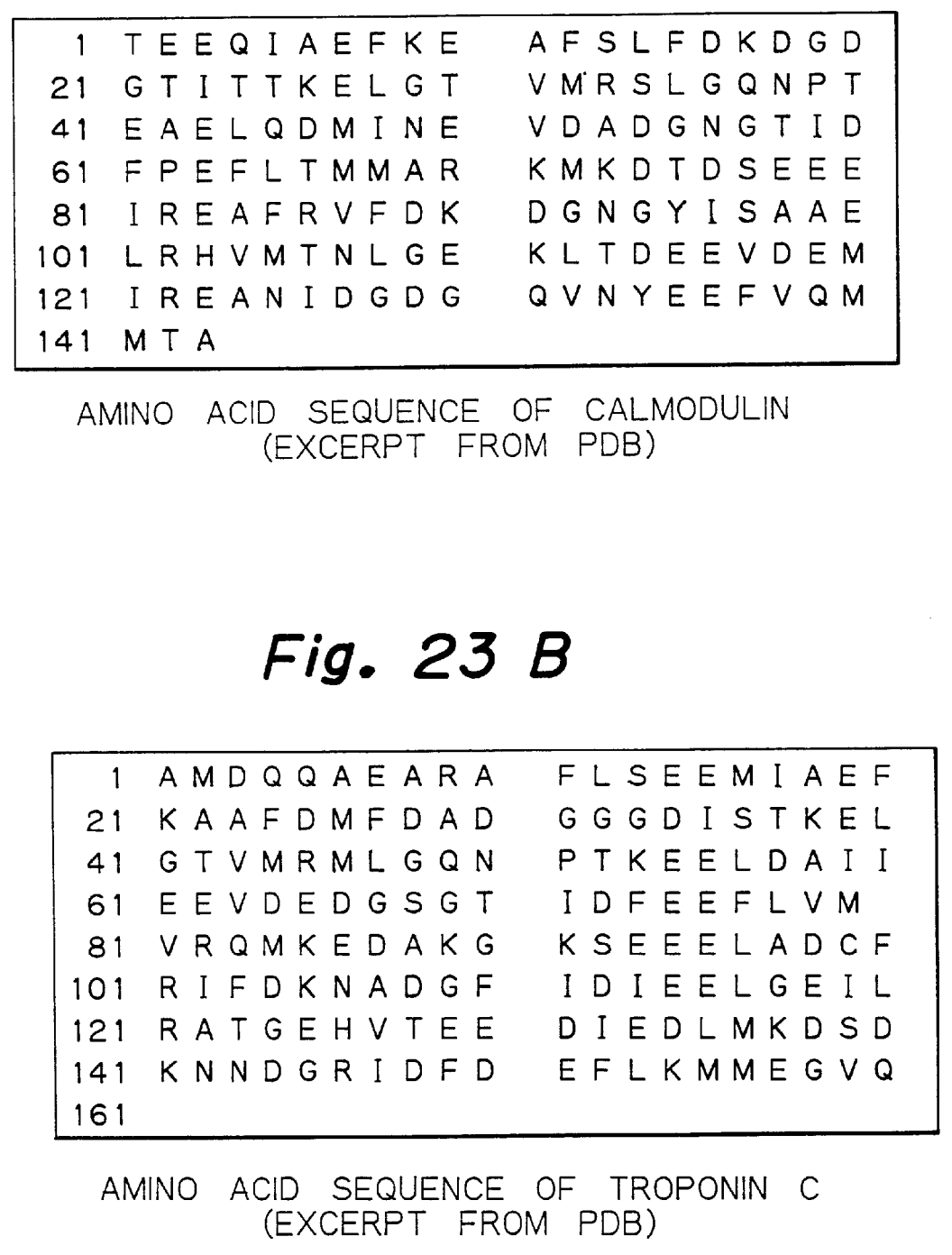
Figure 24:
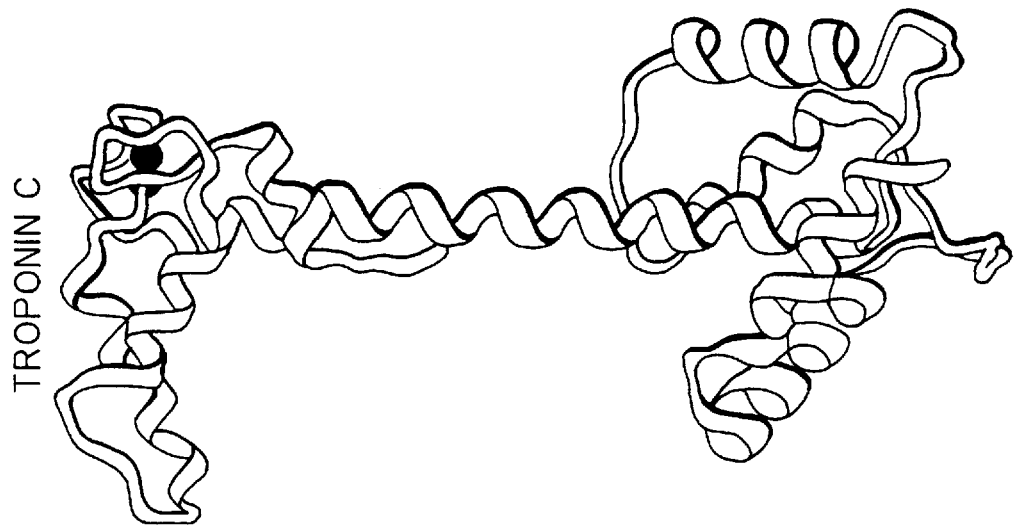
FIGS. 24A and 24B are diagrams showing three-dimensional structures of calmodulin and troponin C, respectively.
Figure 24:
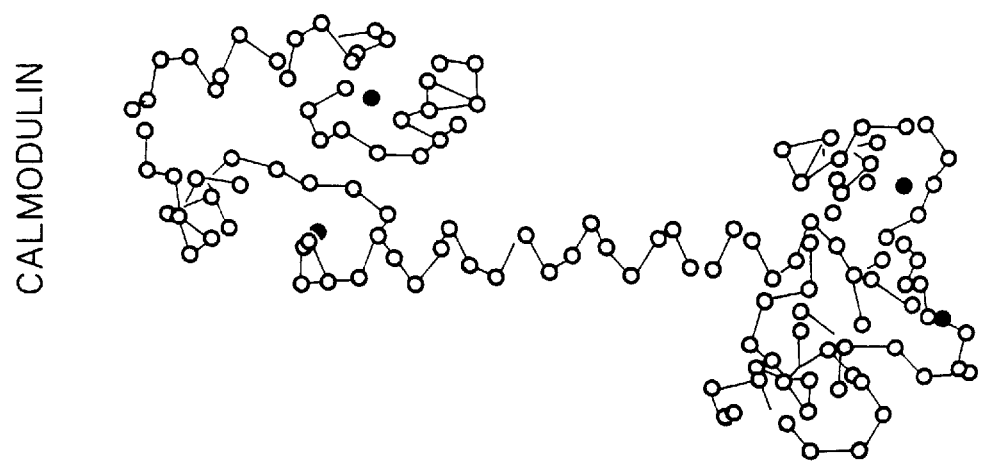

FIG. 23A shows an amino acid sequence of calmodulin, which is a protein, and FIG. 23B shows an amino acid sequence of troponin C. FIGS. 23A and 23B show in excerpts the amino acid sequences registered to the PDB. The amino acid sequence shown in FIG. 23A lacks amino acids that correspond to amino acid sequence Nos. 1–4 and 148 included in the ordinary amino acid sequence and, hence, the numbers are shifted. Hereinafter, these diagramed amino acid sequence numbers will be used. As shown in FIG. 24A, it is known from results of biochemical experiments that calmoduline can bind four $Ca^{2+}$ as indicated by black rounds. Also, it is known that troponin C can bind two $Ca^{2+}$ as indicated by black rounds in FIG. 24B. It is known that calmoduline has four places (sites) to bind $Ca^{2+}$ in its amino acid sequence and among these amino acids of sequence numbers 81–108 and 117–143 form skeletons similar to those of two sites to bind $Ca^{2+}$ in troponin C. A protein is constituted by amino acids and it is known that its skeleton can be represented by the coordinates of atoms (Cα) that constitute the amino acids. FIG. 25 shows the results obtained when a spatially similar portion (a single site) is searched for based on the order of amino acid sequence using the $Ca^{2+}$ binding site 81–108 of calmodulin as a probe. FIG. 25 indicates that the amino acid sequence numbers 96–123 in troponin C correspond to the $Ca^{2+}$ binding sites 81–108 in calmodulin. These results are in agreement with the biochemically experimented results. FIG. 26 shows the results obtained when spatially similar portions (a plurality of sites) are searched for based on the order of amino acid sequence using $Ca^{2+}$ binding site 81–108 and 117–143 in calmodulin as probes. FIG. 26 indicates that the amino acid sequence numbers 96–123 and 132–158 in troponin C correspond to the $Ca^{2+}$ binding sites 81–108 and 117–143 in calmodulin. These results are in agreement with the biochemically experimented results, too. By using the apparatus of the present invention as described above, correspondence among the constituent elements of substances can be calculated in a manner such that the r.m.s.d. values are minimized in the three-dimensional structures of the substances. By displaying the corresponding portions in a superposed manner, therefore, it becomes possible to display the substances in a superposed manner in an optimum condition.

Figure 27:
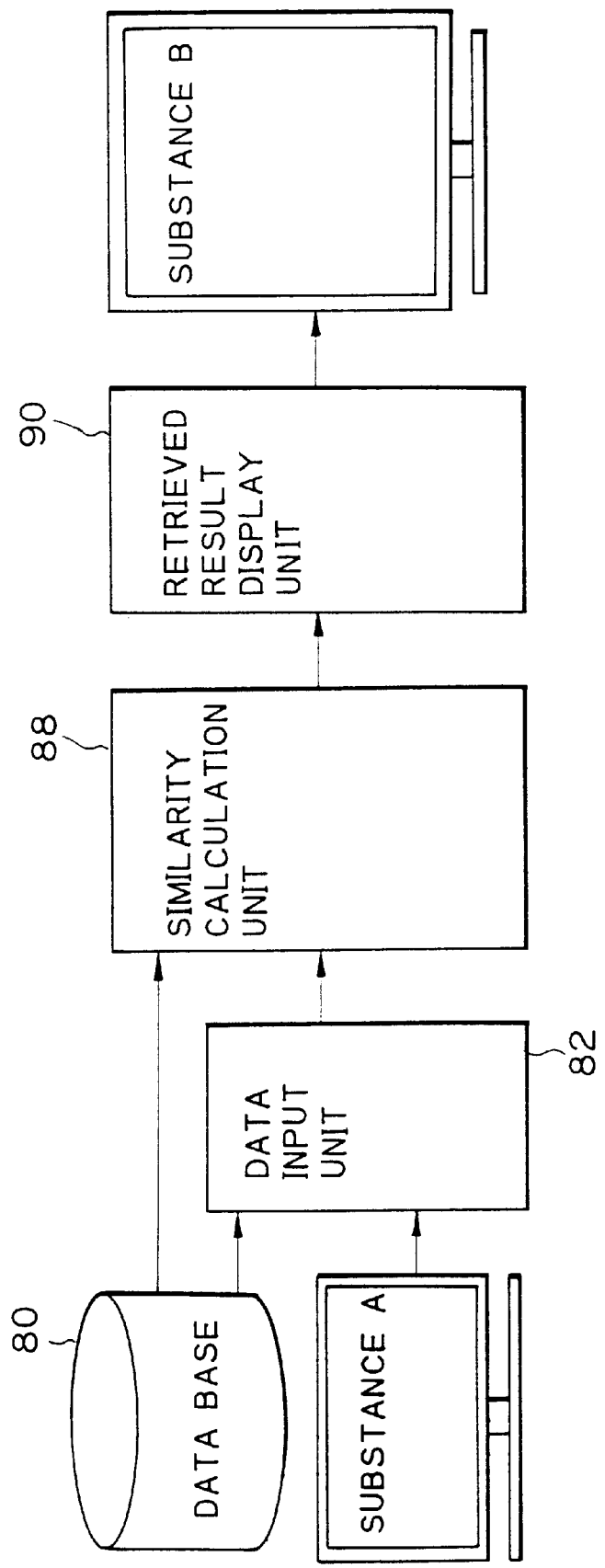
FIG. 27 is a block diagram of a construction of a three-dimensional structure retrieval device according to another embodiment of the present invention.
Figure 28:
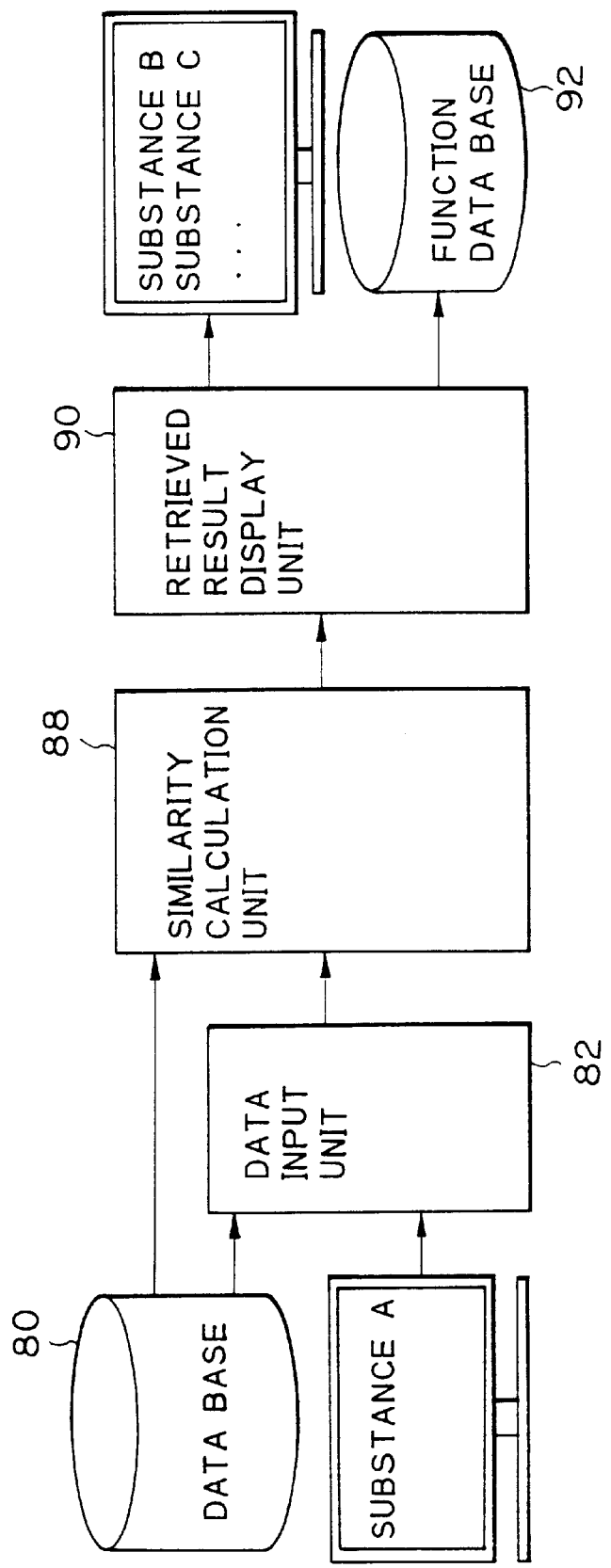
FIG. 28 is a diagram showing a construction of a function data base generating device according to another embodiment of the present invention.

(2) Three-dimensional Structure Retrieval Device and Function Data Base Generating Device It is essential to clarify a correlation between the function and the structure of a substance in order to develop a substance having a new function such as a new medicine or to improve the function of a substance that already exists. To promote the aforesaid work, it becomes necessary to make references to many substances having similar three-dimensional structures. This necessitates a three-dimensional structure retrieving device that is capable of easily taking out the substances having similar three-dimensional structures form the data base. Moreover, a device of this kind makes it possible to prepare a function data base in which are collected three-dimensional structures that are related to the functions. The function data base will be described later in (3). FIG. 27 is a diagram illustrating the system constitution of a three-dimensional structure retrieving device that is constituted by a data base 80 that stores three-dimensional structures of substances, a data input unit 82 that reads the data registered to the data base 80 and an input command of a user, a similarity calculation unit 88 that retrieves structures similar to three-dimensional structures (three-dimensional coordinates) of substances read form the data base 80 and which minimize the r.m.s.d. value, based on the method of superposition mentioned in the Chapter 1, and a retrieved result display unit 90 that displays the retrieved results. FIG. 28 is a diagram showing the system constitution of a device that generates a function data base.

(a) Data Base 80

The data base 80 stores the data related to three-dimensional structures of substances, i.e., stores the names of substances, the three-dimensional coordinates of atoms constituting the substances, etc.

(b) Data Input Unit 82

The data input unit 82 reads the data of three-dimensional structures that serve as keys for retrieval and the data of three-dimensional structures registered to the data base 80 that will be referred to during the retrieval based an the input command from the user, and sends the data to the similarity calculation unit 88.

(c) Similarity Calculation Unit 88

The similarity calculation unit 88 calculates optimum superposition of three-dimensional structures. At this moment, there are provided a function for retrieving spatially similar portions based on the order of amino acid sequence that constitutes a protein, and function for retrieving spatially similar portions irrespective of the order of amino acid sequence. In retrieving the spatially similar portions based on the order of amino acid sequence, amino acids constituting the protein can be grasped as an ordered set whose elements are ordered according to the numbers of amino acid sequence, and therefore similar portions can be calculated based on the methods described in section 1, subsections (2), (3), (4), (5) and (6). By grasping the amino acid simply as a nonordered set, furthermore, it is possible to calculate spatially similar portions irrespective of the order of amino acid sequence relying upon the systems mentioned in section 1, subsections (1), (3), (4), (5) and (6).

(d) Retrieved Result Display Unit 90

The retrieved result display unit 90 expresses similar portions as amino acid sequence names and amino acid numbers based on the results of the similarity calculation unit 86, and displays r.m.s.d. values as a scale of similarity.

Figure 30:
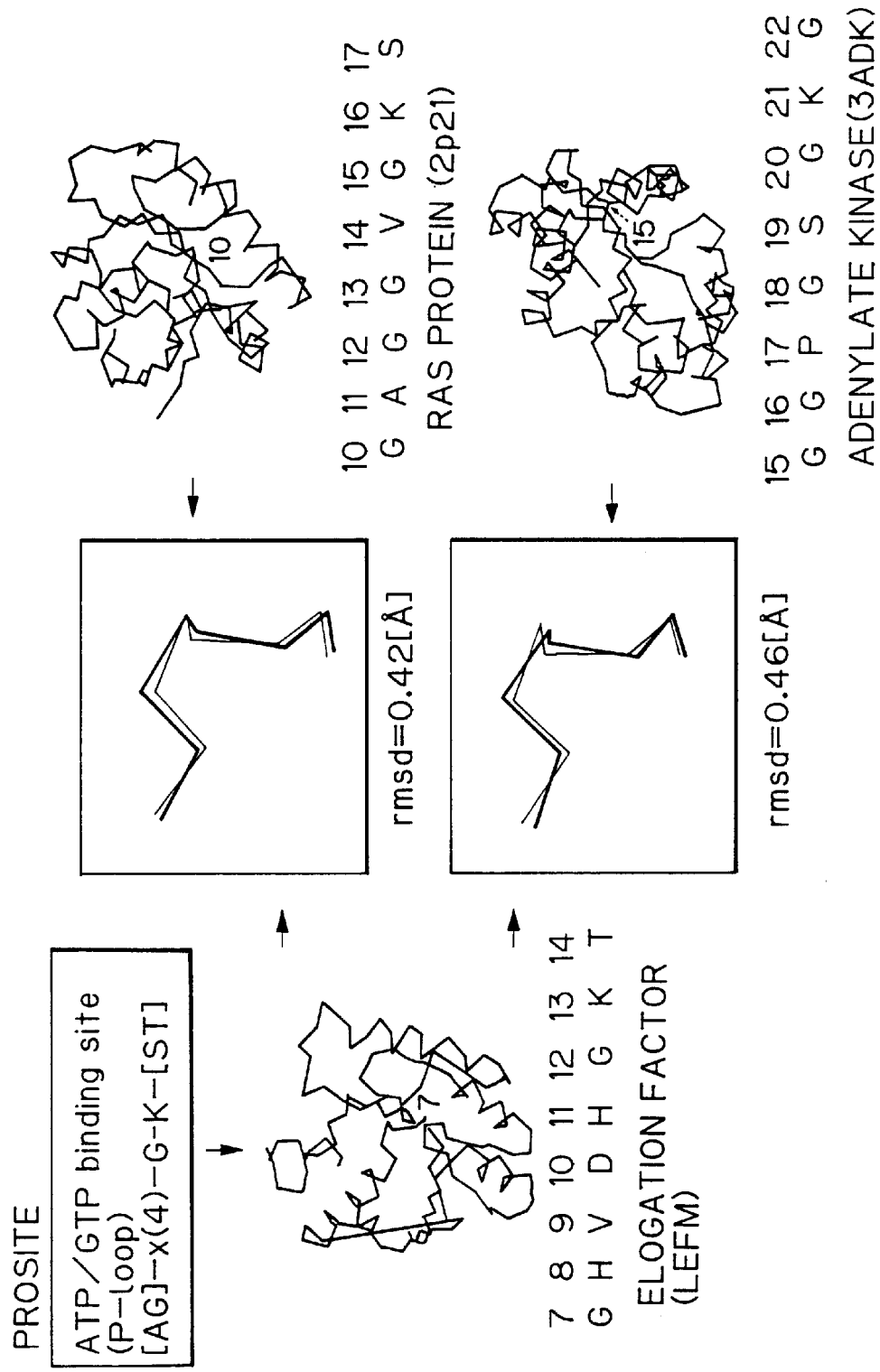
FIG. 30 is a diagram showing the retrieval results as three-dimensional structures.

FIG. 29 shows the results obtained when similar three-dimensional structures are retrieved form the PDB using, as probes, coordinates of Cα corresponding to the amino acid residue Nos. 7 to 14 in elongation factor of protein which is a binding site for phosphoric acid of GTP (guanosine triphosphate). Retrieval is carried out over 744 three-dimensional structures of protein among 824 data registered to the PDB. FIG. 29 shows amino acid residue numbers of a target protein that is retrieved, an amino acid residue sequence, an amino acid residue sequence of a probe, and r.m.s.d. values between target and probe three-dimensional structures. As a result, eight three-dimensional structures are retrieved (including probe itself). If classified depending upon the kinds of proteins, there are retrieved three adenylate kinases, two elongation factors (between them, one is probe itself) and three ras proteins, all of them are the sites where phosphoric acid of ATP or GTP is bound. Thus, the function of sites binding phosphoric acid of ATP or GTP has a very intimate relationship to their three-dimensional structures and their structures are very specific because they never incidentally coincide with other structures that are not phosphoric acid binding sites. In FIG. 30, the retrieved results are partly shown by their three-dimensional structures.

By using this device as described above, it is possible to retrieve similar structures from the data base in which are stored three-dimensional structures of substances by designating the three-dimensional structure of a substance that serves as a probe.

(3) Function Predicting Device

Figure 31:
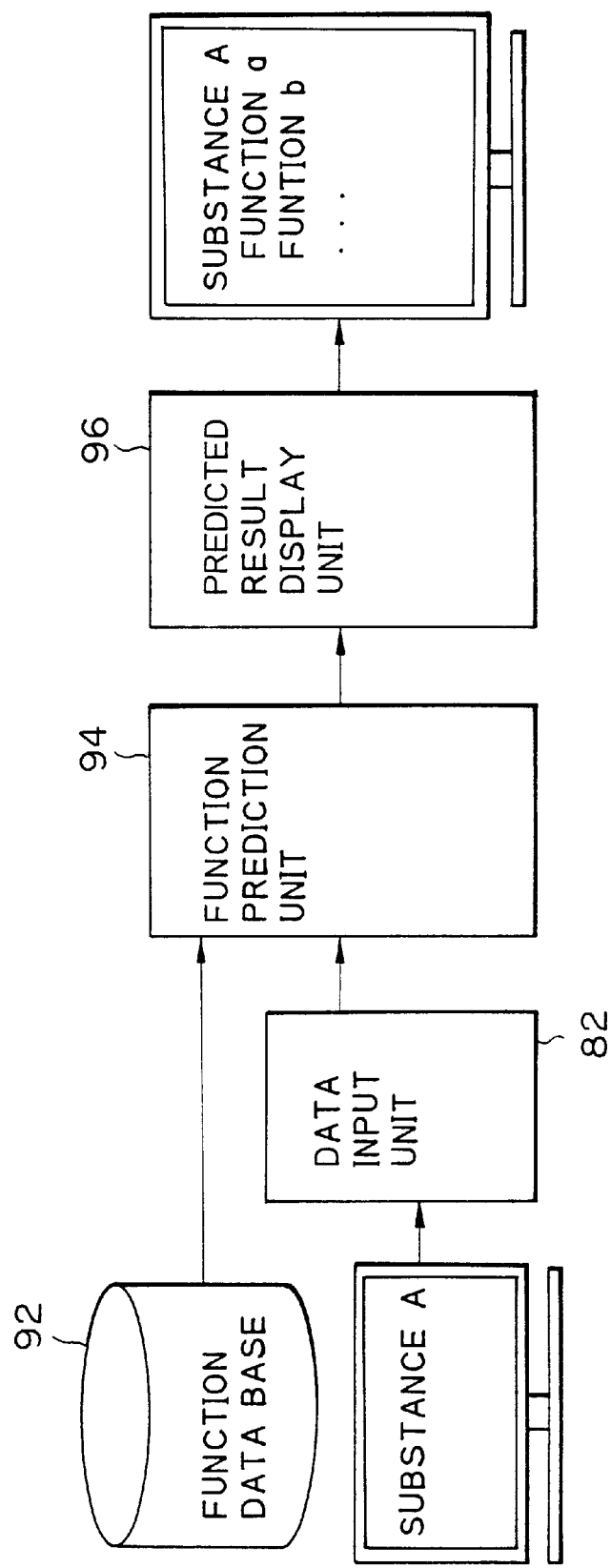
FIG. 31 is a block diagram showing a construction of a function predicting device according to another embodiment of the present invention.

As will be implied from the results shown in FIG. 29, it is considered that a protein has a three-dimensional structure that specificly develops its function. Therefore, if a data base (hereinafter referred to as function data base) of three dimensional structures specific to the function is provided for each of the functions, then it becomes possible to predict what function is exhibited by a substance and by which portion (hereinafter referred to as function site) of the three-dimensional structure the function is controlled by examining whether the structures registered to the function data bases exist within the three-dimensional structure of the substance at the time when the three-dimensional structure of the substance is newly determined by the X-ray crystal analysis or NMR. FIG. 31 illustrates the function predicting device which is constituted by a data input unit 82 that receives as inputs the three-dimensional structures of substances, a function data base 92 to which are registered the three-dimensional structures that are related to functions, a function prediction unit 94 that performs optimum superposition of the three-dimensional structure read from the function data base 92 and the three-dimensional structure of a substance that is an input based on the method of retrieving the three-dimensional structure described in Section 1 in order to determine whether the three-dimensional structure includes a structure related to the function, and specifies the function sites, and a predicted result display unit 96 that displays the predicted results.

(a) Data Input Unit 82

The data input unit 82 reads the data of three-dimensional structures constituting substances and sends them to the function prediction unit.

(b) Function Data Base 92

The function data base 92 stores the functions of substances and data related to three-dimensional structures specific to the functions. The data base stores the names of functions, and three-dimensional coordinates of atoms constituting three-dimensional structures specific to the functions, etc. The function data base 92 is formed by a function data base-generating device (FIG. 28) that is constituted similarly to the three-dimensional structure retrieving device described in (2) above.

(c) Function Prediction Unit 94

The function prediction unit 94 calculates the optimum superposition of three-dimensional structures registered to the function data base 92 and three-dimensional structures that are input. At this moment, there are provided a function for retrieving spatially similar portions based on the order of amino acid sequence that constitute a protein, and a function for retrieving spatially similar portions irrespective of the order of amino acid sequence. In retrieving the spatially similar portions based on the order of amino acid sequence, amino acids constituting the protein can be grasped as an ordered set whose elements are ordered according to the numbers of amino acid sequence, and therefore similar portions can be calculated based on the methods described in Section 1, subsections (2), (3), (4), (5) and (6). By grasping the amino acid sequence simply as a nonordered set, furthermore, it is possible to calculate spatially similar portions irrespective of the order of amino acid sequence relying upon the systems mentioned in section 1, subsections (1), (3), (4), (5) and (6).

(d) Predicted Result Display Unit 96

The predicted result display unit 96 expresses the names of functions, names of amino acid sequences at function sites and amino acid residue numbers registered to the function data base relying on the results of the function prediction unit 94, and displays r.m.s.d. values as a scale of similarity.

Analysis of Three-dimensional Structures of Molecules II

In the aforementioned method of imparting correspondence, similar structures were successfully picked up by refining the candidates by taking into consideration such threshold conditions as geometrical relations such as distances among the elements in a point set, r.m.s.d. values and the number of nils, as well as attributes of constituent elements (kinds of amino acids in the case of a protein), and by finding optimum combinations. Still, extended periods of time are often required for calculating under certain shape conditions of the three-dimensional structure, the number of elements that constitute a point set, geometrical limitations and threshold values. Therefore, the calculation must be carried out at higher speeds. It, however, is difficult to establish a method that is capable of executing the processings at high speed under any condition.

As shown in FIGS. 32A and 32B, therefore, the three-dimensional structures (partial structures) of molecules are divided into those having linear structures and those having non-linear structures. Among them, those having linear structures are processed at a higher speed using a method described below.

Referring to FIG. 32A, the structure in which two points at both ends of a three-dimensional structure are most distant from each other is called a linear structure. Referring to FIG. 32B, on the other hand, the structure in which two points at both ends are not most distant from each other is called a non-linear structure.

In accomplishing correspondence among the elements between point sets A and B that form three-dimensional structures, according to this embodiment, after the point set B is divided depending upon the spatial size or the number of constituent elements of the point set A in order to find subsets of points that are candidates for the corresponding points, the optimum correspondence is effectively searched for with respect to each of the subsets. Described below is a method of finding the subsets.

(1) Division of an Ordered Point Set B According to the Number of Constituent Elements of a Point Set A FIG. 33 is a diagram explaining how to divide a point set B according to the number of constituent elements of a point set A.

The size of search space is decided according to the number m of elements of the point set A, and the point set B is divided according to the size in order to reduce the space to be searched, thereby shortening the time for calculation. In an example of FIG. 33, a size 10, which is twice as great as the number 5 of elements of the point set A, is set to be the size of a space to be searched, in order to effect the processing.

Figure 34:
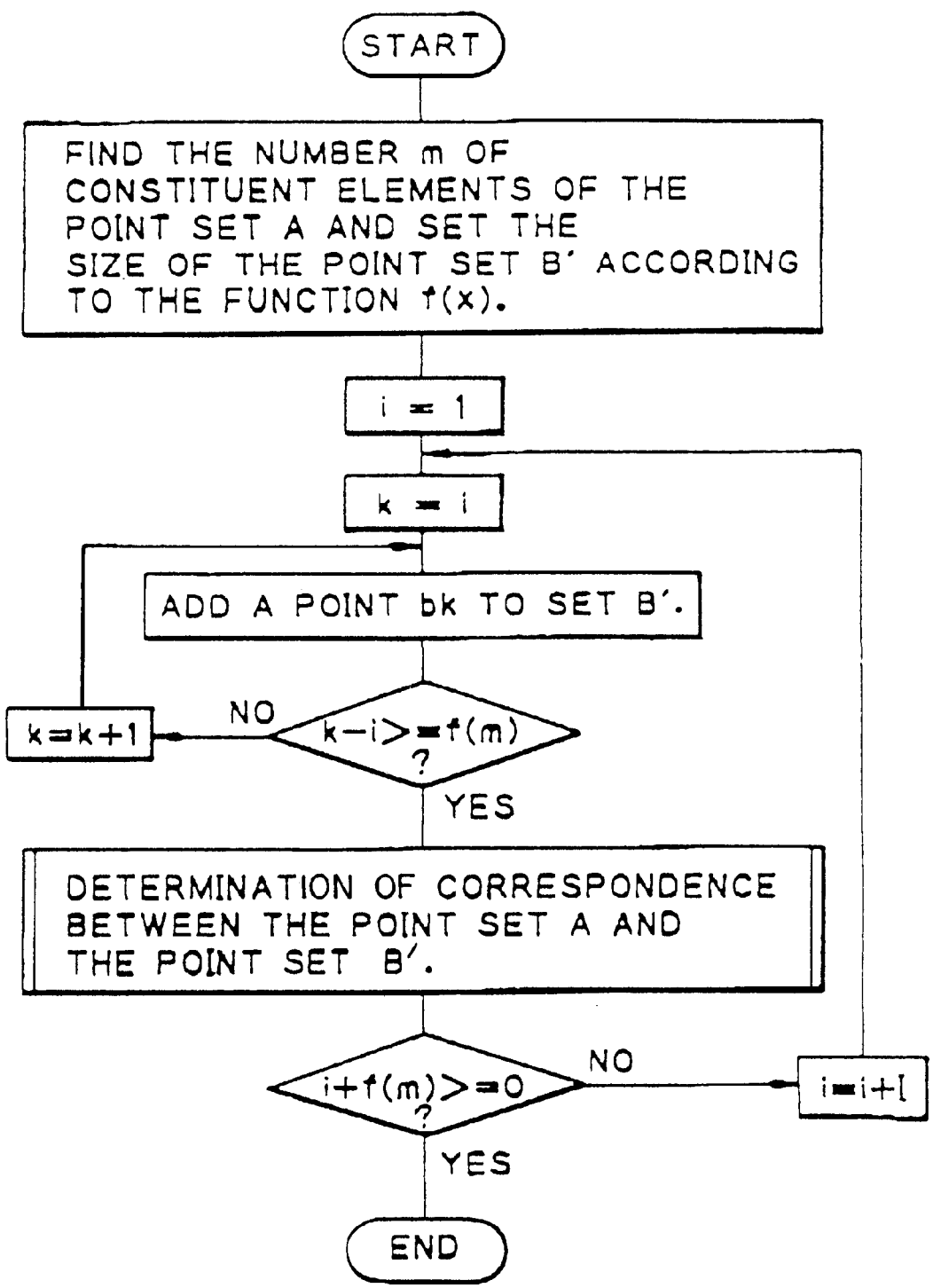
FIG. 34 is a flowchart showing a process for dividing a point set B into subsets according to the number of elements belonging to a point set A.

FIG. 34 shows a division algorithm for the point set B.

Ordered point sets are given as $A=[a_1, ---, a_m]$, $B=[b_1, ---, b_i, ---, b_j, ---, b_n]$, and the following processing is effected for the subset B' of the point set B.

Process 1: Find the number m of elements of the point set A.

Process 2: Set the size (f(m)) of B' in compliance with a function f(x) that defines the size of the point set B'.

Process 3: Divide the point set B to obtain the following subset B'.
  (a) $j=i+f(m)-1$
  (b) Point set $B'=[b_i, b_{i+1}, ---, b_{j-1}, b_j]$ Process 4: The points $a_1$ and $b_i$ are related to each other and then the remaining elements of the point sets A, B' are related to each other according to the method explained with reference to FIGS. 17 to 21, in order to find correspondence that meets a predetermined limiting condition.

Process 5:
  When $b_j$ is a final element of the point set B, the program is finished.
  When $b_j$ is not the final element of the point set B, obtain i=i+1 and return to process 3.

(2) Division of an Ordered Point Set B According to the Spatial Size of the Point Set A.

As shown in FIG. 35A, a distance d is found across the two points at both ends of the point set A, and the point set B is divided by the distance d as shown in FIG. 35B in order to reduce the search space, thereby shortening the time for calculation. According to this method, however, since the correspondence of a head element of the set is not fixed as mentioned with reference to the process 4 of (1), there exists a probability that the same solution may be calculated many times. Therefore, prior to advancing to the next search space, the next search space is set by taking into consideration the position of a solution obtained in the previous search space, so that the search spaces will not be overlapped and the same solution will not be calculated many times.

Figure 36:
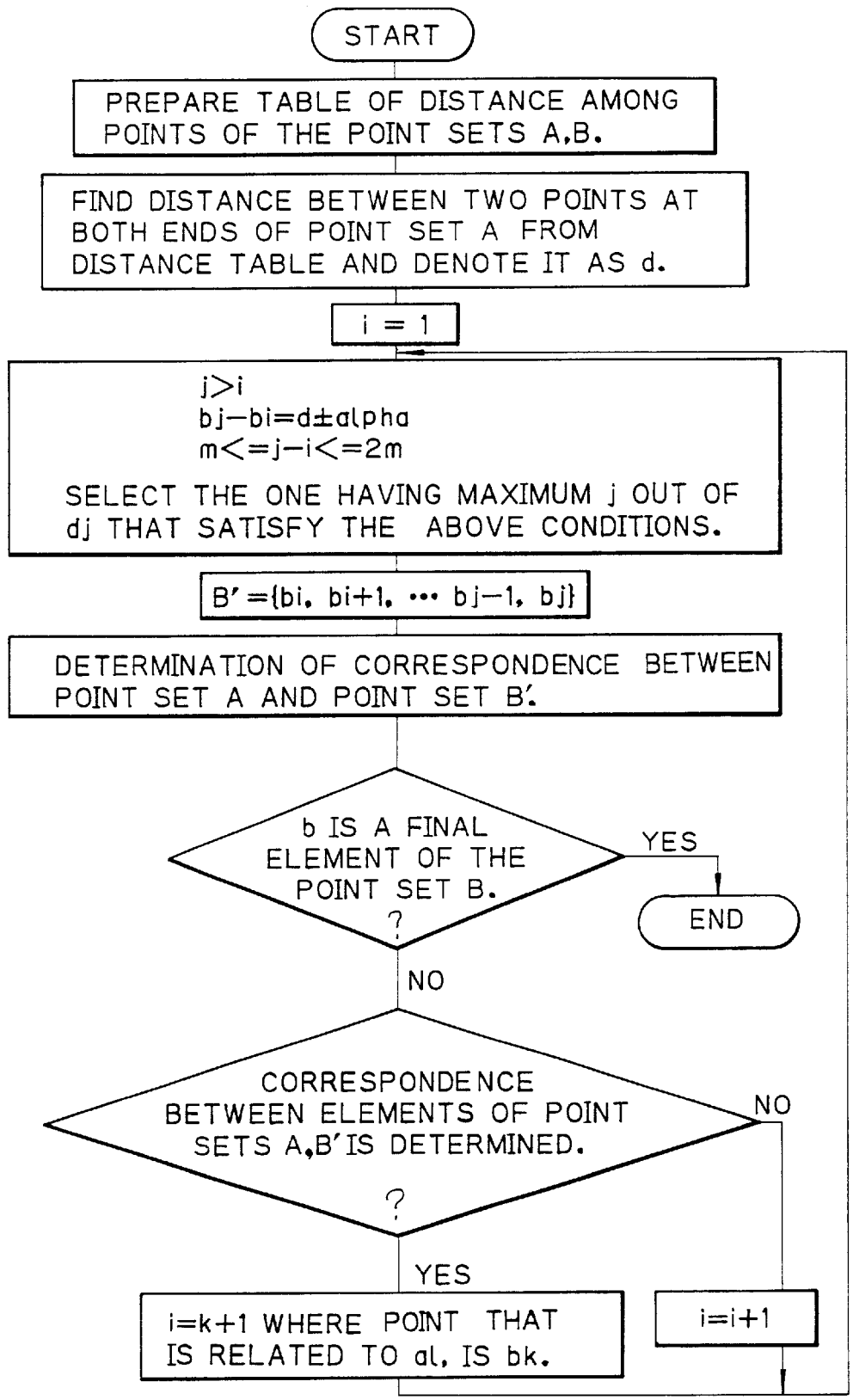
FIG. 36 is a flowchart showing an example of a process for dividing a point set B into subsets according to a spatial size of a point set A.

FIG. 36 is a diagram showing a division algorithm for the ordered point set B depending upon the spatial size of the point set A.

The ordered point sets are given as $A=[a_1, ---, a_m]$, $B=[b_1, ---, b_i, ---, b_j, ---, b_n]$, and the following process is effected for the subset B' of the point set B.

Process 1: Distances among points of the point sets A and B are calculated to prepare a distance table (not shown).

Process 2: A distance between a first point and a final point ($a_1$, $a_m$) in the point set A is found from the distance table, and is denoted as d.

Process 3: Divide the point set B.
(a) Find from the distance table the one having a maximum j from among $b_j$ that have a distance of d+α from $b_i$ (i=1, in initial state) and that satisfy m≦j−i≦2 m.
(b) Obtain a point set B'=[$b_i$, $b_{i+1}$, - - - , $b_{j-1}$, $b_j$].

Process 4: Accomplish correspondence among the elements of point sets A, B' according to the method explained with reference to FIGS. 17 to 21, in order to find correspondence that meets a predetermined limiting condition.

Process 5: When $b_i$ is a final element of the point set B, the program is finished.

Process 6: When $b_i$ is not the final element of the point set B:
i) Obtain i=k+1 and return to the process 3 when a solution that satisfies predetermined limiting condition is met between the point sets A and B', where a point corresponding to al is bk; or
ii) obtain i=i+1 and return to the process 3 when a solution is not obtained between the point sets A and B'.

(3) Other Method of Dividing the Ordered Point Set B According to the Spatial Size of the Point Set A.

Figure 37:
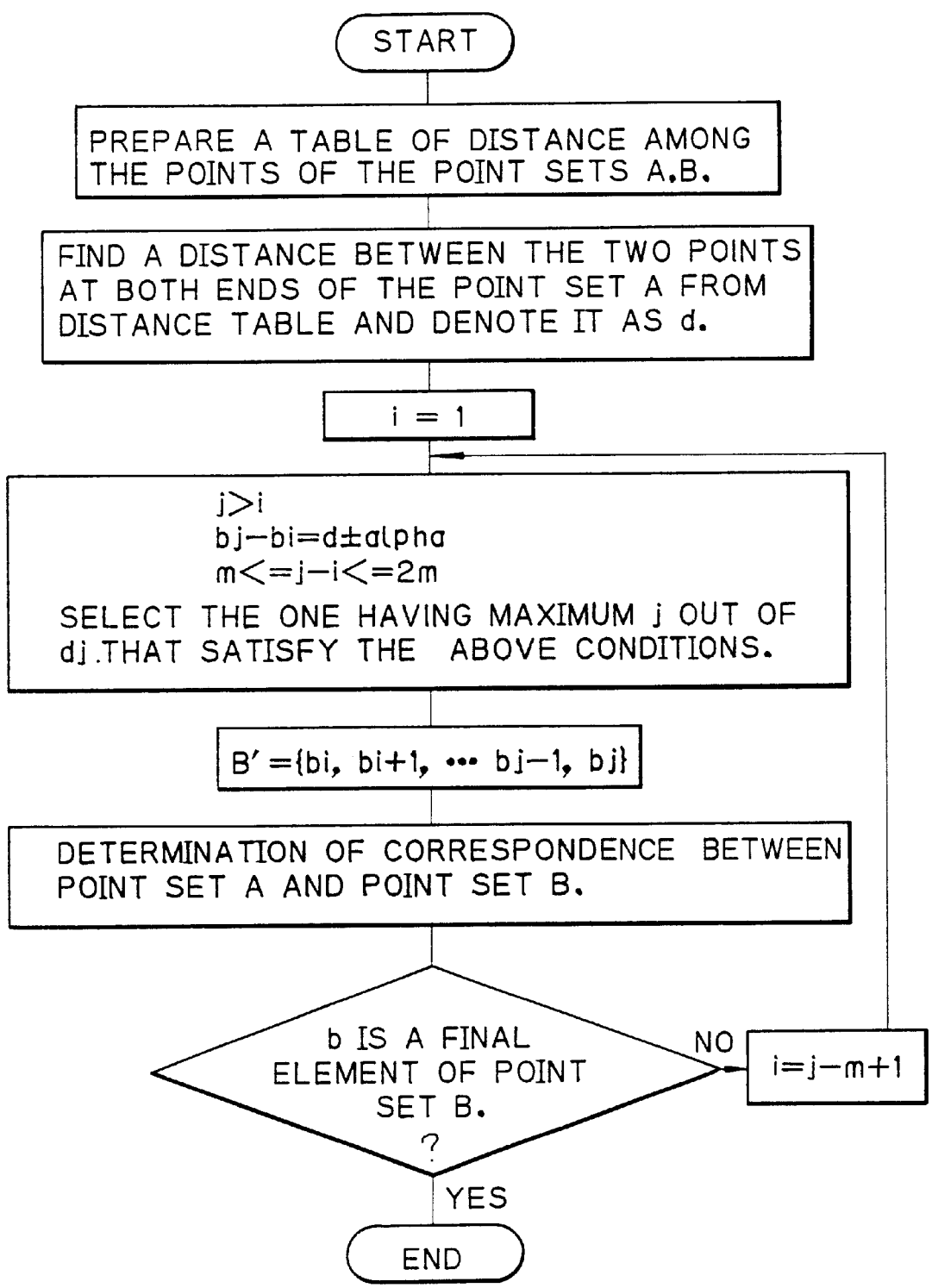
FIG. 37 is a flowchart showing another example of the process for dividing a point set B into subsets according to a spatial size of a point set A.

As shown by an algorithm of FIG. 37, it is possible to divide the ordered point set B depending on the spatial size of the point set A. Even in this case, a distance is found across two points at both ends of the point set A, and the point set B is divided by this distance to reduce the search space and to shorten the time for calculation. Moreover, at the time of advancing to the next search space, the next search space is set by taking into consideration the number of elements of the point set A that serve as search keys, so that the search spaces will not be overlapped and the same solution will not be calculated many times.

The ordered point sets are given as A=[$a_1$, - - - , $a_m$], B=[$b_1$, - - - , $b_i$, - - - , $b_j$, - - - , $b_n$], and the following process is effected for the subset B' of the point set B.

Process 1: Distances among points of the points sets A and B are calculated to prepare a distance table (not shown).

Process 2: A distance between a first point and a final point ($a_i$, $a_m$) in the point set A is found from the distance table, and is denoted as d.

Process 3: Divide the point set B.
(a) Find from the distance table the one having a maximum j from among $b_j$ that have a distance of d+α from $b_i$ (i=1, in initial state) and that satisfy m≦j−i≦2 m.
(b) Obtain a point set B'=[$b_i$, $b_{i+1}$, - - - , $b_{j-1}$, $b_j$].

Process 4: Accomplish correspondence among the elements of point sets A, B' according to the method explained with reference to FIGS. 17 to 21, in order to find correspondence that meets a predetermined limiting condition.

Process 5: When $b_i$ is a final element of the point set B, the program is finished. When $b_i$ is not the final element of the point set B, obtain i=j−m+1 and return to the process 3.

In determining the correspondence among the points that form three-dimensional structures, the points are related to each other after the search space of three-dimensional structures is divided. Therefore, the points can be related to one another within short periods of time. These methods can similarly be adapted to the processing devices that are described with reference to FIGS. 22, 27, 28 and 31.

Figures 38A, 38B:
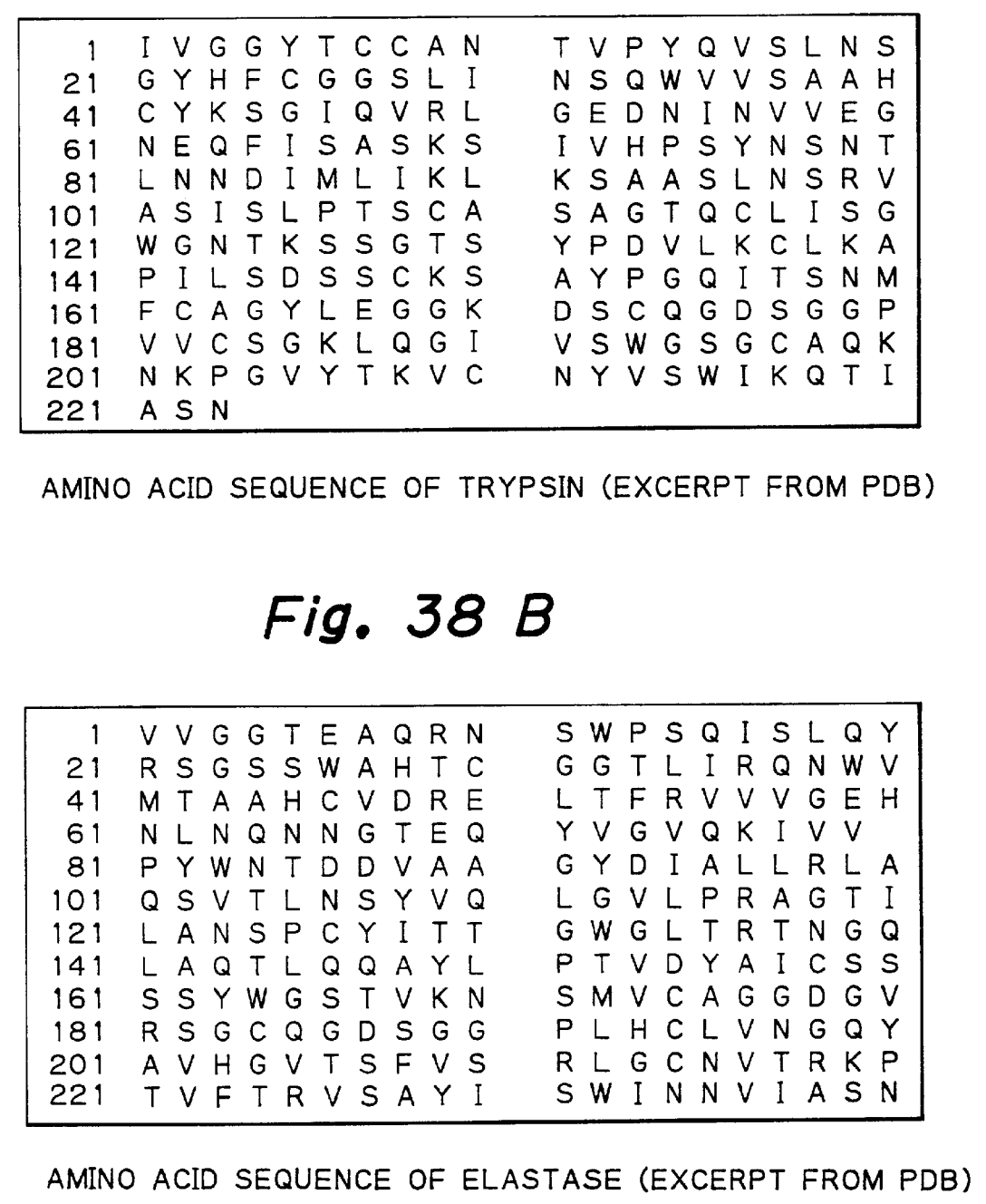

FIGS. 38A shows the amino acid sequence of a protein trypsin, and FIG. 38B shows the amino acid sequence of elastase. FIGS. 38A and 38B show excerpts of amino acid sequences registered to the PDB. The amino acid sequence numbers shown in FIGS. 38A and 38B are those that are simply given to the amino acids described in the PDB starting from 2 and are different from the traditional amino acid numbers. In the following description, the amino acid numbers that are diagramed will be used.

The trypsin and elastase that are shown are some kinds of proteolytic enzymes called serine protease, and in which histidine, serine and aspartic acid are indispensable at the active sites. Though these enzymes have quite different substrate specificity, they are considered to be a series of enzymes from the point of view of evolution since they are similar to each other with respect to structure and catalytic mechanisms.

FIG. 39A shows the retrieved results of histidine active sites of elastase with the histidine active sites (36–41) of trypsin as probes. It will be understood that 41–46 of elastase correspond to the active sites 36–41 of trypsin. FIG. 39B shows the retrieved results of serine active sites of elastase with serine active sites (175–179) of trypsin as probes from which it will be understood that 186–190 of elastase correspond to the active sites 175–179 of trypsin. These results are in agreement with the results obtained through biochemical experiments.

Analysis of Three-Dimensional Structures of Molecules III

Three-dimensional structures of proteins contain common basic structures such as α-helix and β-strand which are called secondary structures. Several methods have heretofore been developed to effect automatic retrieval based upon the similarity in the secondary structures without using r.m.s.d. values. According to these methods, partial structures along the amino acid sequence are denoted by symbols of secondary structures and are compared by way of symbols, but it was not possible to compare similarities of spatial position relationships of the elements that constitute partial structures or to compare similarities of spatial position relationships of partial structures.

Therefore, described below are a method in which a set of elements constituting a molecule is divided into subsets based on the secondary structures, and the subsets are related to each other based on the similarities of spatial position relationships of elements that belong to the subsets, a method of evaluating similarities of spatial position relationships of a plurality of subsets that are related to one another, and a method of analysis by utilizing such methods.

(1) Division of a Point Set into Subsets.

The structure A and the structure B are, respectively, constituted by a point set A=[$a_1$, $a_2$, $a_3$, - - - , $a_i$, - - - , $a_m$], where 1≦i≦m and a point set B=[$b_1$, $b_2$, $b_3$, - - - , $b_j$, - - - , $b_n$], where 1≦j≦n, and each point is expressed by a three-dimensional coordinate consisting of $a_i$=($x_i$, $y_i$, $z_i$) and $b_j$=($x_j$, $y_j$, $z_j$)

In order to facilitate determination of the correspondence among the points, the structure is divided into partial structures that are structurally meaningful, and a points set is divided into subsets. Examples of the partial structures which are structurally meaningful include functional groups and partial structures having certain functions in the case of chemical substances, and secondary structures such as helixes, sheets structures and partial structures developing certain functions in the case of proteins.

The coordinates of a partial structure are found by using the known data or by the analysis of three-dimensional coordinates. The point set A divided into subsets is denoted as $A=[(a_1, a_2, ---, a_k), (a_{k+1}, a_{k+2}, ---, a_l), ---, (a_{l+1}, a_{l+2}, ---, a_m)]$, where $1 \leq k \leq l \leq m$. Here, if $SA1=(a_1, a_2, ---, a_k)$, $SA2=(a_{k+1}, a_{k+2}, ---, a_l)$, $---$, $SAp=(a_{l+1}, a_{l+2}, ---, a_m)$, then the set SA's are subsets which constitute the points set A, and the set A is expressed by SA's as $A = (SA1, SA2, ---, SAp)$. Similarly, the point set B is divided into SB's which are subsets of B, and is expressed as $B=(SB1, SB2, ---, SBq)$.

(2) Determination of Correspondence Among the Subsets.

Considered below is the determination of correspondence among elements of the structure $A=(SA1, SA2, ---, SAp)$ and the structure $B=(SB1, SB2, ---, sBq)$, i.e., to determine the correspondence among subsets. In this case, possible correspondence can be described by a tree structure created by successively giving correspondence to the element constituting the sets. A node of the root of the tree is a starting point. A leaf node represents a result of possible setting of correspondence, and an intermediate node represents a partial result. Nil is used when there is no corresponding element.

Figure 40:
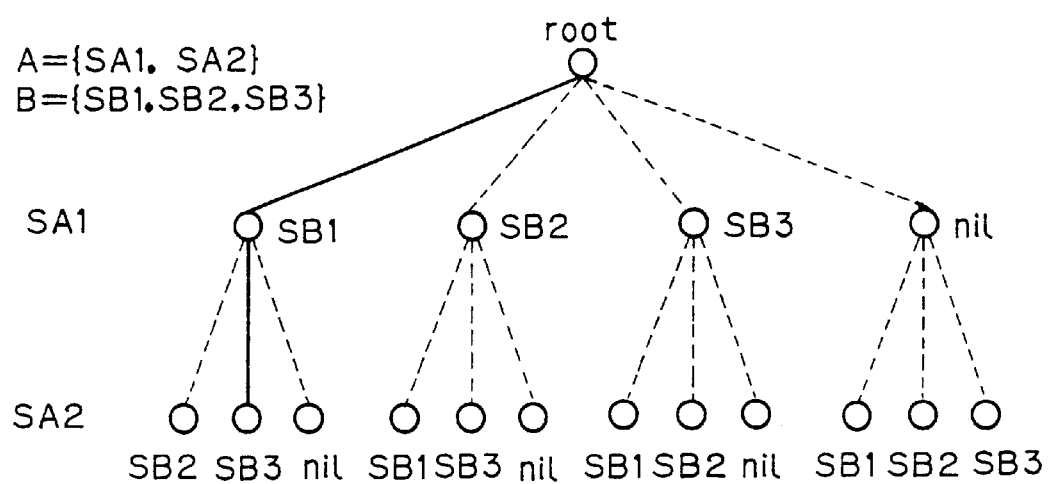
FIG. 40 is a diagram showing a tree structure expressing candidates for a combination of correspondence between subsets.

FIG. 40 is a diagram illustrating the possible correspondence of subsets. If a status tree that corresponds to all possible combinations is created, the number of nodes becomes significantly high. Therefore, the branches must be pruned. Namely, when the nodes are added by giving correspondence between two subsets, the matching is effected between the subsets, and the nodes are added provided the result satisfies the limiting condition. The limiting condition will be described later in (4). The matching of the subsets is carried out in compliance with the method described in the "Analysis of Three-Dimensional Structures of Molecules I".

(3) Determination of Correspondence Among Subsets Wherein Partial Correspondence is Predetermined and/or that are Ordered When partial correspondence between subsets is predetermined and/or when subsets are ordered in the above case (2), branches of the tree structure formed in (2) are pruned based thereon.

(4) Refining the Candidates by the Similarity Among the Subsets

In the above methods (2) and (3), the branches are pruned based on the similarity between the two subsets that are candidates in order to determine the correspondence efficiently. The attributes possessed by the candidates and the structural similarity between the two subsets are taken into consideration. The attributes of subsets may be the kinds of functional groups and kinds of functions in the case of chemical substances, and the constituent elements in the secondary structure and the kinds of functions in the case of proteins. The structural similarity of the two subsets is judged by the three-dimensional structure matching method which accomplishes the correspondence among the elements of the two ordered point described in the "Analysis of Three-Dimensional Structure of Molecules I". The r.m.s.d. among the points is calculated when an optimum matching is effected based on this method.

Figure 41:
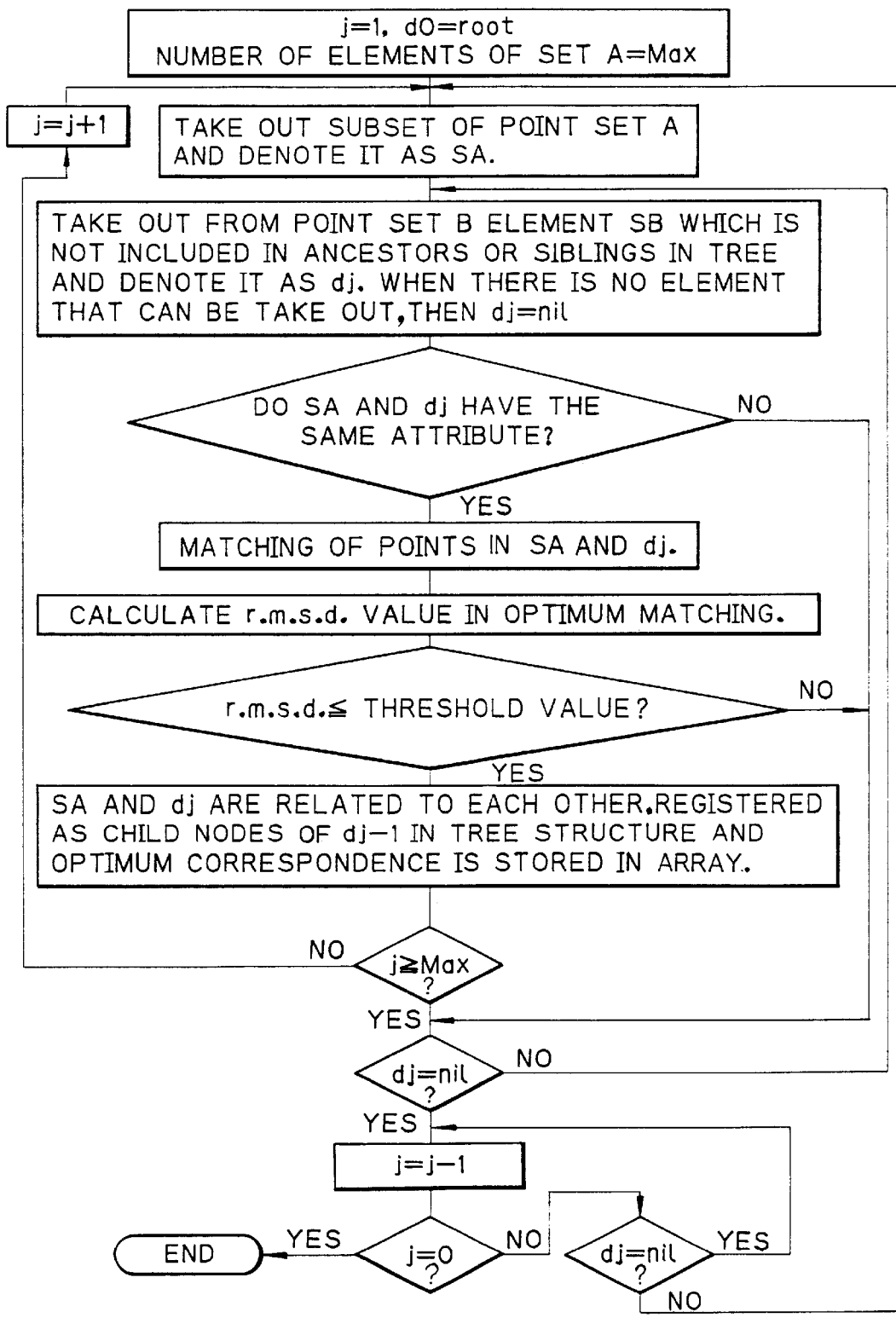
FIG. 41 is a flowchart showing a process of determining correspondence between subsets.

The candidates can be refined by generating nodes of correspondence only when the two subsets that are the candidates have the same attribute and their r.m.s.d. values are smaller than a threshold value. FIG. 41 shows an algorithm for determining correspondence of subsets of the sets A and B where the above limiting condition is taken into consideration.

In FIG. 41, a subset is taken out from the point set A and is denoted as SA. Further, and element SB that is not included in the ancestor or siblings of the tree structure is taken out from the point set SB and is denoted as $d_j$. When there is no element that can be taken out, then $d_j$=nil.

Then, SA and $d_j$ are examined in regard to whether their attributes are the same or not, and when the attributes are not the same, the combination is discarded for pruning. When the attributes are the same, the point sets are matched, and an r.m.s.d. value is calculated under the optimum matching. When this value is smaller than a predetermined threshold value, SA and $d_j$ are related to each other, and are registered as child nodes of $d_{j-1}$ in the tree structure, and correspondence of an optimum point is stored in the sequence. The above-mentioned processing is repeated for all of the subsets.

(5) Decision of Similarity Between the Structure A and the Structure B

Two point sets are created using elements belonging to the subsets related in (4) above, and an r.m.s.d. value between them is calculated in compliance with Kabsh's method, and when the value is smaller than the threshold value, it is decided that the two structures are similar to each other.

Described below is a system for retrieving three-dimensional structures of proteins using the secondary structural similarity that can be realized based on the above-mentioned method.

Figure 42:
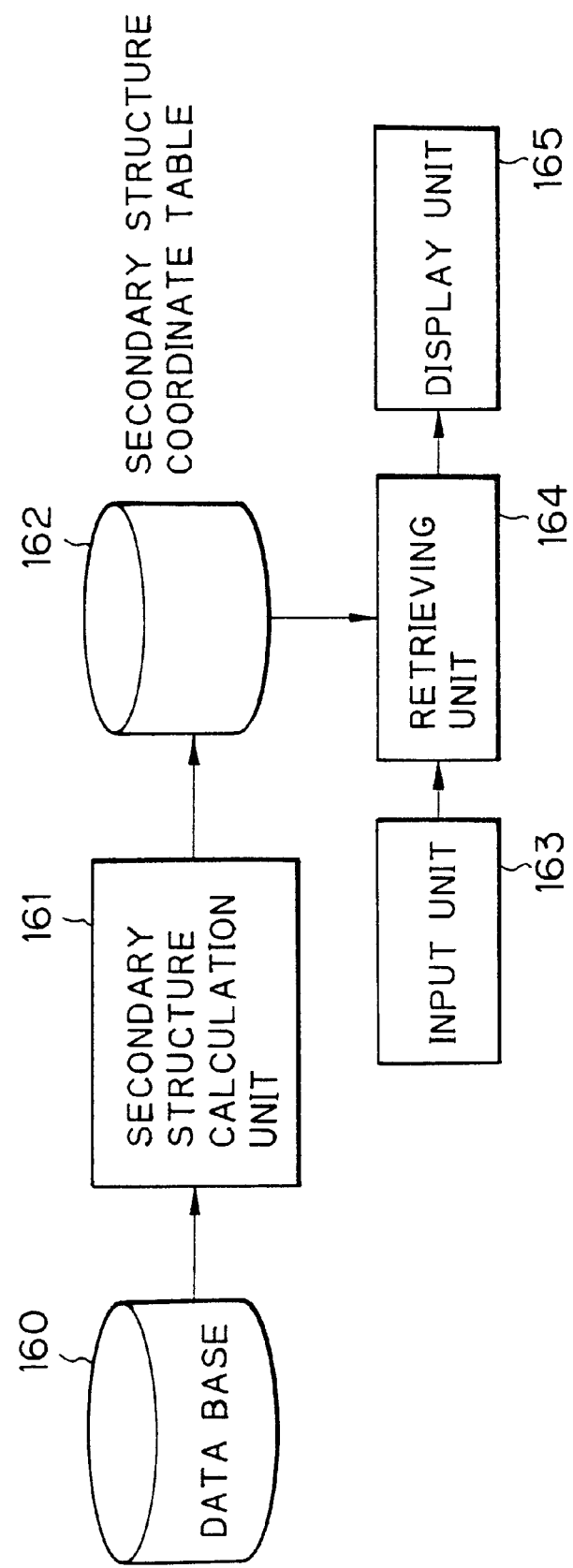
FIG. 42 is a block diagram showing a construction of retrieval process device according to another embodiment of the present invention.

FIG. 42 illustrates the constitution of a retrieval system that is made up of a data base 160 to which are registered three-dimensional structure data of proteins, a secondary structure calculation unit 161 that determines a secondary structure from the three-dimensional structure data in the data base 160 and divides it into partial structures, a secondary structure coordinate table 162 that stores the results obtained by the secondary structure calculation unit 161 as a type of the secondary structure and three-dimensional coordinates of points that constitute the type of the secondary structure, an input unit 163 that reads an input command of a user, a retrieving unit 164 that retrieves a similar structure based on the aforementioned method relying on the command that is input and the data in the secondary structure coordinate table, and a display unit 165 that graphically displays the retrieved result. Details of the units will now be described.

(a) Data Base 160

The data base stores three-dimensional structure data of proteins. Name and three-dimensional coordinate date of constituent atoms are registered for each of the proteins.

(b) Secondary Structure Calculation Unit 161

Figure 43:
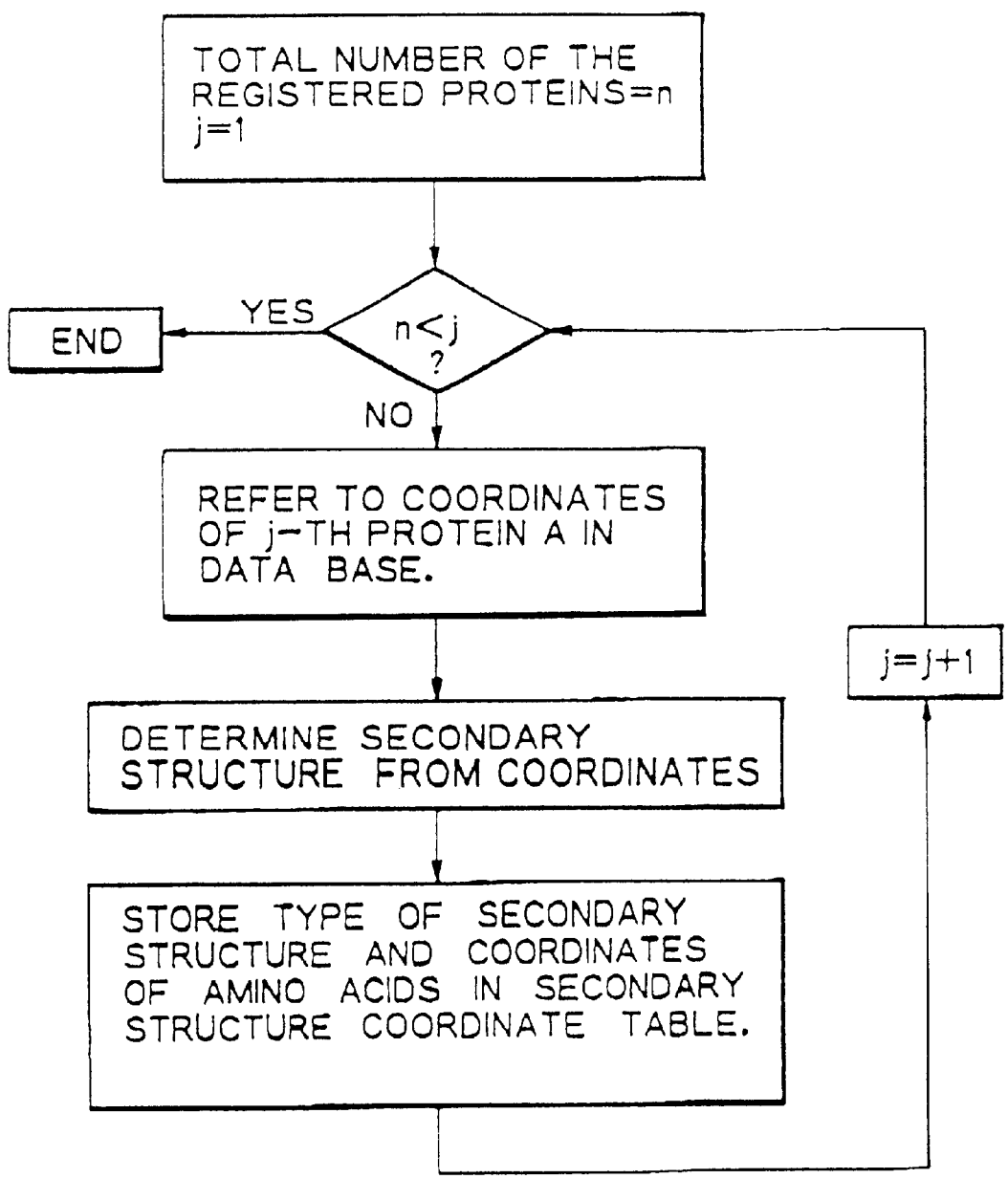
FIG. 43 is a flowchart showing a process of dividing a point set into subsets according to secondary structures.

The secondary structure calculation unit 161 divides the structure of a protein into types of secondary structures based on the three-dimensional coordinates in the data base, and divides a point set into subsets. Table I shows the types of the secondary structures and the definitions thereon. The type the i-th amino acid belongs to is sequentially determined according to the definitions shown in Table I, and subsets are created from a series of coordinates of the amino acid belonging to the same type. The thus determined type of the secondary structure and the coordinate data of the constituent amino acid are stored in the secondary structure coordinate table 162. By repeating this operation, n amino acids are all grouped into subsets. FIG. 43 shows a flow of process related to the determination of the secondary structure and division into subsets.

TABLE I

Types of secondary structures and their definitions

| Type | Definition |
|---|---|
| $3_{10}$-Helix | Structure in which carbonyl group of i-th residues and amide groups of i + 3-th residues are aligned by hydrogen bonds therebetween. |
| α-Helix | Structure in which carbonyl groups of an i-th residues and amide groups of an i + 4-th residues are aligned by hydrogen bonds therebetween. |
| Parallel β-sheet | Structure in which hydrogen bonds are formed between carbonyl groups of i − l-th residues and amide groups of j-th residues and between carbonyl groups of j-th residues and amide groups of i + l-th residues, or hydrogen bonds are formed between carbonyl groups of j − l-th residues and amide groups of i-th residues and between carbonyl groups of i-th residues and amide groups of j + l-th residues. |
| 3-Turn | Structure in which hydrogen bonds are formed between carbonyl groups of i-th residues and amide groups of i + 2-th residues. |

(c) Secondary Structure Coordinate Table 162

FIG. 44 illustrates a constitution of the secondary structure coordinate table 162 where the types of the secondary structures determined by the secondary structure calculation unit 161 and the coordinate date of amino acids constituting the secondary structure are stored. In this example, the subsets S1 and S2 belongs to the type of α-helix and the partial sets S3, - - - belongs to the type of β-sheet.

(d) Input Unit 163.

The input unit 163 reads the name of a protein that serves as a retrieval key based on the secondary structure coordinate table 162 and the input command from the user, and sends it to the retrieving unit 164.

(e) Retrieving Unit 164.

Figure 45:
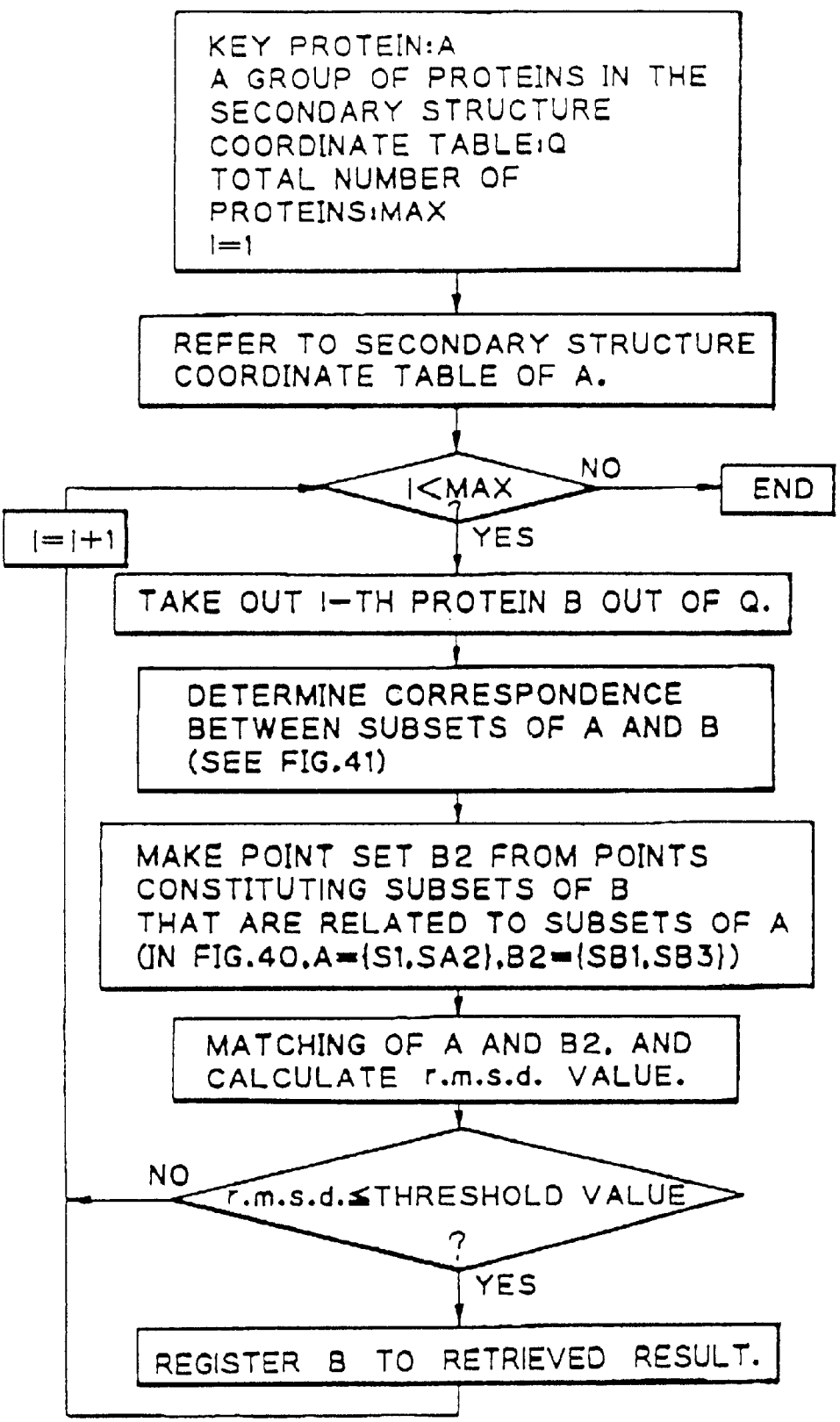
FIG. 45 is a flowchart showing a process for retrieving proteins using a method of dividing into subsets according to secondary structures.

FIG. 45 shows a processing carried out by the retrieving unit 164. The retrieving unit 164 reads the data stored in the secondary structure coordinate table 162 regarding a protein that serves as a key sent from the input unit 163 determines the correspondence of subsets, calculates the r.m.s.d between the two structures, and selects the one having an r.m.s.d. value that is smaller than the threshold value, thereby retrieving the structure having a high degree of similarity. The correspondence is determined based on the aforementioned method of determining correspondence among the subsets. In this case, the attribute of the subsets is the type of secondary structure. The correspondence is fixed only when the type of the two subsets are the same and when the r.m.s.d. value is smaller than the threshold value when the structures are best matched.

Next, points are matched with each other with regard to the sets constituted by points that belongs to the related subsets, and the r.m.s.d. value of the whole structure is calculated. In the example of FIG. 40, SA1 and SB1 are related to each other, and SA2 and SB3 are related to each other. In this case, match is effected among the points belonging to the sets (SA1, SA2) and the points belonging to the sets (SB1, SB3), and the r.m.s.d. value is calculated. When the r.m.s.d. value is smaller than the threshold value, the structure is determined to have a similarity and is registered to the retrieved result. This operation is carried out for all of the proteins stored in the secondary structure coordinate table 162, and the three-dimensional structures that are similar to each other in secondary structure are retrieved from all of the data.

(f) Display Unit

Based on the results retrieved by the retrieving unit 164, the display unit 165 displays the name of proteins having similar structures, secondary structures of a key protein and proteins having similar structures, and amino acids constituting the secondary structures.

Figure 46:
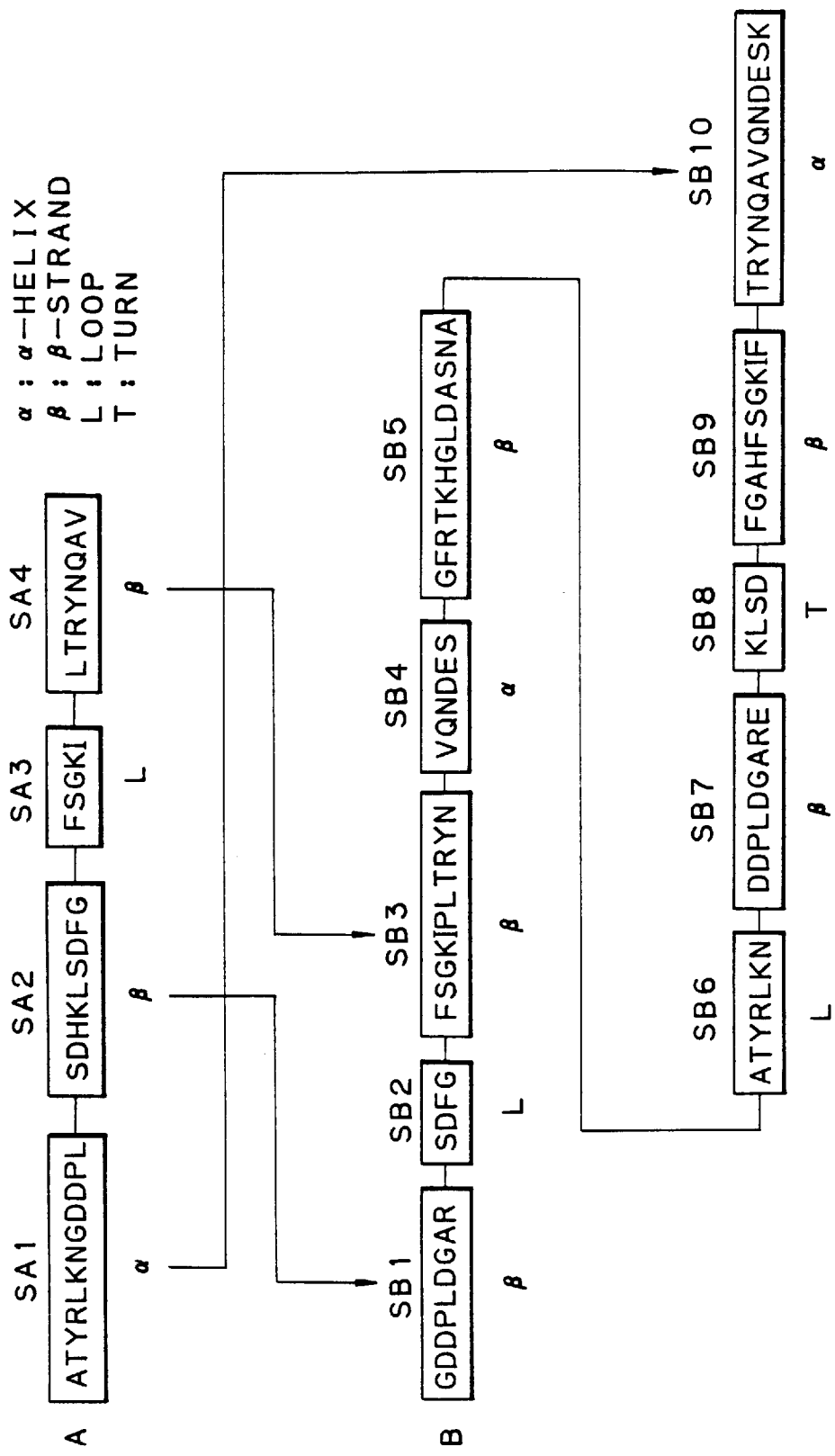
FIG. 46 is a diagram showing an output result of a similar retrieval structure using a protein as a retrieval key.
Figure 47:
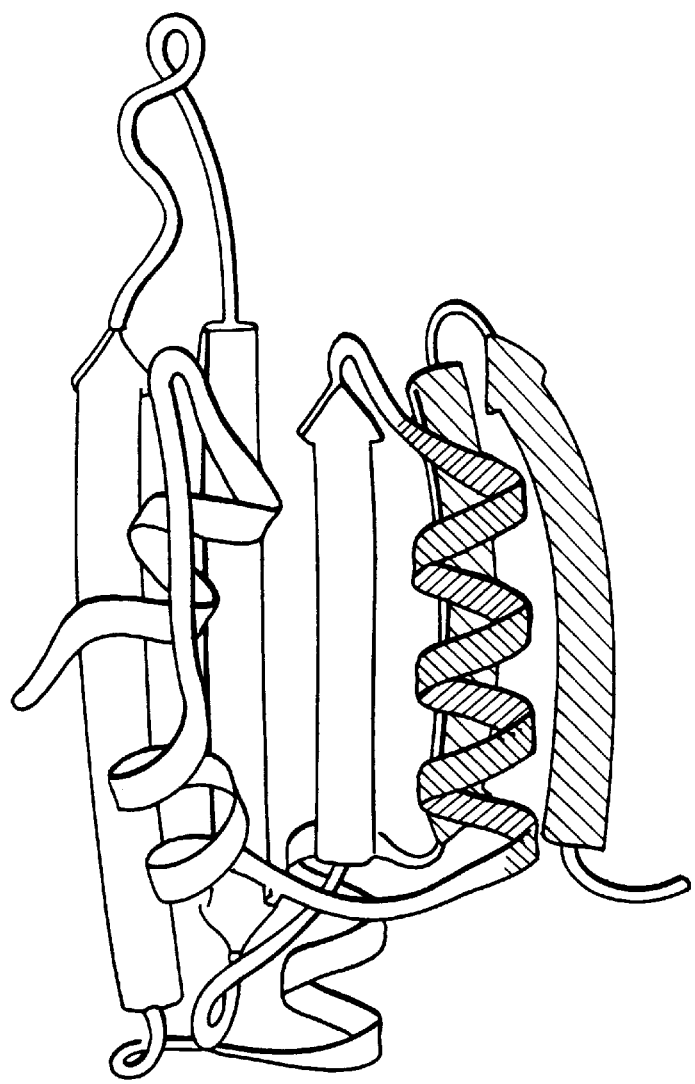
FIGS. 47A and 47B are diagrams showing a protein having a similar structure retrieved by a key protein.
Figure 47:
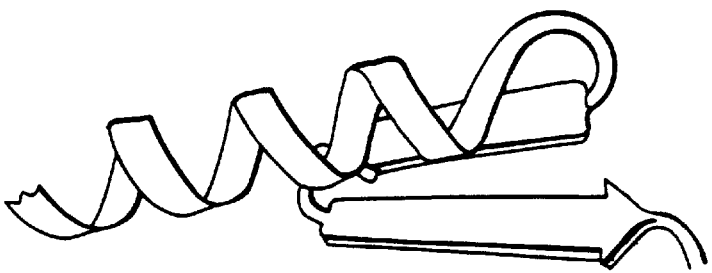

FIG. 46 shows examples of outputs. FIGS. 47A and 47B illustrate three-dimensional structures of a key protein A used in retrieval and a protein B having a similar structure that is retrieved.

In FIGS. 47A and 47B, a partial structure of α-helix is represented by a helical ribbon, a partial structure of β-strand is represent by an arrow, and partial structures of loop and turn are represented by tubes. As a result, it will be understood that the key protein is divided into four partial structures of α-helix, β-strand, loop and β-strand in the order of amino acid sequence, and these partial structure correspond to subsets SA1, SA2, SA3 and SA4, respectively.

Referring to FIG. 46, subsets SA1, SA2 and SA4 in A are similar to subsets SB10, SB1 and SB3 indicated by arrows in B, and are further similar in their relationship of spatial positions of the three partial structures. In A, a loop portion SA does not have an arrow indicating that there is no similar partial structure. Similar portions in the protein B of similar structure are hatched in FIG. 47B.

What is claimed is:

1. A computer-implemented method of analyzing sequences of atomic groups, said method comprising the steps of:

a) inputting, into a gene information survey apparatus, a plurality of sequences including a first sequence of characters $a_1$ to $a_m$ corresponding to a sequence of atomic groups in a first chain of atomic groups and a second sequence of characters $b_1$ to $b_n$ corresponding to a sequence of atomic groups in a second chain of atomic groups, wherein m and n are integers, wherein said gene information survey apparatus comprises a longest common subsequence detection unit and said second sequence of characters $b_1$ to $b_n$ are input to the longest common subsequence detection unit from one of an amino acid sequence data base and a motif data base;

b) generating, by the gene information survey apparatus, an occurrence table indicative of occurrence positions of the characters $a_1$ to $a_m$ in the first sequence;

c) preparing, by the gene information survey apparatus, a memory element array having memory elements $S_0$ to $S_m$, said memory elements $S_1$ to $S_m$ corresponding to said characters $a_1$ to $a_m$, respectively;

d) initializing, by the gene information survey apparatus, all memory elements $S_0$ to $S_m$ to zero and initializing an integer j to 1;

e) determining, by the gene information survey apparatus, an occurrence position r of a character $a_r$ that is the same as a character $b_j$ by referring to the occurrence table;

f) adding, by the gene information survey apparatus, 1 to each memory element $S_i$ where $i \geq r$ and $S_i$ is equal to a memory element $S_{r-1}$ when the memory element $S_r$ is equal to the memory element $S_{r-1}$, wherein the adding step is repeated in decreasing order of the occurrence position r when there is more than one occurrence position r;

g) adding, by the gene information survey apparatus, 1 to the integer j;

h) repeating, by the gene information survey apparatus, the steps e) to g) until the integer j exceeds n;

i) obtaining, by the gene information survey apparatus, a length of a longest common subsequence between the first and the second chains of atomic groups from a value of the memory element $S_m$ after the integer j exceeds n in step h);

j) analyzing, by the gene information survey apparatus, the sequences of atomic groups in the first and second chains of atomic groups using the length of a longest common subsequence; and k) displaying the longest common subsequence and results of the analyzing step on a display device.

2. A method according to claim 1, further comprising the steps of:

l) preparing, by the gene information survey apparatus, a second memory element array having memory elements $data_0$ to $data_n$ when $n \leq m$ and having memory elements $data_0$ to $data_m$ when $n > m$;

m) storing, by the gene information survey apparatus, paired data (r, j) in a memory element $data_k$ if the memory element $S_i$ is changed in the step f) where $k=S_r$;

n) linking, by the gene information survey apparatus, the paired data (r, j) stored in the step l) to paired data (r', j') if r'<r and j'<j where the paired data (r',j') is one stored in a memory element $data_{k-1}$; and o) obtaining, by the gene information survey apparatus, the longest common subsequence between the first and the second chains of atomic groups and occurrence positions of the longest common subsequence in the first and the second chains of atomic groups by tracing the link formed in the step m).

3. A method according to claim 1, wherein said step j) includes evaluating, by the gene information survey apparatus, homology between the first and second sequences based on the length of the longest common subsequence and a value of one of m and n.

4. A method according to claim 3, further comprising the step of:

l) searching, by the gene information survey apparatus, for a sequence that is homologous with the first sequence from among a plurality of sequences, by successively assigning one of the plurality of sequences to the second sequence and executing the steps a) to j).

5. A gene information survey apparatus for analyzing sequences of atomic groups, comprising:

means for inputting a plurality of sequences including a first sequence of characters $a_1$ to $a_m$ corresponding to a sequence of atomic groups in a first chain of atomic groups and a second sequence of characters $b_1$ to $b_n$ corresponding to a sequence of atomic groups in a second chain of atomic groups, wherein m and n are integers, said means for inputting comprising an amino acid data sequence data base and a motif data base storing the second sequence of characters $b_1$ to $b_n$, said means for inputting the second sequence from one of the amino acid sequence data base and the motif data base;

a longest common subsequence detection unit comprising:

means for generating an occurrence table indicative of occurrence positions of the characters a, to am in the first sequence, means for preparing a memory element array having memory elements $S_0$ to $S_m$, said memory elements $S_1$ to $S_m$ corresponding to said characters $a_1$ to $a_m$, respectively, means for initializing all memory elements $S_0$ to $S_m$ to zero and initializing an integer j to 1, means for determining an occurrence position r of a character $a_r$ that is the same as a character $b_j$ by referring to the occurrence table, means for updating the memory array by adding 1 to each memory element $S_i$ where $i \geq r$ and that is equal to a memory element $S_{r-1}$ when the memory element $S_r$ is equal to the memory element $S_{r-1}$, wherein updating is repeated in decreasing order of the occurrence position r when there are multiple occurrences of the occurrence position r, means for incrementing the integer j by 1, means for repeatedly activating the determining means, the updating means and the incrementing means until the integer j exceeds n, and means for obtaining a length of a longest common subsequence between the first and second chains of atomic groups from a value of the memory element $S_m$ after the integer j exceeds n, in order to use said length of the longest common subsequence to analyze said sequences of atomic groups in the first and the second chains of atomic groups; and a display device displaying the longest common subsequence and results of the analysis.

6. An apparatus according to claim 5, further comprising:

means for preparing a second memory element array having memory elements to data $data_0$ to $data_n$ when $n \leq m$ or memory elements $data_0$ to $data_m$ when $n > m$;

means for storing paired data (r, j) in a memory element $data_k$ if the memory element $S_i$ is changed by the updating means where $k=S_r$;

means for linking the paired data (r, j) stored by the storing means to paired data (r', j') if r'<r and j'<j where the paired data (r', j') is one stored in a memory element $data_{k-1}$; and means for obtaining the longest common subsequence between the first and the second chains of atomic groups and occurrence positions of the longest common subsequence in the first and second chains of atomic groups by tracing the link formed by the linking means.

7. An apparatus to claim 6, further comprising:

means for evaluating homology between the first and second sequences based on the length of the longest common subsequence and a value of m and n.

* * * * *